(12) United States Patent
Zhi et al.

(10) Patent No.: US 7,163,946 B2
(45) Date of Patent: Jan. 16, 2007

(54) 5-SUBSTITUTED 7,9-DIFLUORO-5H-CHROMENO[3,4-F]QUINOLINE COMPOUNDS AS SELECTIVE PROGESTERONE RECEPTOR MODULATOR COMPOUNDS

(75) Inventors: Lin Zhi, San Diego, CA (US); Cornelis Arjan Van Oeveren, Carlsbad, CA (US); Bijan Pedram, San Diego, CA (US); Donald S. Karanewsky, Escondido, CA (US)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 34 days.

(21) Appl. No.: 10/684,212

(22) Filed: Oct. 10, 2003

(65) Prior Publication Data

US 2004/0152717 A1 Aug. 5, 2004

Related U.S. Application Data

(60) Provisional application No. 60/417,968, filed on Oct. 11, 2002.

(51) Int. Cl.
*A61K 31/4741* (2006.01)
*C07D 491/02* (2006.01)

(52) U.S. Cl. ......................... 514/285; 546/62
(58) Field of Classification Search ................ 514/285; 546/62
See application file for complete search history.

(56) References Cited

U.S. PATENT DOCUMENTS

| | | | |
|---|---|---|---|
| 3,635,941 A | 1/1972 | Weaver et al. | |
| 3,907,507 A | 9/1995 | Rivera | |
| 5,506,102 A | 4/1996 | McDonnell et al. | 435/6 |
| 5,693,646 A | 12/1997 | Jones et al. | |
| 5,693,647 A | 12/1997 | Jones et al. | |
| 5,696,127 A | 12/1997 | Jones et al. | |
| 5,994,544 A | 11/1999 | Jones et al. | 546/62 |
| 6,093,826 A | 7/2000 | Edwards et al. | 546/62 |
| 6,268,497 B1 | 7/2001 | Edwards et al. | 546/62 |
| 6,380,207 B1 | 4/2002 | Coghlan et al. | 514/285 |
| 6,448,405 B1 | 9/2002 | Jones et al. | 546/62 |
| 6,506,766 B1 | 1/2003 | Coghlan et al. | 514/285 |
| 6,696,459 B1 | 2/2004 | Jones et al. | 514/285 |
| 2004/0147530 A1 | 7/2004 | Zhi et al. | 514/256 |
| 2004/0152718 A1 | 8/2004 | Zhi et al. | 514/285 |

FOREIGN PATENT DOCUMENTS

| | | |
|---|---|---|
| DE | 2015351 A | 10/1970 |
| EP | 0513387 | 3/2000 |
| JP | 04 316557 | 11/1992 |
| WO | 96/19458 | 6/1996 |
| WO | 9619458 | 6/1996 |
| WO | 97/49709 | 12/1997 |
| WO | WO 99/41256 A1 | 8/1999 |
| WO | 200202565 | 6/2001 |
| WO | WO 99/41257 A1 | 4/2002 |
| WO | 2004033459 | 4/2004 |
| WO | 2004033460 | 4/2004 |
| WO | 2004033461 | 4/2004 |

OTHER PUBLICATIONS

Berger, T. S., et al., Interaction of Glucocorticoid Analogues with the Human Glucocorticoid Receptor. J. Steroid Biochem. Mol. Bio. 1992, 41, 733-738.
Pathirana, C., et al., Nonsteroidal Human Progesterone Receptor Modulators from the Marine Alga Cymopolia Babata. Mol. Pharm. 1995, 47, 630-635.
Zhi, Lin et al., "Development of Progesterone Receptor Antagonists From 1,2-Dihydrochromeno [3,4-f] Quinoline Agonist Pharmacophore", *Bioorganic & Medicinal Chemistry Letters*, 13 (2003), 2075-2078.
International Search Report for related PCT International Application No. PCT/US03/24420, filed Aug. 4, 2003 (dated Feb. 18, 2004).
Clemm et al., "Definition of the critical cellular components which distinguish between hormone and antihormone activated progesterone receptor," Journal of Steroid Biochemisry and Molecular Biology 53(1-6):487-495, (1995).
Edwards et al., "5-Aryl-1,2-dihydro-5H-chromeno[3,4-f]quinolines as potent, orally active, nonsteroidal progesterone receptor agonists: the effect of D-ring substituents," Journal of Medicinal Chemistry. 41(3):303-310 (1998).
Edwards et al., "Preparation, resolution, and biological evaluation of 5-aryl-1, 2-dihydro-5H-chromeno[3,4-f] quinolines: potent, orally active, nonsteroidal progesterone receptor agonists," Journal of Medicinal Chemistry 41(15):2779-2785 (1998).
Hamann et al., "Nonsteroidal progesterone receptor antagonists based on a conformationally-restricted subseries of 6-aryl-1,2-dihydro-2,2,4-trimethylquinolines," Bioorganic & Medicinal Chemistry Letters 8(19):2731-2736 (1998).
McDonnell et al., "Definition of the cellular mechanisms which distinguish between hormone and antihormone activated steroid receptors," Seminars in Cancer Biology, 5(5):327-336 (1994).
Miner, J. N. and C.M. Tyree, "Drug discovery and the intracellular receptor family," Vitamins and Hormones. 62:253-280. (2001).
Rosen et al., "Intracellular receptors and signal transducers and activators of transcription superfamilies - novel targets for small-molecule drug discovery," Journal of Medicinal Chemistry 38(25):4855-4874 (1995).
Santiso-Mere, D. and D.P. McDonnell, "Applied nuclear receptor research in the drug discovery process," Chimica Oggi. 12(5-6):29-36. (1994).

(Continued)

*Primary Examiner*—Charanjit S. Aulakh
(74) *Attorney, Agent, or Firm*—Fish & Richardson, P.C.; Stephanie Seidman; Frank J. Miskiel

(57) ABSTRACT

The present invention is directed to compounds, pharmaceutical compositions, and methods for modulating processes mediated by progesterone receptor. Also provided are methods of making such compounds and pharmaceutical compositions.

25 Claims, No Drawings

OTHER PUBLICATIONS

Silverman, R.B., "Prodrugs and Drug Delivery Systems," Chapter 8 in The Organic Chemistry of Drug Design and Drug Action, San Diego: Academic Press, Inc., pp. 352-401 (1992).

Tegley et al., "5-Benzylidene 1,2-dihydrochromeno[3,4-f]quinolines, a novel class of nonsteroidal human progesterone receptor agonists," Journal of Medicinal Chemistry. 41(22):4354-4359. (1998).

Vegeto et al., "Human progesterone receptor A form is a cell- and promoter-specific repressor of human progesterone receptor B function," Molecular Endocrinology. 7(10):1244-1255. (1993).

Wagner et al., "The novel progesterone receptor antagonists RTI 3021-012 and RTI 3021-022 exhibit complex glucocorticoid receptor antagonist activities: Implications for the development of dissociated antiprogestins," Endocrinology 140(3):1449-1458 (1999).

Wen et al., "The A and B isoforms of the human progesterone receptor operate through distinct signaling pathways within target cells," Molecular and Cellular Biology 14(12):8356-8364 (1994).

Zhi, L. and K.B. Marschke, "Novel class of non-steroidal progesterone receptor antagonists," Expert Opinion on Therapeutic Patents. 9(6):695-700 (1999).

Zhi et al., "5-Alkyl 1,2-dihydrochromeno[3,4-f]quinolines: a novel class of nonsteroidal progesterone receptor modulators," Bioorganic & Medicinal Chemistry Letters 8(23):3365-3370 (1998).

Zhi, et al. "Synthesis and biological Activity of 5-Methylidine 1,2-Dihydrochromeno[3,4-f]quinoline Derivatives as Progesterone Receptor Modulators" Bioorganic & Medicinal Chemistry Letters 13:2071-2074 (2003).

Zhi et al., "5-Aryl-1,2-dihydrochromeno[3,4-f]quinolines: a novel class of nonsteroidal human progesterone receptor agonists," Journal of Medicinal Chemistry 41(3):291-302 (1998).

Zhi et al., "5-Aryl-1,2,3,4-tetrahydrochromeno[3,4-f]quinolin-3-ones as a novel class of nonsteroidal progesterone receptor agonists: effort of A-ring modification," Journal of Medicinal Chemistry. 42(8):1466-1472 (1999).

Zhi et al., "5-Benzylidene-1,2-dihydrochromeno[3,4-f]quinolines as Selective Progesterone Receptor Modulators," Journal of Medicinal Chemistry 46(19):4104-4112 (2003).

Berger et al. "Interaction of Glucocorticoid Analogues with the Human Glucocorticoid Receptor," J. Steroid Biochem. Molec. Biol., vol.41, No. 3-8, pp. 733-738 (1992).

Brown, J.P. and L.M. Jackman, "Reactions of 2,2-Dialkyl-1,2-dihydroquinolines. Part II. Bromo-derivatives of 1,2-Dihydro-2,2,4-trimethylquinoline," Journal of the Chemical Society, Sep. 1964, pp. 3132-3140.

Chemical Abstracts, vol. 87, No. 13, Sep. 26, 1977 (Sep. 26, 1977), Abstract No. 102120c for: Migachev,et al., "Synthesis of substituted derivatives of 6H-dibenzo [b,d]pyran-6-one," Khim. Geterotsikl. Soedin. (1977), (5), 703-4.

Cook et al., "Reversal of Activity Profile in Analogs of the Antiprogestin RU 486: Effect of a 16a-Substituent on Progestational (Agonist) Activity," Life Sciences vol. 52, pp. 155-162 (1992).

Database CAPLUS, Chemical Abstracts AN=1975:111718 for Endel'man et al. "[N-phenylanthranilic acids with fluorine-containing substituents]," Ukr. Khim. Zh. (Russ. Ed.) vol. 40, No. 12, pp. 1295-5 (1974).

Database CAPLUS, Chemical Abstracts AN=118:147477 for Japanese Patent Publication No. JP 04316557, published Nov. 6, 1992, Kono et al., entitled: "Preparationof 6-aryl-cyclic anthranilic acids and their use as therapeutics for treatment of metabolic bone disorder".

Database CAPLUS, Chemical Abstracts AN=70:87515 for Kost et al., "Pyridylation of 1-alkyl-1,2,3,4-tetrahydroquinolines," Khim. Geterotsikl. Soedin., Sb., 1: Azotsoderzhashchie Geterotsikly (1967), pp. 248-53, Editor(s): Hillers, S., Publisher: Izd. "Zinatne" Riga, USSR.

Database CAPLUS, Chemical Abstracts AN=1993:613822 for Samsonova et al., "Spectroscopic studies of photoreactions in aminocoumarins," Kvantovaya Elektron (Kiev) vol. 41, pp. 63-72 (1992).

Database CAPLUS, Chemical Abstracts AN=1992:22860 for Song, et al., "Solvent effect of nonradiative transition yield for coumarin derivative," Chinese Science Bulletin, vol. 36, No. 12, pp. 1000-1003, (1992).

Datebase Crossfire Beilstein 'Online!, XP 002002687, BRN=880985 & J. Org. Chem. USSR, vol. 9, 1973, pp. 2571-2576.

Database Crossfire Beilstein 'Online!, XP 002002688, BRN=143474 & Journal of Organic Chemistry, vol. 30, 1965, pp. 3560-3561.

Database Crossfire Belistein 'Online!XP002002689, BRN=18052 & Ueda: Yakugaku Zasshi, vol. 57, 1937, pp. 312-316.

Database Crossfire Beilstein 'Online!, XP 002002690, BRN=185528 & Anal. Chem., vol. 27, 1955, pp. 101-101.

Database Crossfire Beilstein 'Online!, XP 002002691, BRN=384096 & Chemische Berichte, vol. 35, 1902, p. 3278.

Database Crossfire Beilstein 'Online!0 XP002002692, BRNos. =193508 and 211894 & Journal of the American Chemical Society, vol. 457, 1935, p. 902.

Database Crossfire Beilstin 'Online!, XP 002002693, BRN=1129121 & Journal of Organic Chemistry, vol. 43, 1978, pp. 1975-1980.

Database Crossfire Beilstein 'Online!, XP 002002694, BRNos. =1241334 and 1682456 & Bull. Acad. Sci. USSR Div. Chem. Sci (Engl. Trans.), vol. 25, 1976 pp. 2069-2071.

Database Crossfire Beilstein 'Online!, XP 002002695, BRNos. =48005330 4800630, and 4804716 & Journal of Medicinal Chemistry, vol. 34, No. 11, 1991, pp. 3261-3267.

Database Crossfire Beilstein 'Online!, XP002002696, BRN=424721 & DE 20 15 351 A, Oct. 15, 1970 (Oct. 15, 1970).

Database Crossfire Beilstein 'Online!, XP002002697, BRN=140265 & US 3 907 507 A 23 Sep. 1995 (Sep. 23- 1975).

Database Crossfire Beilstein 'Online!, XP002002698, BRN=640834 & Journal of the Chemical Society, 1964, pp. 3132-3140.

Database Crossfire Beilstein 'Online!, XP 002002699, BRN=390257 & Journal of Medicinal Chemistry, vol. 15, 1972, pp. 1177-1179.

Database Crossfire Beilstein 'Online!, XP002002698, BRN=1566891 & Helvetica Chimica Acta, vol. 60, 1977, pp. 978-1021.

Database Crossfire Beilstein 'Online!, XP002002701, BRN=269284 & Journal of the American Chemical Society, vol. 66, 1994, p. 1927.

Endel'man et al. "[N-phenylanthranilic acids with fluorine-containing substituents], " Ukr. Khim. Zh. (Russ. Ed.) vol. 40, No. 12, pp. 1292-5 (1974) [In Russian].

Fletcher, A.N. and D.E. Bliss, "Laser Dye Stability. Part 5. Effect of Chemical Substituents of Bicyclic Dyes Upon Photodegradation Parameters," Appl. Phys. vol. 16, No. 3, pp. 289-295 (1978)

Horner, L. and D.W. Baston, "Investiagations on o-Quinones, XXXIV. -Experiments for the Preparation of Quinones Derived from Fluorene and Fluorenone," Justus Liebigs Ann. Chem., 5-6, pp. 910-935 (1973) [In German with an English language abstract on the first page of the article].

Manthey et al., "Structural Elucidation and Independent Synthesis of the Radical-Radical Coupling Products of 3-Hydroxyanthranilic Acid with Tyrosine and Phenols," J. Org. Chem. 55(15):4581-4585 (1990).

Mosettig, E. and R.A. Robinson, "Benzofuroquinolines," Journal of the American Chemical Society, vo. 57, p. 902 (1935).

Ota, E and M. Okazaki, "the Synthesis of 3,4-Benzocumarins from Diphenic Acids," Yuki Gosei Kagaku Kyokai Shi., vol. 28, No. 3, pp. 341-345, (1970) [In Japanese with an English language abstract on the first page of the article].

Samsonova et l., "[Spectroscopic studies of photoreactions in aminocoumarins], " Kvantovaya Elektorn. (Kiev), vol. 41, pp. 63-72 (1992) [In Russian].

Song, et al., "Solvent effect of nonradiative transition yield for coumarin derivative," Chinese Science Bulletin, vol. 36, No. 12, pp. 1000-1003, (1992).

Suri, S.C. and V. Nair, "Palladium(0)-Catalyzed Reaction of 2-Bromo-7-Methoxytropone with Arylboronic Acids: An Efficient Synthesis of 2-Aryl-7-Methoxytropones," Synthesis, vol. 8, pp. 695-696 (Aug. 1990).

Teutsch, G. and D. Philibert, "History of perspectives of antiprogestins from the chemist's point of view," Human Reproduction vol. 9 (suppl. 1) pp. 12-31, (1994).

Tod, et al., "Analytical Implications of Luminescence Parameters in Liquid Chromatography: Applications to Aminocoumarins in the Peroxyoxalate Chemiluminescent Reaction," Analytica Chimica Acta, vol. 217, No. 1, pp. 11-21 (1989).

5-SUBSTITUTED 7,9-DIFLUORO-5H-CHROMENO[3,4-F]QUINOLINE COMPOUNDS AS SELECTIVE PROGESTERONE RECEPTOR MODULATOR COMPOUNDS

RELATED APPLICATIONS

This application claims the benefit of priority of U.S. Provisional Application Ser. No. 60/417,968 filed Oct. 11, 2002, the entire disclosure of which is incorporated herein by reference.

FIELD OF THE INVENTION

This invention relates to 5-substituted 7,9-difluoro-1,2-dihydro-2,2,4-trimethyl-5H-chromeno[3,4-f]quinoline compounds that may be highly potent receptor- and tissue-selective modulators (i.e. agonists, partial agonists and antagonists) of progesterone receptors and to methods for the making and use of such compounds.

BACKGROUND OF THE INVENTION

Progesterone receptor (PR) modulators have been widely used in regulation of female reproduction systems and in treatment of female hormone dependent diseases. The effectiveness of known steroidal PR modulators is often tempered by their undesired side-effect profile, particularly during long-term administration. For example, the effectiveness of synthetic progestins as female birth control agents or hormone replacement therapies must be weighed against the increased risk of breast cancer due to progestins' proliferative activity in breast tissue. Similarly, the progesterone antagonist, mifepristone (RU486), if administered for chronic indications, such as uterine fibroids, endometriosis and certain hormone-dependent cancers, could lead to homeostatic imbalances in a patient due to its inherent cross-reactivity as a glucocorticoid receptor (GR) antagonist. Accordingly, identification of compounds that have good receptor-selectivity for PR over other steroid hormone receptors as well as good tissue-selectivity (e.g. selectivity for uterine tissue over breast tissue) would be of significant value in the improvement of women's health.

A group of nonsteroidal molecules which contain a di- or tetra-hydroquinoline ring as core pharmacophore (U.S. Pat. Nos. 5,693,646; 5,693,647 and 5,696,127; PCT Int. Publication Nos. WO 99/41256 A1 and WO 99/41257 A1) have been described as steroid hormone receptor modulator compounds.

The entire disclosures of the patents, publications and references referred to herein are incorporated by reference herein and are not admitted to be prior art.

SUMMARY OF THE INVENTION

The present invention is directed to compounds, pharmaceutical compositions, and methods for modulating processes mediated by Progesterone Receptor. More particularly, the invention relates to 5-substituted 7,9-difluoro-1,2-dihydro-2,2,4-trimethyl-5H-chromeno[3,4-f]quinoline compounds and compositions which may be high affinity, high specificity agonists, partial agonists (i.e., partial activators and/or tissue-specific activators) and/or antagonists for progesterone receptors. Also provided are methods of making such compounds and pharmaceutical compositions. Compounds of the present invention may be represented by the formulae:

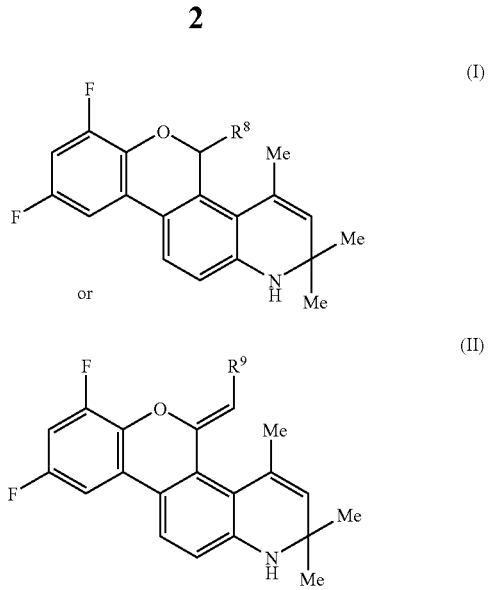

wherein:

$R^8$ is selected from the group of $C_1$–$C_{12}$ alkyl, $C_1$–$C_{12}$ heteroalkyl, $C_1$–$C_{12}$ haloalkyl, $C_2$–$C_{12}$ alkenyl, $C_2$–$C_{12}$ heteroalkenyl, $C_2$–$C_{12}$ haloalkenyl, $C_2$–$C_{12}$ alkynyl, $C_2$–$C_{12}$ heteroalkynyl, $C_2$–$C_{12}$ haloalkynyl, aryl and heteroaryl, wherein said alkyl, heteroalkyl, haloalkyl, alkenyl, heteroalkenyl, haloalkenyl, heteroalkynyl, haloalkynyl, alkynyl, aryl and heteroaryl radicals are optionally substituted;

$R^9$ is selected from the group of hydrogen, F, Cl, Br, I, CN, $C_1$–$C_8$ alkyl, $C_1$–$C_8$ heteroalkyl, $C_1$–$C_8$ haloalkyl, $C_2$–$C_8$ alkenyl, $C_2$–$C_8$ heteroalkenyl, $C_2$–$C_8$ haloalkenyl, $C_2$–$C_8$ alkynyl, $C_2$–$C_8$ heteroalkynyl, $C_2$–$C_8$ haloalkynyl, aryl and heteroaryl, wherein said alkyl, heteroalkyl, haloalkyl, alkenyl, heteroalkenyl, haloalkenyl, heteroalkynyl, haloalkynyl, alkynyl, aryl and heteroaryl radicals are optionally substituted;

and pharmaceutically acceptable salts and prodrugs thereof.

DEFINITIONS AND NOMENCLATURE

As used herein, the following terms are defined with the following meanings, unless explicitly stated otherwise. Furthermore, in an effort to maintain consistency in the naming of compounds of similar structure but differing substituents, the compounds described herein are named according to the following general guidelines. The numbering system for the location of substituents on such compounds is also provided.

A 5H-chromeno[3,4-f]quinoline is defined by the following structure.

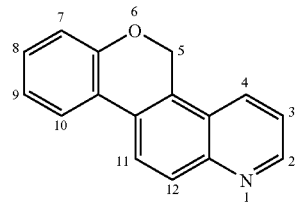

The term "alkyl," alone or in combination, refers to an optionally substituted straight-chain or branched-chain or cyclic alkyl radical typically having from 1 to about 12 carbon atoms. The term also includes substituted straight-chain or branched-chain alkyl radicals having from 1 to about 6 carbon atoms as well as those having from 1 to about 4 carbon atoms. Examples of alkyl radicals include methyl, ethyl, n-propyl, isopropyl, n-butyl, isobutyl, sec-butyl, tert-butyl, tert-amyl, pentyl, hexyl, heptyl, octyl and the like.

The term "alkenyl," alone or in combination, refers to an optionally substituted straight-chain or branched-chain hydrocarbon radical having one or more carbon-carbon double-bonds and having from 2 to about 18 carbon atoms. The term also includes substituted straight-chain or branched-chain alkyl radicals having one or more carbon-carbon double bonds and typically having from 2 to about 6 carbon atoms as well as those having from 2 to about 4 carbon atoms. Examples of alkenyl radicals include ethenyl, propenyl, 1,3-butadienyl and the like.

"Allyl" alone or in combination refers to —CH$_2$—CH=CH$_2$.

"Methylidene" alone or in combination refers to =CH$_2$.

The term "alkynyl," alone or in combination, refers to an optionally substituted straight-chain or branched-chain hydrocarbon radical having one or more carbon-carbon triple-bonds and typically having from 2 to about 12 carbon atoms. The term also includes substituted straight-chain or branched-chain alkyl radicals having one or more carbon-carbon triple bonds and having from 2 to about 6 carbon atoms as well as those having from 2 to about 4 carbon atoms. Examples of alkynyl radicals include ethynyl, propynyl, butynyl and the like.

The term "heteroalkyl," "heteroalkenyl" and "heteroalkynyl" refer to alkyl, alkenyl and alkynyl radicals, as described above, in which one or more skeletal atoms are heteroatoms such as, for example, oxygen, nitrogen, sulfur or combinations thereof. The terms heteroalkyl, heteroalkenyl and heteroalkynyl include radicals in which 1 to about 6 skeletal atoms are oxygen, nitrogen, sulfur or combinations thereof, as well as those in which 1 to 4 skeletal atoms are oxygen, nitrogen, sulfur or combinations thereof and those in which 1 to 2 skeletal atoms are oxygen, nitrogen, sulfur or combinations thereof.

The term "aryl," alone or in combination, refers to an optionally substituted aromatic ring system. The term aryl includes monocyclic aromatic rings, polyaromatic rings and polycyclic aromatic ring systems containing from to six about twenty carbon atoms. The term aryl also includes monocyclic aromatic rings, polyaromatic rings and polycyclic ring systems containing from six to about 12 carbon atoms, as well as those containing from 6 to about 10 carbon atoms. The polyaromatic and polycyclic aromatic rings systems may contain from two to four rings. Examples of aryl radicals include, without limitation, phenyl, biphenyl, naphthyl and anthryl ring systems.

The term "heteroaryl" refers to an optionally substituted aromatic ring system containing from about five to about 20 skeletal ring atoms and having one or more heteroatoms such as, for example, oxygen, nitrogen and sulfur. The term heteroaryl also includes optionally substituted aromatic ring systems having from 5 to about 12 skeletal ring atoms, as well as those having from 5 to about 10 skeletal ring atoms. The term heteroaryl may include five- or six-membered heterocyclic rings, polycyclic heteroaromatic ring systems and polyheteroaromatic ring systems where the ring system has two, three or four rings. The terms heterocyclic, polycyclic heteroaromatic and polyheteroaromatic include ring systems containing optionally substituted heteroaromatic rings having more than one heteroatom as described above (e.g., a six membered ring with two nitrogens), including polyheterocyclic ring systems of from two to four rings. The term heteroaryl includes ring systems such as, for example, furanyl, benzofuranyl, chromenyl, pyridyl, pyrrolyl, indolyl, quinolinyl, N-alkyl pyrrolyl, pyridyl-N-oxide, pyrimidyl, pyrazinyl, imidazolyl, pyrazolyl, oxazolyl, benzothiophenyl, purinyl, indolizinyl, thienyl and the like.

The terms haloalkyl, haloalkenyl, haloalkynyl and haloalkoxy include alkyl, alkenyl, and alkynyl structures, as described above, that are substituted with one or more fluorines, chlorines, bromines or iodines, or with combinations thereof.

The terms cycloalkyl, aryl, arylalkyl, heteroaryl, alkyl, alkynyl, alkenyl, haloalkyl and heteroalkyl include optionally substituted cycloalkyl, aryl, arylalkyl, heteroaryl, alkyl, alkynyl, alkenyl, haloalkyl and heteroalkyl radicals.

The term "carbocycle" includes optionally substituted, saturated or unsaturated, three- to eight-membered cyclic structures in which all of the skeletal atoms are carbon.

The term "heterocycle" includes optionally substituted, saturated or unsaturated, three- to eight-membered cyclic structures in which one or more skeletal atoms is oxygen, nitrogen, sulfur, or combinations thereof.

The term "acyl" includes alkyl, aryl, heteroaryl, arylalkyl or heteroarylalkyl substituents attached to a compound via a carbonyl functionality (e.g., —CO-alkyl, —CO-aryl, —CO-arylalkyl or —CO-heteroarylalkyl, etc.).

The term "halogen" includes F, Cl, Br and I.

The term "mediate" means affect or influence, frequently indirectly or via some intervening action. Thus, for example, conditions mediated by a progesterone receptor are those in which a progesterone receptor plays a role. Progesterone receptors are known to play a role in conditions including, for example, infertility, contraception, pregnancy maintenance and termination, female hormone deficiency, female sexual dysfunction, dysfunctional uterine bleeding, endometriosis, mood disorder, osteoporosis, and hormone-dependent cancers.

The term "receptor-selectivity" refers to the conditions where a compound displays modulating activity towards one or more particular receptors (e.g., a progesterone receptors) while displaying substantially less or no cross-reactivity towards one or more different receptors (e.g., glucocorticoid receptors). Thus, for example, selective compounds of the present invention may display modulating activity towards progesterone receptors without displaying substantial cross-reactivity towards another steroid hormone receptors. Compounds may be selective for a single receptor, group of similar receptors or multiple receptors.

The term "tissue-selectivity" refers to compounds that display substantial modulating activity in one tissue (e.g., uterine tissue) while displaying lesser modulating activity in at least one other tissue (e.g., breast tissue). Thus, for example, tissue-selective compounds of the present invention may display substantial modulating activity in uterine and vaginal tissues with lesser modulating activity (partial agonistic or partial antagonistic) in breast tissues relative to the activities of the marketed steroidal progestins in all of the target tissues.

The term "modulate" means affect or influence, for example, the amount, degree or proportion. Thus, compounds that "modulate" a receptor affect the activity, either positively or negatively, of that receptor. The term may be used to refer to the activity of compounds of a receptor as, for example, an agonist, partial agonist or antagonist. The term also may be used to refer to the effect that a compound has on a physical and/or physiological condition of an individual. For example, certain compounds of the present invention may be used to modulate fertility in an individual. That is, certain compounds of this invention may be used to increase the fertility of an individual, while other compounds of this invention may be used to decrease the fertility of an individual.

A compound that binds to a receptor and mimics the effect of the native or endogenous ligand is referred to as an "agonist," while a compound that binds to a receptor and inhibits or has an effect that is opposite that of the native or endogenous ligand is called an "antagonist." "Partial agonists" give an effect of the same type as the native or endogenous ligand, but of a lower magnitude, while "partial antagonists" are incompletely inhibitory or opposite that of the native or endogenous ligand.

DETAILED DESCRIPTION OF THE INVENTION

Compounds of the present invention may be represented by the formulae:

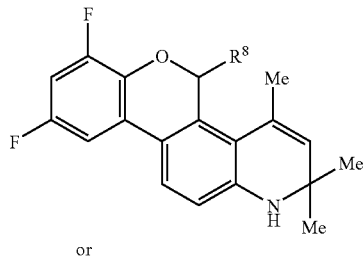
(I)

or

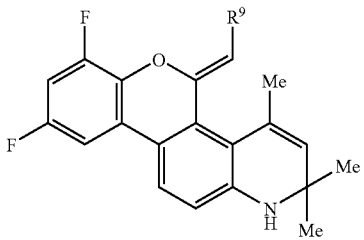
(II)

wherein:

$R^8$ is selected from the group of $C_1$–$C_{12}$ alkyl, $C_1$–$C_{12}$ heteroalkyl, $C_1$–$C_{12}$ haloalkyl, $C_2$–$C_{12}$ alkenyl, $C_2$–$C_{12}$ heteroalkenyl, $C_2$–$C_{12}$ haloalkenyl, $C_2$–$C_{12}$ alkynyl, $C_2$–$C_{12}$ heteroalkynyl, $C_2$–$C_{12}$ haloalkynyl, aryl and heteroaryl, optionally substituted with one or more substituents independently selected from the group of hydrogen, $C_1$–$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_2CH_3$, $C(O)NH_2$, $OR^{10}$, $SR^{10}$, and $NR^{10}R^{11}$;

$R^9$ is selected from the group of hydrogen, F, Cl, Br, I, CN, $C_1$–$C_8$ alkyl, $C_1$–$C_8$ heteroalkyl, $C_1$–$C_8$ haloalkyl, $C_2$–$C_8$ alkenyl or cycloalkenyl, $C_2$–$C_8$ heteroalkenyl, $C_2$–$C_8$ haloalkenyl, $C_2$–$C_8$ alkynyl, $C_2$–$C_8$ heteroalkynyl, $C_2$–$C_8$ haloalkynyl, aryl and heteroaryl optionally substituted with one or more substituents independently selected from the group of hydrogen, $C_1$–$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_2CH_3$, $C(O)NH_2$, $OR^{10}$, $SR^{10}$, and $NR^{10}R^{11}$; and $R^{10}$ and $R^{11}$ each independently is hydrogen or $C_1$–$C_4$ alkyl; and pharmaceutically acceptable salts and prodrugs thereof.

In one embodiment, $R^8$ is selected from the group of:

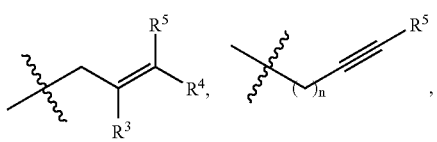

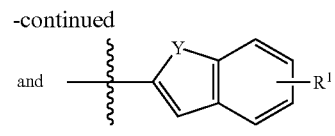

$R^1$ and $R^2$ each independently is selected from the group of hydrogen, F, Cl, Br and $C_1$–$C_4$ alkyl;

$R^3$ through $R^5$ each independently is selected from the group of hydrogen, F, Cl and $C_1$–$C_4$ alkyl;

$R^6$ is selected from the group of hydrogen, F, Cl, Br, $C_1$–$C_4$ alkyl, $OR^{10}$, $SR^{10}$, and $NR^{10}R^{11}$;

$R^7$ is hydrogen, F, or Cl;

$R^{10}$ and $R^{11}$ each independently is hydrogen or $C_1$–$C_4$ alkyl;

n is 0 or 1;

X is CH or N; and

Y is selected from the group of O, S, and $NR^{10}$;

and pharmaceutically acceptable salts and prodrugs thereof.

In another embodiment, $R^6$ is selected from the group of F, Me, Et, OMe, OEt, SMe, and $NMe_2$.

In another embodiment, $R^9$ is selected from the group of:

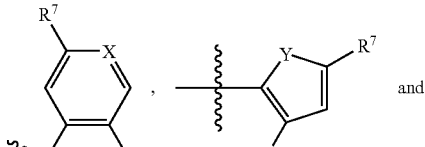

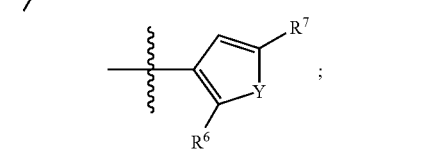

$R^6$ is selected from the group of hydrogen, F, Cl, Br, $C_1$–$C_4$ alkyl, $OR^{10}$, $SR^{10}$, and $NR^{10}R^{11}$;

X is CH or N; and $R^7$ is hydrogen, F, or Cl; and

Y is selected from the group of O, S, and $NR^{10}$.

In another embodiment, $R^9$ is

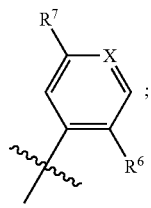

$R^6$ is selected from the group of hydrogen, F, Cl, Br, $C_1$–$C_4$ alkyl, $OR^{10}$, $SR^{10}$, and $NR^{10}R^{11}$;

$R^7$ is hydrogen, F, or Cl; and

X is CH or N.

In the following table, the inventors contemplate any combination of the following Markush groups and those described above for the various variables.

TABLE A

Table of Markush Groups by Variable

| | Markush Group A | Markush Group B | Markush Group C | Markush Group D |
|---|---|---|---|---|
| $R_1$ | H, F, Cl, Br and $C_1$–$C_4$ alkyl | F, Cl, Br and $C_1$–$C_2$ alkyl | F, Cl, Br and methyl | F and Cl |
| $R_2$ | H, F, Cl, Br and $C_1$–$C_4$ alkyl | F, Cl, Br and $C_1$–$C_2$ alkyl | F, Cl, Br and methyl | F and Cl |
| $R_3$ | H, F, Cl, and $C_1$–$C_4$ alkyl | F, Cl and $C_1$–$C_2$ alkyl | F, Cl and methyl | F and Cl |
| $R_4$ | H, F, Cl, and $C_1$–$C_4$ alkyl | F, Cl and $C_1$–$C_2$ alkyl | F, Cl and methyl | F and Cl |
| $R_5$ | H, F, Cl, and $C_1$–$C_4$ alkyl | F, Cl and $C_1$–$C_2$ alkyl | F, Cl and methyl | F and Cl |
| $R_6$ | H, F, Cl, Br, $C_1$–$C_4$ alkyl, $OR^{10}$, $SR^{10}$, and $NR^{10}R^{11}$ | H, F, Cl, $C_1$–$C_4$ alkyl, OMe, OEt, NHMe, and $NMe_2$ | F, Me, Et, OMe, OEt, SMe, and $NMe_2$ | F and methyl |
| $R_7$ | H, F, and Cl | F and Cl | | F |
| $R_8$ | $C_1$–$C_{12}$ alkyl, $C_1$–$C_{12}$ heteroalkyl, $C_1$–$C_{12}$ haloalkyl, $C_2$–$C_{12}$ alkenyl, $C_2$–$C_{12}$ heteroalkenyl, $C_2$–$C_{12}$ haloalkenyl, $C_2$–$C_{12}$ alkynyl, $C_2$–$C_{12}$ heteroalkynyl, $C_2$–$C_{12}$ haloalkynyl, aryl and heteroaryl, optionally substituted with one or more substituents independently selected from the group of H, $C_1$–$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_2CH_3$, $C(O)NH_2$, $OR^{10}$, $SR^{10}$ and $NR^{10}R^{11}$ | $C_1$–$C_8$ alkyl, $C_1$–$C_8$ heteroalkyl, $C_1$–$C_8$ haloalkyl, $C_2$–$C_8$ alkenyl, $C_2$–$C_8$ heteroalkenyl, $C_2$–$C_8$ haloalkenyl, $C_2$–$C_8$ alkynyl, $C_2$–$C_8$ heteroalkynyl, $C_2$–$C_8$ haloalkynyl, aryl and heteroaryl, optionally substituted with one or more substituents independently selected from the group of H, $C_1$–$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_2CH_3$, $C(O)NH_2$, $OR^{10}$, $SR^{10}$ and $NR^{10}R^{11}$ | aryl and heteroaryl, optionally substituted with one or more of H, $C_1$–$C_4$ alkyl, F, Cl, Br, CN, $NH_2$, $NHCH_3$, $N(CH_3)_2$, SH, $SCH_3$, OH, $OCH_3$, $OCF_3$, $CF_3$, $C(O)CH_3$, $OR^{10}$, $SR^{10}$ and $NR^{10}R^{11}$ | $C_1$–$C_4$ alkyl, $C_1$–$C_4$ heteroalkyl, $C_1$–$C_4$ haloalkyl, $C_2$–$C_4$ alkenyl, $C_2$–$C_4$ heteroalkenyl, $C_2$–$C_4$ haloalkenyl, $C_2$–$C_4$ alkynyl, $C_2$–$C_4$ heteroalkynyl, and $C_2$–$C_4$ haloalkynyl |
| $R_9$ | H, F, Cl, Br, I, CN, $C_1$–$C_8$ alkyl, $C_1$–$C_8$ heteroalkyl, $C_1$–$C_8$ haloalkyl, $C_2$–$C_8$ alkenyl or cycloalkenyl, $C_2$–$C_8$ heteroalkenyl, $C_2$–$C_8$ haloalkenyl, $C_2$–$C_8$ alkynyl, $C_2$–$C_8$ heteroalkynyl, $C_2$–$C_8$ haloalkynyl, aryl and heteroaryl, optionally substituted with one or more substituents independently selected from H, $C_1$–$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_2CH_3$, $C(O)NH_2$, $OR^{10}$, $SR^{10}$, and $NR^{10}R^{11}$ | aryl and heteroaryl, optionally substituted with one or more substituents independently selected from H, $C_1$–$C_4$ alkyl, F, Cl, Br, CN, $NH_2$, $NHCH_3$, $N(CH_3)_2$, SH, $SCH_3$, OH, $OCH_3$, $OCF_3$, $OR^{10}$, $SR^{10}$, and $NR^{10}R^{11}$ | H, Br, Cl, $C_1$–$C_4$ alkyl, $C_1$–$C_4$ heteroalkyl, $C_1$–$C_4$ haloalkyl, $C_2$–$C_4$ alkenyl, $C_2$–$C_4$ heteroalkenyl, $C_2$–$C_4$ haloalkenyl, $C_2$–$C_4$ alkynyl and $C_2$–$C_4$ heteroalkynyl, $C_2$–$C_4$ haloalkynyl | |
| $R_{10}$ | H and $C_1$–$C_4$ alkyl | | H and methyl | H |
| $R_{11}$ | H and $C_1$–$C_4$ alkyl | | H and methyl | H |
| n | 0 or 1 | | | |
| X | CH or N | | | N |
| Y | O, S, and $NR^{10}$ | O and S | | S |

In one aspect, the present invention provides a pharmaceutical composition comprising an effective amount of a progesterone receptor modulator compound of formulae I or II shown above wherein $R^1$ through $R^{11}$, n, X, Y, have the same definitions as given above.

In a further aspect, the present invention comprises a method of modulating a process mediated by progesterone receptors comprising administering to a patient having a condition mediated by progesterone receptors an effective amount of a compound of the formulae I or II shown above, wherein $R^1$ through $R^{11}$, n, X, Y, have the same definitions as those given above.

Any of the compounds of the present invention can be synthesized as pharmaceutically acceptable salts for incorporation into various pharmaceutical compositions. As used herein, pharmaceutically acceptable salts include, but are not limited to, hydrochloric, hydrobromic, hydroiodic, hydrofluoric, sulfuric, citric, maleic, acetic, lactic, nicotinic, succinic, oxalic, phosphoric, malonic, salicylic, phenylacetic, stearic, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl)aminomethane. Additional pharmaceutically acceptable salts are known to those skilled in the art.

PR agonist, partial agonist and antagonist compounds of the present invention may be particularly useful for female hormone replacement therapy and as modulators of fertility (e.g., as contraceptives, contragestational agents or abortifacients, in vitro fertilization, pregnancy maintenance), either alone or in conjunction with one or more estrogen receptor modulators. PR modulator compounds of this invention also may be used in the treatment of dysfunctional uterine bleeding, dysmenorrhea, endometriosis, leiomyomas (uterine fibroids), hot flushes, mood disorders, and meningiomas. The PR modulator compounds of this invention also may be used in the treatment of various hormone-dependent cancers, including, without limitation, cancers of ovaries, breast, endometrium and prostate. PR modulator compounds of this invention can also be used in treatment of female osteoporosis, either alone or in combination with one or more estrogen receptor modulators.

It will be understood by those skilled in the art that while the compounds of the present invention will typically be employed as selective agonists, partial agonists or antagonists, that there may be instances where a compound with a mixed steroid receptor profile is preferred. For example, use of a PR agonist (i.e., progestin) in female contraception often leads to the undesired effects of increased water retention and acne flare ups. In this instance, a compound that is primarily a PR agonist, but also displays some AR and MR modulating activities, may prove useful. Specifically, the mixed MR effects would be useful to control water balance in the body, while the AR effects would help to control any acne flare ups that occur.

Furthermore, it will be understood by those skilled in the art that compounds of the present invention, including pharmaceutical compositions and formulations containing these compounds, can be used in a wide variety of combination therapies to treat the conditions and diseases described above. Thus, compounds of the present invention can be used in combination with other hormones and other therapies, including, without limitation, chemotherapeutic agents such as cytostatic and cytotoxic agents, immunological modifiers such as interferons, interleukins, growth hormones and other cytokines, hormone therapies, surgery and radiation therapy.

Representative PR modulator compounds (i.e., agonists, partial agonists and antagonists) according to the present invention include:

7,9-difluoro-5(Z)-benzylidene-1,2-dihydro-2,2,4-trimethyl-5H-chromeno[3,4-f]quinoline (Compound 10);

7,9-difluoro-5(Z)-(2-fluorobenzylidene)-1,2-dihydro-2,2,4-trimethyl-5H-chromeno[3,4-f]quinoline (Compound 12);

7,9-difluoro-5(Z)-(2-chlorobenzylidene)-1,2-dihydro-2,2,4-trimethyl-5H-chromeno[3,4-f]quinoline (Compound 13);

7,9-difluoro-5(Z)-(4-picolylidene)-1,2-dihydro-2,2,4-trimethyl-5H-chromeno[3,4-f]quinoline (Compound 14);

7,9-difluoro-5(Z)-(3-fluorobenzylidene)-1,2-dihydro-2,2,4-trimethyl-5H-chromeno[3,4-f]quinoline (Compound 15);

7,9-difluoro-5(Z)-(4-fluorobenzylidene)-1,2-dihydro-2,2,4-trimethyl-5H-chromeno[3,4-f]quinoline (Compound 16);

7,9-difluoro-5(Z)-(2,5-difluorobenzylidene)-1,2-dihydro-2,2,4-trimethyl-5H-chromeno[3,4-f]quinoline (Compound 17);

7,9-difluoro-5(Z)-(2-methoxybenzylidene)-1,2-dihydro-2,2,4-trimethyl-5H-chromeno[3,4-f]quinoline (Compound 18);

7,9-difluoro-5(Z)-(2-methyl-5-fluorobenzylidene)-1,2-dihydro-2,2,4-trimethyl-5H-chromeno[3,4-f]quinoline (Compound 19);

7,9-difluoro-5(Z)-(3-methyl-4-picolylidene)-1,2-dihydro-2,2,4-trimethyl-5H-chromeno[3,4-f]quinoline (Compound 20);

7,9-difluoro-5(Z)-(2-methyl-3-fluorobenzylidene)-1,2-dihydro-2,2,4-trimethyl-5H-chromeno[3,4-f]quinoline (Compound 21);

7,9-difluoro-5(Z)-(3-methyl-2-picolylidene)-1,2-dihydro-2,2,4-trimethyl-5H-chromeno[3,4-f]quinoline (Compound 22);

7,9-difluoro-5(Z)-(2,3-dimethylbenzylidene)-1,2-dihydro-2,2,4-trimethyl-5H-chromeno[3,4-f]quinoline (Compound 23);

7,9-difluoro-5(Z)-cyanomethylidene-1,2-dihydro-2,2,4-trimethyl-5H-chromeno[3,4-f]quinoline (Compound 24);

7,9-difluoro-5(Z)-hexylidene-1,2-dihydro-2,2,4-trimethyl-5H-chromeno[3,4-f]quinoline (Compound 25);

7,9-difluoro-5(Z)-(2-methoxy-5-fluorobenzylidene)-1,2-dihydro-2,2,4-trimethyl-5H-chromeno[3,4-f]quinoline (Compound 26);

7,9-difluoro-5(Z)-(2,4,5-trifluorobenzylidene)-1,2-dihydro-2,2,4-trimethyl-5H-chromeno[3,4-f]quinoline (Compound 27);

7,9-difluoro-5-methylidene-1,2-dihydro-2,2,4-trimethyl-5H-chromeno[3,4-f]quinoline (Compound 28);

7,9-difluoro-5(Z)-bromomethylidene-1,2-dihydro-2,2,4-trimethyl-5H-chromeno[3,4-f]quinoline (Compound 29);

7,9-difluoro-5(Z)-(3-thienylmethylidene)-1,2-dihydro-2,2,4-trimethyl-5H-chromeno[3,4-f]quinoline (Compound 30);

7,9-difluoro-5(Z)-(2-thienylmethylidene)-1,2-dihydro-2,2,4-trimethyl-5H-chromeno[3,4-f]quinoline (Compound 31);

(±)-7,9-difluoro-5-methoxy-1,2-dihydro-2,2,4-trimethyl-5H-chromeno[3,4-f]quinoline (Compound 32);

(±)-7,9-difluoro-5-phenyl-1,2-dihydro-2,2,4-trimethyl-5H-chromeno[3,4-f]quinoline (Compound 33);
(±)-7,9-difluoro-5-(3-methylphenyl)-1,2-dihydro-2,2,4-trimethyl-5H-chromeno[3,4-f]quinoline (Compound 34);
(±)-7,9-difluoro-5-(1,3-benzodioxol-5-yl)-1,2-dihydro-2,2,4-trimethyl-5H-chromeno[3,4-f]quinoline (Compound 35);
(±)-7,9-difluoro-5-(4-bromophenyl)-1,2-dihydro-2,2,4-trimethyl-5H-chromeno[3,4-f]quinoline (Compound 36);
(±)-7,9-difluoro-5-(4-chloro-3-methylphenyl)-1,2-dihydro-2,2,4-trimethyl-5H-chromeno[3,4-f]quinoline (Compound 37);
(−)-7,9-difluoro-5-(4-chloro-3-methylphenyl)-1,2-dihydro-2,2,4-trimethyl-5H-chromeno[3,4-f]quinoline (Compound 38);
(+)-7,9-difluoro-5-(4-chloro-3-methylphenyl)-1,2-dihydro-2,2,4-trimethyl-5H-chromeno[3,4-f]quinoline (Compound 39);
(±)-7,9-difluoro-5-(3-fluorophenyl)-1,2-dihydro-2,2,4-trimethyl-5H-chromeno[3,4-f]quinoline (Compound 40);
(±)-7,9-difluoro-5-(3-chlorophenyl)-1,2-dihydro-2,2,4-trimethyl-5H-chromeno[3,4-f]quinoline (Compound 41);
(±)-7,9-difluoro-5-(3-bromophenyl)-1,2-dihydro-2,2,4-trimethyl-5H-chromeno[3,4-f]quinoline (Compound 42);
(±)-7,9-difluoro-5-(4-chlorophenyl)-1,2-dihydro-2,2,4-trimethyl-5H-chromeno[3,4-f]quinoline (Compound 43);
(±)-7,9-difluoro-1,2-dihydro-2,2,4,5-tetramethyl-5H-chromeno[3,4-f]quinoline (Compound 44);
(±)-7,9-difluoro-5-(2-oxo-2-phenylethyl)-1,2-dihydro-2,2,4-trimethyl-5H-chromeno[3,4-f]quinoline (Compound 45);
(±)-7,9-difluoro-5-ethyl-1,2-dihydro-2,2,4-trimethyl-5H-chromeno[3,4-f]quinoline (Compound 46);
(±)-7,9-difluoro-5-ethenyl-1,2-dihydro-2,2,4-trimethyl-5H-chromeno[3,4-f]quinoline (Compound 47);
(±)-7,9-difluoro-5-(2-oxo-3-butenyl)-1,2-dihydro-2,2,4-trimethyl-5H-chromeno[3,4-f]quinoline (Compound 48);
Methyl (±)-7,9-difluoro-1,2-dihydro-α,α,2,2,4-pentamethyl-5H-chromeno[3,4-f]quinoline-5-ethanoate (Compound 49);
(±)-7,9-difluoro-5-ethynyl-1,2-dihydro-2,2,4-trimethyl-5H-chromeno[3,4-f]quinoline (Compound 50);
(±)-7,9-difluoro-5-cyano-1,2-dihydro-2,2,4-trimethyl-5H-chromeno[3,4-f]quinoline (Compound 51);
(±)-7,9-difluoro-5-butyl-1,2-dihydro-2,2,4-trimethyl-5H-chromeno[3,4-f]quinoline (Compound 52);
(±)-7,9-difluoro-5-(2-thienyl)-1,2-dihydro-2,2,4-trimethyl-5H-chromeno[3,4-f]quinoline (Compound 53);
(±)-7,9-difluoro-5-(2-furyl)-1,2-dihydro-2,2,4-trimethyl-5H-chromeno[3,4-f]quinoline (Compound 54);
(±)-7,9-difluoro-5-allyl-1,2-dihydro-2,2,4-trimethyl-5H-chromeno[3,4-f]quinoline (Compound 55);
(±)-7,9-difluoro-5-[3-(trifluoromethyl)phenyl]-1,2-dihydro-2,2,4-trimethyl-5H-chromeno[3,4-f]quinoline (Compound 56);
Ethyl (±)-7,9-difluoro-1,2-dihydro-α-methylene-2,2,4-trimethyl-5H-chromeno[3,4-f]quinoline-5-propanoate (Compound 57);
(±)-7,9-difluoro-1,2-dihydro-β-methylene-2,2,4-trimethyl-5H-chromeno[3,4-f]quinoline-5-propanol (Compound 58);
(±)-7,9-difluoro-1,2-dihydro-β-methylene-2,2,4-trimethyl-5H-chromeno[3,4-f]quinoline-5-propanol acetate(Compound 59);
(±)-7,9-difluoro-5-(1-methylethenyl)-1,2-dihydro-2,2,4-trimethyl-5H-chromeno[3,4-f]quinoline (Compound 60);
(±)-7,9-difluoro-5-(N-methyl-2-pyrrolyl)-1,2-dihydro-2,2,4-trimethyl-5H-chromeno[3,4-f]quinoline (Compound 61);
(±)-7,9-difluoro-5-phenylethynyl-1,2-dihydro-2,2,4-trimethyl-5H-chromeno[3,4-f]quinoline (Compound 62);
(±)-7,9-difluoro-5-(benzo[b]thien-2-yl)-1,2-dihydro-2,2,4-trimethyl-5H-chromeno[3,4-f]quinoline (Compound 63);
(−)-7,9-difluoro-5-(benzo[b]thien-2-yl)-1,2-dihydro-2,2,4-trimethyl-5H-chromeno[3,4-f]quinoline (Compound 64);
(+)-7,9-difluoro-5-(benzo[b]thien-2-yl)-1,2-dihydro-2,2,4-trimethyl-5H-chromeno[3,4-f]quinoline (Compound 65);
(±)-7,9-difluoro-5-(5-methyl-2-furyl)-1,2-dihydro-2,2,4-trimethyl-5H-chromeno[3,4-f]quinoline (Compound 66);
(±)-7,9-difluoro-5-(2-benzo[b]furyl)-1,2-dihydro-2,2,4-trimethyl-5H-chromeno[3,4-f]quinoline (Compound 67);
(±)-7,9-difluoro-5-[4-(dimethylamino)phenyl]-1,2-dihydro-2,2,4-trimethyl-5H-chromeno[3,4-f]quinoline (Compound 68);
(±)-7,9-difluoro-5-(5-methyl-2-thienyl)-1,2-dihydro-2,2,4-trimethyl-5H-chromeno[3,4-f]quinoline (Compound 69);
(±)-7,9-difluoro-5-(5-methoxy-2-furyl)-1,2-dihydro-2,2,4-trimethyl-5H-chromeno[3,4-f]quinoline (Compound 70);
(±)-7,9-difluoro-5-(2-propynyl)-1,2-dihydro-2,2,4-trimethyl-5H-chromeno[3,4-f]quinoline (Compound 71);
(−)-7,9-difluoro-5-(2-propynyl)-1,2-dihydro-2,2,4-trimethyl-5H-chromeno[3,4-f]quinoline (Compound 72);
(+)-7,9-difluoro-5-(2-propynyl)-1,2-dihydro-2,2,4-trimethyl-5H-chromeno[3,4-f]quinoline (Compound 73);
(+)-7,9-difluoro-5-(1-propynyl)-1,2-dihydro-2,2,4-trimethyl-5H-chromeno[3,4-f]quinoline (Compound 74);
(−)-7,9-difluoro-5-(1-propynyl)-1,2-dihydro-2,2,4-trimethyl-5H-chromeno[3,4-f]quinoline (Compound 75);
(+)-7,9-difluoro-5-(1-propynyl)-1,2-dihydro-2,2,4-trimethyl-5H-chromeno[3,4-f]quinoline (Compound 76);
(±)-7,9-difluoro-5-(4,5-dimethyl-2-furyl)-1,2-dihydro-2,2,4-trimethyl-5H-chromeno[3,4-f]quinoline (Compound 77);
(±)-7,9-difluoro-5-(2-methyl-1-propenyl)-1,2-dihydro-2,2,4-trimethyl-5H-chromeno[3,4-f]quinoline (Compound 78);
(±)-7,9-difluoro-5-(3,4-dimethyl-2-thienyl)-1,2-dihydro-2,2,4-trimethyl-5H-chromeno[3,4-f]quinoline (Compound 79);
(±)-7,9-difluoro-5-(3-(3-bromophenyl)phenyl)-1,2-dihydro-2,2,4-trimethyl-5H-chromeno[3,4-f]quinoline (Compound 80); and
7,9-difluoro-5(Z)-(2-methylbenzylidene)-1,2-dihydro-2,2,4-trimethyl-5H-chromeno[3,4-f]quinoline (Compound 81).

The sequence of steps for the general schemes to synthesize the compounds of the present invention is shown below. In each of the Schemes the R groups (e.g., $R^8$, $R^9$, etc.) correspond to the specific substitution patterns noted in the Examples. However, it will be understood by those skilled in the art that other functionalities disclosed herein at the indicated positions of compounds of formulae I and II also comprise potential substituents for the analogous positions on the structures within the Schemes. In a further aspect, the present invention contains a novel process for the preparation of the compounds of the present invention.

Scheme I

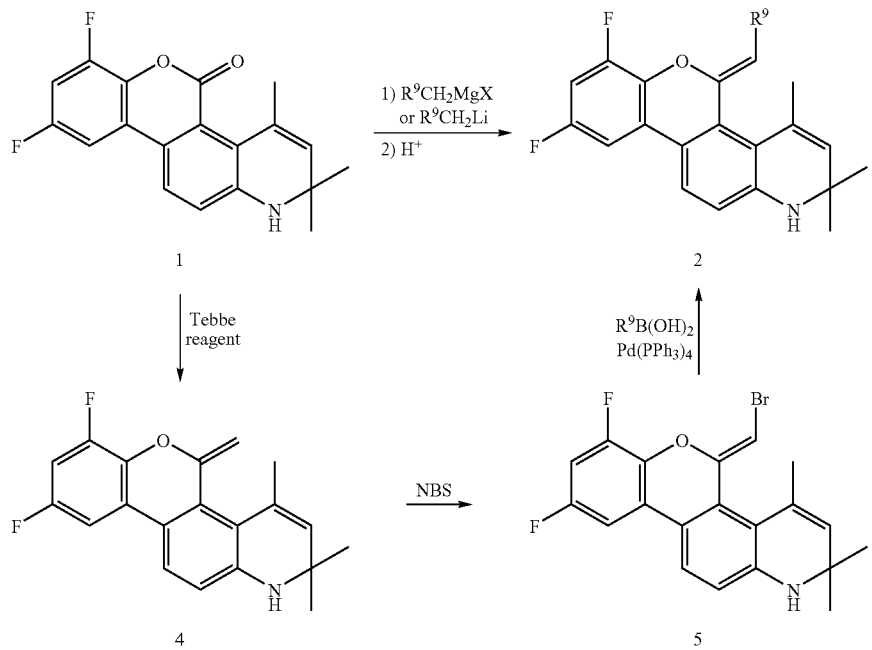

The process of Scheme I begins with addition of organolithium or Grignard reagents to lactones 1 followed by the treatment with a Lewis acid, such as p-toluenesulfonic acid, to produce compounds of structure 2. An alternative route starts with the treatment of lactone 1 with Tebbe reagent to provide compound 4. Bromination with NBS affords the bromomethylidene 5. Palladium catalyzed Suzuki reaction of compound 5 with a boronic acid gives the methylidene derivatives of structure 2.

Scheme II

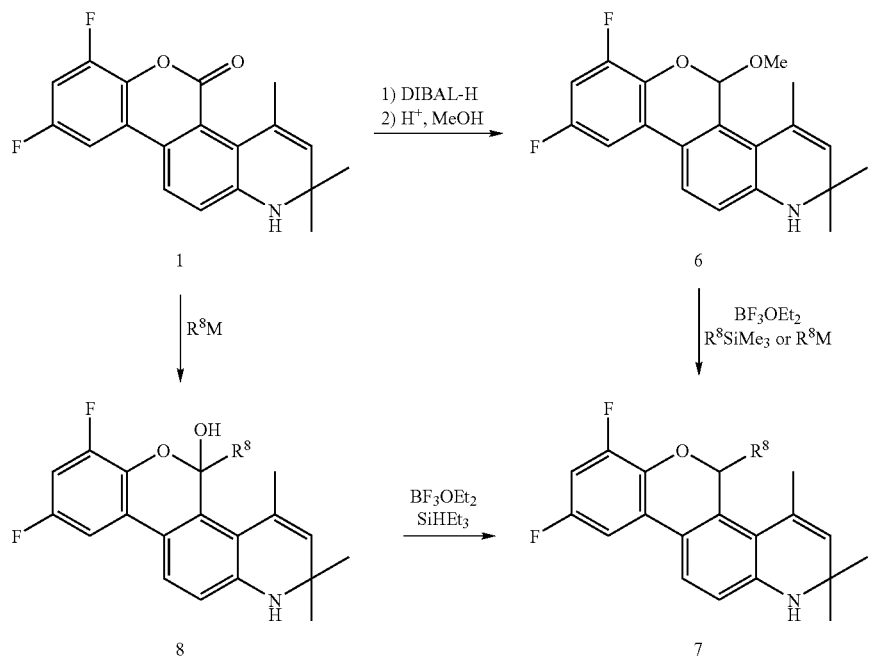

Scheme II describes the synthesis of the 5-alkyl/aryl analogues 7. Reduction of lactone 1 with DIBAL-H followed by acid catalyzed methylation provides lactal intermediates 6. Treatment of the lactal 6 with a nucleophile in the presence of a Lewis acid, such as $BF_3$—$OEt_2$, affords the final products of structure 7. Alternatively, addition of a nucleophile directly to lactone 1 affords hemiacetals 8, which are treated with silane in the presence of a Lewis acid leading to the same products 7.

The compounds of the present invention also include racemates, stereoisomers and mixtures of said compounds, including isotopically-labeled and radio-labeled compounds. Such isomers can be isolated by standard resolution techniques, including fractional crystallization and chiral column chromatography.

As noted above, PR modulator compounds of the present invention can be combined in a mixture with a pharmaceutically acceptable carrier to provide pharmaceutical compositions useful for treating the biological conditions or disorders noted herein in mammalian, and particularly in human patients. The particular carrier employed in these pharmaceutical compositions may take a wide variety of forms depending upon the type of administration desired. Suitable administration routes include enteral (e.g., oral), topical, suppository, inhalable and parenteral (e.g., intravenous, intramuscular and subcutaneous).

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent a desirable oral dosage form for the pharmaceutical compositions of the present invention.

For parenteral administration, the carrier will typically comprise sterile water, although other ingredients that aid in solubility or serve as preservatives, may also be included. Furthermore, injectable suspensions may also be prepared, in which case appropriate liquid carriers, suspending agents and the like will be employed.

For topical administration, the compounds of the present invention may be formulated using bland, moisturizing bases, such as ointments or creams. Examples of suitable ointment bases are petrolatum, petrolatum plus volatile silicones, lanolin and water in oil emulsions such as Eucerin™, available from Beiersdorf (Cincinnati, Ohio). Examples of suitable cream bases are Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Warner-Lambert (Morris Plains, N. J.).

The pharmaceutical compositions and compounds of the present invention will generally be administered in the form of a dosage unit (e.g., tablet, capsule, etc.). The compounds of the present invention generally are administered in a daily dosage of from about 1 μg/kg of body weight to about 50 mg/kg of body weight. Typically, the compounds of the present invention are administered in a daily dosage of from about 2 μg/kg to about 25 mg/kg of body weight. Preferably, the compounds of the present invention are administered in a daily dosage of from about 10 μg/kg to about 5 mg/kg body weight. As recognized by those skilled in the art, the particular quantity of pharmaceutical composition according to the present invention administered to a patient will depend upon a number of factors, including, without limitation, the biological activity desired, the condition of the patient, and tolerance for the drug.

Compounds of this invention also have utility when radio- or isotopically-labeled as ligands for use in assays to determine the presence of PR in a cell background or extract. Such compounds are particularly useful due to their ability to selectively activate progesterone receptors, and can therefore be used to determine the presence of such receptors in the presence of other steroid receptors or related intracellular receptors.

Compounds and pharmaceutical compositions of the present invention may be extremely potent activators of PR. For example, compounds and compositions of the present invention may display 50% maximal activation of PR at a concentration of less than 50 nM. Some compounds and compositions of the present invention may display 50% maximal activation of PR at a concentration of less than 20 nM, and some may display such activity at a concentration of 10 nM or less. In addition, the compounds of the present invention may be tissue-selective modulators. For example, the compounds of this invention may suppress estrogen-induced endometrial stimulation in uterus equally efficacious as marketed steroidal modulator compounds but display reduced proliferative activity or antagonized endogenous hormone induced proliferative activity in breasts.

The invention will be further illustrated by reference to the following non-limiting Examples.

EXAMPLE 1

Preparation of 7,9-difluoro-5(Z)-benzylidene-1,2-dihydro-2,2,4-trimethyl-5H-chromeno[3,4-f]quinoline (Compound 10, Structure 2 of Scheme I, where $R^9$=phenyl)

General procedure I for preparing 5(Z)-substituted methylidene compounds (Structure 2 of Scheme I) from lactones (Structure 1 of Scheme I) and a Grignard or organolithium reagent. To a solution (0.2–1.0 M) of lactone 1 in THF was added a freshly prepared Grignard or organolithium solution (3–5 equiv.). The reaction mixture was stirred for 1–12 h until the starting material was consumed and then was poured into ice-cold 50% $NH_4Cl$ and extracted with EtOAc (2×). The extracts were washed with brine (3×), dried ($Na_2SO_4$) and concentrated. A solution (0.2–0.5 M) of the crude lactol intermediate in $CH_2Cl_2$ was treated with a catalytic amount of p-toluenesulfonic acid at room temperature for 3 h, quenched with saturated $NaHCO_3$ and extracted with EtOAc (2×). The extracts were washed with brine (3×), dried ($Na_2SO_4$), and concentrated. Flash chromatography (silica gel, EtOAc-hexane 2% to 10% gradient) of the crude mixture afforded the final product in good yield. To prevent photoisomerization of the benzylidene analogues, the dehydration step and the work-up should be carried out in a light-controlled environment.

Compound 10 was prepared from benzyl Grignard and 7,9-difluoro-1,2-dihydro-2,2,4-trimethyl-5-coumarino[3,4-f]quinoline (Compound 11, structure 1 of Scheme I) according to the general procedure as a yellow solid: $^1$H-NMR (400 MHz, $CDCl_3$) 7.84 (d, J=7.9, 2H), 7.40–7.36 (m, 4H), 7.20–7.14 (m, 1H), 6.76–6.71 (m, 1H), 6.66 (d, J=8.4, 1H), 5.67 (s, 1H), 5.54 (s, 1H), 4.24 (bs, 1H), 2.18 (s, 3H), 1.35 (bs, 6H).

EXAMPLE 2

Preparation of 7,9-difluoro-5(Z)-(2-fluorobenzylidene)-1,2-dihydro-2,2,4-trimethyl-5H-chromeno[3,4-f]quinoline (Compound 12, Structure 2 of Scheme I, where $R^9$=2-fluorophenyl)

This compound was prepared in a similar fashion as that described in Example 1 from 2-fluorobenzyl Grignard reagent and Compound 11 (Structure 1 of Scheme I,) as a yellow solid: $^1$H-NMR (400 MHz, CDCl$_3$) 8.44–8.38 (m, 1H), 7.39 (d, J=8.4, 1H), 7.23–7.14 (m, 3H), 7.06–7.00 (m, 1H), 6.76–6.70 (m, 1H), 6.67 (d, J=8.4, 1H), 6.00 (s, 1H), 5.56 (s, 1H), 4.25 (bs, 1H), 2.12 (s, 3H), 1.35 (bs, 6H).

EXAMPLE 3

Preparation of 7,9-difluoro-5(Z)-(2-chlorobenzylidene)-1,2-dihydro-2,2,4-trimethyl-5H-chromeno[3,4-f]quinoline (Compound 13, Structure 2 of Scheme I, where $R^9$=2-chlorophenyl)

This compound was prepared in a similar fashion as that described in Example 1 from 2-chlorobenzyl Grignard reagent and Compound 11 (Structure 1 of Scheme I) as a yellow solid: $^1$H-NMR (400 MHz, CDCl$_3$) 8.45 (d, J=8.0, 1H), 7.39 (d, J=8.5, 1H), 7.36–7.30 (m, 2H), 7.18–7.13 (m, 2H), 6.73–6.70 (m, 1H), 6.69 (d, J=8.5, 1H), 6.25 (s, 1H), 5.56 (s, 1H), 4.27 (bs, 1H), 2.13 (s, 3H), 1.35 (bs, 6H).

EXAMPLE 4

Preparation of 7,9-difluoro-5(Z)-(4-picolylidene)-1,2-dihydro-2,2,4-trimethyl-5H-chromeno[3,4-f]quinoline (Compound 14, Structure 2 of Scheme I, where $R^9$=4-pyridyl)

This compound was prepared in a similar fashion as that described in Example 1 from 4-picolyl lithium and Compound 11 (Structure 1 of Scheme I) as a yellow solid: $^1$H-NMR (400 MHz, CDCl$_3$) 8.59 (d, J=5.8, 2H), 7.69 (d, J=5.1, 2H), 7.44 (d, J=8.5, 1H), 7.20–7.18 (m, 1H), 6.81–6.79 (m, 1H), 6.73 (d, J=8.5, 1H), 5.63 (s, 1H), 5.58 (s, 1H), 4.31 (bs, 1H), 2.09 (d, J=1.2, 3H), 1.37 (bs, 6H).

EXAMPLE 5

Preparation of 7,9-difluoro-5(Z)-(3-fluorobenzylidene)-1,2-dihydro-2,2,4-trimethyl-5H-chromeno[3,4-f]quinoline (Compound 15, Structure 2 of Scheme I, where $R^9$=3-fluorophenyl)

This compound was prepared in a similar fashion as that described in Example 1 from 3-fluorobenzyl Grignard reagent and Compound 11 (Structure 1 of Scheme I) as a yellow solid: $^1$H-NMR (400 MHz, Acetone-d$_6$) 7.82–7.79 (ddd, J=2.0, 2.0, 9.5, 1H), 7.66 (d, J=8.5, 1H), 7.52–7.38 (m, 3H), 7.05–6.97 (m, 2H), 6.87 (d, J=8.5, 1H), 6.10 (bs, 1H), 5.79 (s, 1H), 5.58 (s, 1H), 2.08 (s, 3H), 1.40 (bs, 6H).

EXAMPLE 6

Preparation of 7,9-difluoro-5(Z)-(4-fluorobenzylidene)-1,2-dihydro-2,2,4-trimethyl-5H-chromeno[3,4-f]quinoline (Compound 16, Structure 2 of Scheme I, where $R^9$=4-fluorophenyl)

This compound was prepared in a similar fashion as that described in Example 1 from 4-fluorobenzyl Grignard reagent and Compound 11 (Structure 1 of Scheme I) as a yellow solid: $^1$H-NMR (400 MHz, Acetone-d$_6$) 7.92–7.88 (dd, J=5.6, 8.9, 2H), 7.64 (d, J=8.5, 1H), 7.46–7.42 (ddd, J=2.1, 2.1, 9.5, 1H), 7.19–7.14 (dd, J=8.7, 8.7, 2H), 6.98–6.96 (m, 1H), 6.84 (d, J=8.5, 1H), 6.07 (bs, 1H), 5.76 (s, 1H), 5.57 (s, 1H), 2.08 (s, 3H), 1.31 (bs, 6H).

EXAMPLE 7

Preparation of 7,9-difluoro-5(Z)-(2,5-difluorobenzylidene)-1,2-dihydro-2,2,4-trimethyl-5H-chromeno[3,4-f]quinoline (Compound 17, Structure 2 of Scheme I, where $R^9$=2,5-difluorophenyl)

This compound was prepared in a similar fashion as that described in Example 1 from 2,5-difluorobenzyl Grignard reagent and Compound 11 (Structure 1 of Scheme I) as a yellow solid: $^1$H-NMR (400 MHz, Acetone-d$_6$) 8.26–8.21 (m, 1H), 7.69 (d, J=8.5, 1H), 7.51–7.47 (ddd, J=2.4, 2.4, 9.9, 1H), 7.22–7.16 (ddd, J=4.7, 9.3, 9.3, 1H), 7.09–7.00 (m, 2H), 6.90 (d, J=8.4, 1H), 6.16 (bs, 1H), 6.03 (s, 1H), 5.59 (s, 1H), 2.10 (s, 3H), 1.30 (bs, 6H).

EXAMPLE 8

Preparation of 7,9-difluoro-5(Z)-(2-methoxybenzylidene)-1,2-dihydro-2,2,4-trimethyl-5H-chromeno[3,4-f]quinoline (Compound 18, Structure 2 of Scheme I, where $R^9$=2-methoxyphenyl)

This compound was prepared in a similar fashion as that described in Example 1 from 2-methoxybenzyl Grignard reagent and Compound 11 (Structure 1 of Scheme I) as a yellow solid: $^1$H-NMR (400 MHz, Acetone-d$_6$) 8.31–8.28 (dd, J=1.6, 7.8, 1H), 7.61 (d, J=8.5, 1H), 7.44–7.41 (ddd, J=2.0, 2.0, 9.9, 1H), 7.26–7.22 (ddd, J=1.7, 7.5, 7.5, 1H), 7.04–6.90 (m, 3H), 6.82 (d, J=8.5, 1H), 6.26 (s, 1H), 6.12 (bs, 1H), 5.55 (s, 1H), 3.80 (s, 3H), 2.11 (s, 3H), 1.33 (bs, 6H).

EXAMPLE 9

Preparation of 7,9-difluoro-5(Z)-(2-methyl-5-fluorobenzalidene)-1,2-dihydro-2,2,4-trimethyl-5H-chromeno[3,4-f]quinoline (Compound 19, Structure 2 of Scheme I, where $R^9$=2-methyl-5-fluorophenyl)

This compound was prepared in a similar fashion as that described in Example 1 from 2-methyl-5-fluorobenzyl Grignard reagent and Compound 11 (Structure 1 of Scheme I) as a yellow solid: $^1$H-NMR (400 MHz, Acetone-d$_6$) 8.14–8.11 (dd, J=2.7, 14.2, 1H), 7.66 (d. J=8.5, 1H), 7.46 (ddd, J=2.2, 2.2, 9.9, 1H), 7.24–7.21 (dd, J=6.3, 8.2, 1H), 7.01–6.96 (ddd, J=3.0, 8.6, 10.4, 1H), 6.94–6.90 (ddd, J=2.8, 8.4, 8.4, 1H), 6.88 (d, J=8.5, 1H), 6.12 (s, 1H), 6.03 (s, 1H), 5.59 (s, 1H), 2.27 (s, 3H), 2.12 (s, 3H), 1.34 (bs, 6H).

EXAMPLE 10

Preparation of 7,9-difluoro-5(Z)-(3-methyl-4-picolylidene)-1,2-dihydro-2,2,4-trimethyl-5H-chromeno[3,4-f]quinoline (Compound 20, Structure 2 of Scheme I, where $R^9$=3-methyl-4-pyridyl)

This compound was prepared in a similar fashion as that described in Example 1 from 3-methyl-4-picolyl lithium and Compound 11 (Structure 1 of Scheme I) as a yellow solid: $^1$H-NMR (500 MHz, CDCl$_3$) 8.49 (d, J=4.9, 1H), 8.39 (s, 1H), 8.19 (d, J=5.5, 1H), 7.43 (d, J=8.5, 1H), 7.17 (ddd, J=9.5, 2.4, 2.1, 1H), 6.77 (ddd, J=10.1, 8.5, 3.1, 1H), 6.73 (d, J=8.5, 1H), 5.92 (s, 1H), 5.56 (s, 1H), 4.31 (bs, 1H), 2.24 (s, 3H), 2.12 (d, J=1.2, 3H), 1.38 (bs, 6H).

EXAMPLE 11

Preparation of 7,9-difluoro-5(Z)-(2-methyl-3-fluorobenzylidene)-1,2-dihydro-2,2,4-trimethyl-5H-chromeno[3,4-f]quinoline (Compound 21, Structure 2 of Scheme I, where $R^9$=2-methyl-3-fluorophenyl)

This compound was prepared in a similar fashion as that described in Example 1 from 2-methyl-3-fluorobenzyl Grignard reagent and Compound 11 (Structure 1 of Scheme I) as a yellow solid: $^1$H-NMR (400 MHz, Acetone-$d_6$) 8.06 (d, J=7.8, 1H), 7.66 (d, J=8.5, 1H), 7.47–7.43 (ddd, J=2.2, 2.2, 9.9, 1H), 7.31–7.26 (dd, J=7.9, 14.0, 1H), 7.01–6.93 (m, 2H), 6.87 (d, J=8.5, 1H), 6.11 (bs, 1H), 6.02 (s, 1H), 5.59 (s, 1H), 2.20 (s, 3H), 2.13 (s, 3H), 1.33 (bs, 6H).

EXAMPLE 12

Preparation of 7,9-difluoro-5(Z)-(3-methyl-2-picolylidene)-1,2-dihydro-2,2,4-trimethyl-5H-chromeno[3,4-f]quinoline (Compound 22, Structure 2 of Scheme I, where $R^9$=3-methyl-2-pyridyl)

This compound was prepared in a similar fashion as that described in Example 1 from 3-methyl-2-picolyl lithium and Compound 11 (Structure 1 of Scheme I) as a yellow solid: $^1$H-NMR (500 MHz, CDCl$_3$) 8.50 (dd, J=4.6, 1.5, 1H), 7.50 (dd, J=7.6, 1.5, 1H), 7.40 (d, J=8.5, 1H), 7.15–7.12 (m, 1H), 7.07 (dd, J=7.6, 4.6, 1H), 6.69 (d, J=8.5, 1H), 6.66 (ddd, J=10.2, 8.2, 2.7, 1H), 6.01 (s, 1H), 5.53 (d, J=1.2, 1H), 4.26 (bs, 1H), 2.38 (s, 3H), 2.26 (d, J=1.2, 3H), 1.33 (bs, 6H).

EXAMPLE 13

Preparation of 7,9-difluoro-5(Z)-(2,3-dimethylbenzylidene)-1,2-dihydro-2,2,4-trimethyl-5H-chromeno[3,4-f]quinoline (Compound 23, Structure 2 of Scheme I, where $R^9$=2,3-dimethylphenyl)

This compound was prepared in a similar fashion as that described in Example 1 from 2,3-dimethylbenzyl Grignard reagent and Compound 11 (Structure 1 of Scheme I) as a yellow solid: $^1$H-NMR (400 MHz, Acetone-$d_6$) 7.97 (d, J=7.7, 1H), 7.63 (d, J=8.5, 1H), 7.44–7.41 (ddd, J=2.2, 2.2, 10.1, 1H), 7.16–7.13 (dd, J=7.6, 7.6, 1H), 7.07 (d, J=7.3, 1H), 6.94–6.89 (ddd, J=2.9, 8.9, 11.0, 1H), 6.84 (d, J=8.5, 1H), 6.07 (bs, 1H), 6.05 (s, 1H), 5.70 (s, 1H), 2.28 (s, 3H), 2.14 (s, 3H), 2.06 (s, 3H), 1.30 (bs, 6H).

EXAMPLE 14

Preparation of 7,9-difluoro-5(Z)-cyanomethylidene-1,2-dihydro-2,2,4-trimethyl-5H-chromeno[3,4-f]quinoline (Compound 24, Structure 2 of Scheme I, where $R^9$=cyano)

This compound was prepared in a similar fashion as that described in Example 1 from acetonitrile lithium and Compound 11 (Structure 1 of Scheme I) as a yellow solid: $^1$H NMR (500 MHz, CDCl$_3$) 7.50 (d, J=8.6, 1H), 7.24–7.19 (m, 1H), 6.87–6.81 (m, 1H), 6.83 (d, J=8.6, 1H), 5.58 (s, 1H), 4.76 (s, 1H), 4.40 (s, 1H), 2.11 (d, J=1.2, 3H), 1.57 (bs, 6H).

EXAMPLE 15

Preparation of 7,9-difluoro-5(Z)-hexylidene-1,2-dihydro-2,2,4-trimethyl-5H-chromeno[3,4-f]quinoline (Compound 25, Structure 2 of Scheme I, where $R^9$=pentyl)

This compound was prepared in a similar fashion as that described in Example 1 from n-hexyl lithium and Compound 11 (Structure 1 of Scheme I) as a yellow solid: $^1$H-NMR (500 MHz, CDCl$_3$) 7.32 (d, J=8.2, 1H), 7.10 (ddd, J=9.8, 2.7, 1.8, 1H), 6.69 (ddd, J=10.4, 8.5, 2.7, 1H), 6.59 (d, J=8.5, 1H), 5.49 (s, 1H), 4.86 (t, J=7.9, 1H), 4.15 (bs, 1H), 2.35–2.27 (m, 2H), 2.08 (d, J=1.2, 3H), 1.74–1.64 (m, 4H), 1.63–1.58 (m, 1H), 1.36–1.25 (m, 8H), 1.20–1.13 (m, 4H), 1.00–1.93 (m, 2H).

EXAMPLE 16

Preparation of 7,9-difluoro-5(Z)-(2-methoxy-5-fluorobenzylidene)-1,2-dihydro-2,2,4-trimethyl-5H-chromeno[3,4-f]quinoline (Compound 26, Structure 2 of Scheme I, where $R^9$=2-methoxy-5-fluorophenyl)

This compound was prepared in a similar fashion as that described in Example 1 from 2-methoxy-5-fluorobenzyl Grignard reagent and Compound 11 (Structure 1 of Scheme I) as a yellow solid: $^1$H-NMR (400 MHz, Acetone-$d_6$) 8.15–8.12 (ddd, J=1.6, 1.6, 10.6, 1H), 7.63 (d, J=8.5, 1H), 7.46–7.43 (ddd, J=2.2, 2.2, 10.2, 1H), 7.00–6.95 (m, 3H), 6.86–6.84 (d, J=8.4, 1H), 6.27 (s, 1H), 6.06 (bs, 1H), 5.56 (s, 1H), 3.81 (s, 3H), 2.09 (s, 3H), 1.19 (bs, 6H).

EXAMPLE 17

Preparation of 7,9-difluoro-5(Z)-(2,4,5-trifluorobenzylidene)-1,2-dihydro-2,2,4-trimethyl-5H-chromeno[3,4-f]quinoline (Compound 27, Structure 2 of Scheme I, where $R^9$=2,4,5-trifluorophenyl)

This compound was prepared in a similar fashion as that described in Example 1 from 2,4,5-trifluorobenzyl Grignard reagent and Compound 11 (Structure 1 of Scheme I) as a yellow solid: $^1$H-NMR (500 MHz, CDCl$_3$) 8.38–8.32 (m, 1H), 7.41 (d, J=8.2, 1H), 7.18–7.16 (m, 1H), 6.93–6.87 (m, 1H), 6.79–6.75 (m, 1H), 6.69 (d, J=8.2, 1H), 5.88 (s, 1H), 5.56 (s, 1H), 4.28 (bs, 1H), 2.08 (s, 3H), 1.34 (bs, 6H).

EXAMPLE 18

Preparation of 7,9-difluoro-5-methylidene-1,2-dihydro-2,2,4-trimethyl-5H-chromeno[3,4-f]quinoline (Compound 28, Structure 4 of Scheme I)

Treatment of Compound 11 (Structure 1 of Scheme I, where $R^6$=methyl) with Tebbe reagent (0.5 M in toluene) afforded compound 28 as a yellow solid: $^1$H-NMR (500 MHz, CDCl$_3$) 7.35 (d, J=8.2, 1H), 7.13 (ddd, J=9.8, 2.4, 2.1, 1H), 6.71 (ddd, J=10.1, 8.5, 2.8, 1H), 6.65 (d, J=8.2, 1H), 5.51 (d, J=0.9, 1H), 5.19 (d, J=1.5, 1H), 4.52 (d, J=1.5, 1H), 4.20 (bs, 1H), 2.14 (d, J=1.2, 3H), 1.30 (bs, 6H).

EXAMPLE 19

Preparation of 7,9-difluoro-5(Z)-bromomethylidene-1,2-dihydro-2,2,4-trimethyl-5H-chromeno[3,4-f]quinoline (Compound 29, Structure 5 of Scheme I)

Treatment of Compound 28 (Structure 4 of Scheme I) with NBS in DMF at rt for 10 min and standard work-up followed by chromatography provided compound 29 as a yellow foam: $^1$H-NMR (500 MHz, CDCl$_3$) 7.38 (d, J=8.2, 1H), 7.15–7.11 (m, 1H), 6.75 (ddd, J=10.1, 8.2, 2.7, 1H), 6.67 (d, J=8.2, 1H), 5.54 (s, 1H), 5.53 (s, 1H), 4.24 (bs, 1H), 2.08 (d, J=1.5, 3H), 1.30 (bs, 6H).

EXAMPLE 20

Preparation of 7,9-difluoro-5(Z)-(3-thienylmethylidene)-1,2-dihydro-2,2,4-trimethyl-5H-chromeno[3,4-f]quinoline (Compound 30, Structure 2 of Scheme I, $R^9$=3-thiophene)

To a solution of compound 29 (Structure 5 of Scheme I) in DME was added Pd(PPh$_3$)$_4$ (3 mol %) and the mixture was stirred at rt for 15 min. A solution of 3-thiopheneboronic acid in DME and CsF were added to the reaction mixture. The reaction was heated at 80° C. for 2 h, quenched with NaHCO$_3$ (sat'd aqueous) and extracted with EtOAc. Removal of solvent and chromatography of the crude mixture afforded 30 as yellow foam: $^1$H-NMR (500 MHz, CDCl$_3$) 7.77 (d, J=2.4, 1H), 7.54 (d, J=4.0, 1H), 7.37 (d, J=8.2, 1H), 7.32 (dd, J=4.9, 3.1, 1H), 7.17–7.13 (m, 1H), 6.76–6.72 (m, 1H), 6.65 (d, J=8.2, 1H), 5.76 (s, 1H), 5.54 (s, 1H), 4.23 (bs, 1H), 2.09 (d, J=0.9, 3H), 1.34 (bs, 6H).

EXAMPLE 21

Preparation of 7,9-difluoro-5(Z)-(2-thienylmethylidene)-1,2-dihydro-2,2,4-trimethyl-5H-chromeno[3,4-f]quinoline (Compound 31, Structure 2 of Scheme I, $R^9$=2-thiophene)

This compound was prepared in a similar fashion as that described in Example 20 from compound 29 (Structure 5 of Scheme I) and 2-thiopheneboronic acid as yellow foam: $^1$H-NMR (500 MHz, CDCl$_3$) 7.39 (d, J=8.5, 1H), 7.33 (d, J=4.9, 1H), 7.23 (d, J=3.7, 1H), 7.16–7.13 (m, 1H), 7.05 (dd, J=5.2, 3.7, 1H), 6.78–6.74 (m, 1H), 6.65 (d, J=8.2, 1H), 5.99 (s, 1H), 5.56 (s, 1H), 4.25 (bs, 1H), 2.09 (d, J=0.9, 3H), 1.36 (bs, 6H).

EXAMPLE 22

Preparation of (±)-7,9-difluoro-5-methoxy-1,2-dihydro-2,2,4-trimethyl-5H-chromeno[3,4-f]quinoline (Compound 32, Structure 6 of Scheme II)

Reduction of Compound 11 (Structure 1 of Scheme II) with DIBAL-H in toluene at −78° C. for 1 h provided a lactal intermediate, which, upon treatment with TsOH in methanol, afforded Compound 32 as a white solid: $^1$H NMR (500 MHz, CDCl$_3$) 7.39 (d, J=8.6, 1H), 7.21 (dt, J=8.8, 2.4, 1H), 6.75 (td, J=9.3, 2.7, 1H), 6.60 (d, J=8.2, 1H), 6.40 (s, 1H), 5.53 (d, J=1.5, 1H), 4.04 (s, 1H), 3.49 (s, 3H), 2.27 (d, J=1.2, 3H), 1.34 (s, 3H), 1.20 (s, 3H).

EXAMPLE 23

Preparation of (±)-7,9-difluoro-5-phenyl-1,2-dihydro-2,2,4-trimethyl-5H-chromeno[3,4-f]quinoline (Compound 33, Structure 7 of Scheme II, where $R^8$=phenyl)

This compound was prepared by the following general procedure:
To a stirred solution of bromobenzene in THF at −78° C. under nitrogen atmosphere was added n-BuLi in hexanes (1.6 M). After one hour a solution of compound 11 (structure 1 of Scheme II) in THF was added dropwise and after 2 hours at −78° C. the temperature was allowed to rise to −55° C. The reaction mixture was stirred for an additional hour at this temperature, poured into an aqueous ammonium chloride solution and extracted twice with ethyl acetate. The organic extracts were washed with brine, combined, dried (Na$_2$SO$_4$), concentrated and purified using column chromatography on silica gel (heptanes/ethyl acetate: gradient 20/1 to 10/1) to give structure 8 of Scheme II ($R^8$=Phenyl) as an oil. This oil was dissolved in dichloromethane, and 0.2 mL of triethylsilane and 0.17 mL of boron trifluoride diethyl etherate were added. After stirring for 6 hours a saturated solution of sodium hydrogencarbonate was added and extracted three times with dichloromethane. The organic extracts were combined, dried (Na$_2$SO$_4$) and concentrated. Purification using HPLC (LUNA C18(2), CH$_3$CN/water, gradient 6/4 to 10/0) yielded compound 33 as a solid: $^1$H NMR (400 MHz, DMF-d$_7$) 7.70 (d, J=8.8, 1H), 7.40 (dq, J=10, 1.8, 1H), 7.30 (M, 5H), 7.10 (s, 1H), 6.93 (d, J=8.8, 1H), 6.92 (M, 1H), 6.54 (d, J=1.6, 1H), 5.52 (t, J=1.6, 1H), 2.30 (d, J=1.2, 3H), 1.30 (s, 3H), 1.27 (s, 3H).

EXAMPLE 24

Preparation of (±)-7,9-difluoro-5-(3-methylphenyl)-1,2-dihydro-2,2,4-trimethyl-5H-chromeno[3,4-f]quinoline (Compound 34, Structure 7 of Scheme II, where $R^8$=3-methylbenzene)

Compound 34 was prepared in a similar fashion as that described in Example 23 from Compound 11 (Structure 1 of Scheme II) and 3-bromotoluene as a solid: $^1$H NMR (400 MHz, DMF-d$_7$) 7.85 (d, J=8.6, 1H), 7.56 (dq, J=10, 1.8, 1H), 7.37 (t, J=7.6, 1H), 7.30 (s, 1H), 7.25 (d, J=7.8, 1H), 7.23 (s, 1H), 7.21 (d, J=8, 1H), 7.09 (d, J=8.8, 1H), 7.09 (M, 1H), 6.70 (s, 1H), 5.69 (t, J=1.6, 1H), 2.41 (s, 3H), 2.21 (s, 3H), 1.46 (s, 3H), 1.44 (s, 3H).

EXAMPLE 25

Preparation of (±)-7,9-difluoro-5-(1,3-benzodioxol-5-yl)-1,2-dihydro-2,2,4-trimethyl-5H-chromeno[3,4-f]quinoline (Compound 35, Structure 7 of Scheme II, where $R^8$=5-(1,3-benzodioxole))

Compound 35 was prepared in a similar fashion as that described in Example 23 from Compound 11 (Structure 1 of Scheme II) and 5-bromo[1,3]benzodioxole as a solid: $^1$H NMR (400 MHz, DMF-d$_7$) 7.85 (d, J=8.6, 1H), 7.75 (dq, J=10, 1.8, 1H), 7.16 (s, 1H), 7.10 (m, 1H), 7.08 d, J=8.8, 1H), 7.04 (d, J=1.6, 1H), 6.96 (d, J=8.8, 1H), 6.8 (dd, J=8.2, 1.8, 1H), 6.69 (d, J=1.8, 1H), 6.21 (s, 2H), 5.68 (t, J=1.6, 1H), 2.22 (s, 3H), 1.45 (s, 3H), 1.42 (s, 3H).

EXAMPLE 26

Preparation of (±)-7,9-difluoro-5-(4-bromophenyl)-1,2-dihydro-2,2,4-trimethyl-5H-chromeno[3,4-f]quinoline (Compound 36, Structure 7 of Scheme II, where $R^8$=4-bromobenzene)

Compound 36 was prepared in a similar fashion as that described in Example 23 from Compound 11 (Structure 1 of Scheme II) and 1,4-dibromobenzene as a solid: $^1$H NMR (500 MHz, CDCl$_3$) 7.38 (d, J=8.4, 1H), 7.33 (m, 2H), 7.1 (m, 2H), 6.99 (dq, J=9.6, 2, 1H), 6.91 (s, 1H), 6.69 (d, J=8.8, 1H), 6.56 (m, 1H), 5.48 (s, 1H), 4.06 (s, 1H), 1.97 (s, 1H), 1.30 (s, 3H), 1.26 (s, 3H).

EXAMPLE 27

Preparation of (±)-7,9-difluoro-5-(4-chloro-3-methylphenyl)-1,2-dihydro-2,2,4-trimethyl-5H-chromeno[3,4-f]quinoline (Compound 37, Structure 7 of Scheme II, where, $R^8$=4-chloro-3-methylbenzene)

Compound 37 was prepared in a similar fashion as that described in Example 23 from Compound 11 (Structure 1 of Scheme II) and 5-bromo-2-chlorotoluene as a solid: $^1$H NMR (500 MHz CDCl$_3$) 7.38 (d, J=8.4, 1H), 7.15 (d, 8.8, 1H), 7.09 (d, J=2, 1H), 6.98 (m, 2H), 6.90 (s, 1H), 6.70 (d, J=8.8, 1H), 6.57 (m, 1H), 5.49 (s, 1H), 4.06 (s, 1H), 2.24 (s, 1H), 1.98 (s, 3H), 1.30 (s, 3H), 1.27 (s, 3H).

EXAMPLE 28

Preparation of (−)-7,9-difluoro-5-(4-chloro-3-methylphenyl)-1,2-dihydro-2,2,4-trimethyl-5H-chromeno[3,4-f]quinoline and (+)-7,9-difluoro-5-(4-chloro-3-methylphenyl)-1,2-dihydro-2,2,4-trimethyl-5H-chromeno[3,4-f]quinoline (Compounds 38 and 39, Structure 7 of Scheme II, where $R^8$=4-chloro-3-methylbenzene)

These compounds were isolated as enantiomers of Compound 37 by a chiral HPLC separation. Retention times: OJ column 0.46 cm×25 cm, flow 1 ml/min, heptanes/ethanol 85/15; Rt=12 min and 15 min. Compound 38 is the (−)-isomer: $^1$H NMR (500 MHz CDCl$_3$) 7.38 (d, J=8.4, 1H), 7.15 (d, 8.8, 1H), 7.09 (d, J=2, 1H), 6.98 (m, 2H), 6.90 (s, 1H), 6.70 (d, J=8.8, 1H), 6.57 (m, 1H), 5.49 (s, 1H), 4.06 (s, 1H), 2.24 (s, 1H), 1.98 (s, 3H), 1.30 (s, 3H), 1.27 (s, 3H); Compound 39 is the (+)-isomer: $^1$H NMR (500 MHz CDCl$_3$) 7.38 (d, J=8.4, 1H), 7.15 (d, 8.8, 1H), 7.09 (d, J=2, 1H), 6.98 (m, 2H), 6.90 (s, 1H), 6.70 (d, J=8.8, 1H), 6.57 (m, 1H), 5.49 (s, 1H), 4.06 (s, 1H), 2.24 (s, 1H), 1.98 (s, 3H), 1.30 (s, 3H), 1.27 (s, 3H).

EXAMPLE 29

Preparation of (±)-7,9-difluoro-5-(3-fluorophenyl)-1,2-dihydro-2,2,4-trimethyl-5H-chromeno[3,4-f]quinoline (Compound 40, Structure 7 of Scheme II, where $R^8$=3-fluorobenzene)

Compound 40 was prepared in a similar fashion as that described in Example 23 from Compound 11 (Structure 1 of Scheme II) and 3-bromofluorobenzene as a solid: $^1$H NMR (500 MHz, CDCl$_3$) 7.38 (d, J=8.4, 1H), 7.18 (m, 1H), 7.05 (d, J=8.2, 1H), 7.0 (dq, J=10, 2, 1H), 6.95 (s, 1H), 6.89 (m, 2H), 6.70 (d, J=8.6, 1H), 6.57 (m, 1H), 5.49 (d, J=1.4, 1H), 4.06 (s, 1H), 1.99 (s, 3H), 1.31 (s, 3H), 1.27 (s, 3H).

EXAMPLE 30

Preparation of (±)-7,9-difluoro-5-(3-chlorophenyl)-1,2-dihydro-2,2,4-trimethyl-5H-chromeno[3,4-f]quinoline (Compound 41, Structure 7 of Scheme II, where $R^8$=3-chlorobenzene)

Compound 41 was prepared in a similar fashion as that described in Example 23 from Compound 11 (Structure 1 of Scheme II) and 3-bromochlorobenzene as a solid: $^1$H NMR (500 MHz, DMSO-d$_6$) 7.59 (d, J=8.8, 1H), 7.36 (dq, J=10.4, 1.8, 1H), 7.31 (m, 2H), 7.14 (s, 1H), 7.10 (m, 1H), 7.0 (s, 1H), 6.96 (m, 1H), 6.79 (d, J=8.8, 1H), 6.57 (d, J=2, 1H), 5.44 (t, J=1.6, 1H), 1.90 (d, J=1.4, 3H), 1.22 (s, 3H), 1.19 (s, 3H).

EXAMPLE 31

Preparation of (±)-7,9-difluoro-5-(3-bromophenyl)-1,2-dihydro-2,2,4-trimethyl-5H-chromeno[3,4-f]quinoline (Compound 42, Structure 7 of Scheme II, where $R^8$=3-bromobenzene)

Compound 42 was prepared in a similar fashion as that described in Example 23 from Compound 11 (Structure 1 of Scheme II) and 1,3-dibromobenzene as a solid: $^1$H NMR (600 MHz, DMF-d$_6$) 7.88 (d, J=8.7, 1H), 7.67 (d, J=8.4, 1H), 7.61 (s, 1H), 7.59 (dq, J=10.2, 2.1, 1H), 7.50 (t, J=7.8, 1H), 7.46 (d, J=7.8, 1H), 7.30 (s, 1H), 7.13 (m, 1H), 7.11 (d, J=8.7, 1H), 6.77 (s, 1H), 5.72 (s, 1H), 2.22 (s, 3H), 1.47 (s, 3H), 1.44 (s, 3H).

EXAMPLE 32

Preparation of (±)-7,9-difluoro-5-(4-chlorophenyl)-1,2-dihydro-2,2,4-trimethyl-5H-chromeno[3,4-f]quinoline (Compound 43, Structure 7 of Scheme II, where $R^8$=4-chlorobenzene)

Compound 43 was prepared in a similar fashion as that described in Example 23 from Compound 11 (Structure 1 of Scheme II) and 4-bromochlorobenzene as a solid: $^1$H NMR (500 MHz, CDCl$_3$) 7.38 (d, J=8.4, 1H), 7.17 (M, 4H), 6.99 (dq, J=9.6, 2, 1H), 6.92 (s, 1H), 6.69 (d, J=8.6, 1H), 6.56 (m, 1H), 5.48 (s, 1H), 4.45 (s, 1H), 1.97 (s, 3H), 1.30 (s, 3H), 1.25 (s, 3H).

EXAMPLE 33

Preparation of (±)-7,9-difluoro-1,2-dihydro-2,2,4,5-tetramethyl-5H-chromeno[3,4-f]quinoline (Compound 44, Structure 7 of Scheme II, where $R^8$=methyl)

Compound 44 was prepared in a similar fashion as that described in Example 23 from Compound 11 (Structure 1 of Scheme II) and methyllithium as a solid: $^1$H NMR (500 MHz, DMF-d$_7$) 7.54 (d, J=8.8, 1H), 7.41 (dq, J=10, 2, 1H), 7.02 (m, 1H), 6.74 (d, J=8.8, 1H), 6.36 (s, 1H), 6.16 (q, J=6.4, 1H), 5.50 (m, 1H), 2.23 (s, 3H), 1.32 (d, J=6.6, 3H), 1.21 (s, 3H), 1.16 (s, 3H).

EXAMPLE 34

Preparation of (±)-7,9-difluoro-5-(2-oxo-2-phenylethyl)-1,2-dihydro-2,2,4-trimethyl-5H-chromeno[3,4-f]quinoline (Compound 45, Structure 7 of Scheme II, where $R^8$=2-oxo-2-phenylethyl)

To a stirred solution of 0.31 mmol of compound 32 (Structure 6 of Scheme II) in 10 mL of dichloromethane and 0.3 mL of 1-phenyl-1-trimethylsilyloxyethene at −78° C. under a nitrogen atmosphere was added 0.22 mL of boron trifluoride diethyl etherate. After stirring for 30 minutes a saturated aqueous solution of sodium hydrogencarbonate was added and the resulting mixture was extracted three times with dichloromethane. The organic extracts were combined, dried (Na$_2$SO$_4$) and concentrated. Purification using column chromatography on silica gel (toluene) and then HPLC (LUNA C18(2), CH$_3$CN/water, gradient 95/5 to 100/0) yielded 50 mg of compound 45 as a solid: $^1$H NMR (500 MHz, DMF-d$_7$) 7.91 (dd, J=8.8, 1.2, 2H), 7.64 (d, J=8.6, 1H), 7.64 (tt, J=7.4, 1H), 7.50 (d, J=8.4, 1H), 7.49 (m, 2H), 6.95 (m, 1H), 6.80 (dd, 1H), 6.82 (d, J=8.4, 1H), 6.46 (d, J=2, 1H), 5.55 (t, J=1.8, 1H), 3.92 (dd, J=17.4, 10, 1H), 3.02, (dd, J=17.4, 2.4, 1H), 2.31, (s, 3H), 1.27 (s, 3H), 1.17 (s, 3H).

EXAMPLE 35

Preparation of (±)-7,9-difluoro-5-ethyl-1,2-dihydro-2,2,4-trimethyl-5H-chromeno[3,4-f]quinoline (Compound 46, Structure 7 of Scheme II, where R$^8$=ethyl)

Hydrogenation at atmospheric pressure of compound 47 in ethyl acetate using PtO$_2$ as catalyst and purification using HPLC (LUNA C18(2), CH$_3$CN/water) yielded compound 46 as a solid: $^1$H NMR (500 MHz, DMF-d$_7$) 7.57 (d, J=8.4, 1H), 7.43 (dq, J=10.2, 1.8, 1H), 7.05 (m, 1H), 6.77 (d, J=8.6, 1H), 6.39 (d, J=1.6, 1H), 5.87 (dd, J=10.2, 3.6, 1H), 5.54 (t, J=1.8, 1H), 2.25 (d, J=1.4, 3H), 1.74 (m, 1H), 1.52 (m, 1H), 1.27 (s, 3H), 1.18 (s, 3H), 1.00 (t, J=7.4, 3H).

EXAMPLE 36

Preparation of (±)-7,9-difluoro-5-ethenyl-1,2-dihydro-2,2,4-trimethyl-5H-chromeno[3,4-f]quinoline (Compound 47, Structure 7 of Scheme II, where R$^8$=vinyl)

Compound 47 was prepared in a similar fashion as that described in Example 34 from Compound 32 (Structure 6 of Scheme II) and tributyl(ethenyl)tin as a solid: $^1$H NMR (600 MHz, DMF-d$_7$) 7.78 (d, J=8.7, 1H), 7.59 (dt, J=10.2, 1H), 7.21 (m, 1H), 7.11 (d, J=8.4, 1H), 6.67 (m, 1H), 6.61 (s, 1H), 6.23 (m, 1H), 5.72 (s, 1H), 5.45 (dt, J=10.8, 1H), 5.15 (dt, J=17.7, 1H), 2.41 (s, 3H), 1.43 (s, 6H).

EXAMPLE 37

Preparation of (±)-7,9-difluoro-5-(2-oxo-3-butenyl)-1,2-dihydro-2,2,4-trimethyl-5H-chromeno[3,4-f] quinoline (Compound 48, Structure 7 of Scheme II, where R$^8$=2-oxo-3-butenyl)

Compound 48 was prepared in a similar fashion as that described in Example 34 from Compound 32 (Structure 6 of Scheme II) and 2-trimethylsilyloxy-1,3-butadiene as a solid. $^1$H NMR (600 MHz, DMF-d$_7$) 7.61 (d, J=8.7, 1H), 7.47 (dt, J=10.5, 2.4, 1H), 7.02 (m, 1H), 6.80 (d, J=8.7, 1H), 6.64 (dd, J=10.5, 2.7, 1H), 6.45 (s, 1H), 6.40 (dd, J=17.7, 11.1, 1H), 6.16 (d, J=18, 1H), 5.91 (d, J=11.4, 1H), 5.55 (s, 1H), 3.48 (dd, 1H), 2.62 (dd, J=17.1, 2.7, 1H), 2.29 (s, 3H), 1.26 (s, 3H), 1.18 (s, 3H).

EXAMPLE 38

Preparation of Methyl (±)-7,9-difluoro-1,2-dihydro-α,α,2,2,4-pentamethyl-5H-chromeno[3,4-f] quinoline-5-ethanoate (Compound 49, Structure 7 of Scheme II, where R$^8$=1-methoxycarbonyl-1-methylethyl)

Compound 49 was prepared in a similar fashion as that described in Example 34 from Compound 32 (Structure 6 of Scheme II) and 1-methoxy-2-methyl-1-trimethylsilyloxypropene as a solid: $^1$H NMR (600 MHz, DMF-d$_7$) 7.86 (d, J=8.7, 1H), 7.64 (dt, J=5.3, 1.8, 1H), 7.21 (m, 1H), 7.04 (d, J=8.4, 1H), 6.80 (s, 1H), 6.48 (s, 1H), 5.73 (s, 1H), 3.81 (s, 3H), 2.49 (s, 3H), 1.57 (s, 3H), 1.31 (s, 3H), 1.28 (s, 3H), 1.10 (s, 3H).

EXAMPLE 39

Preparation of (±)-7,9-difluoro-5-ethynyl-1,2-dihydro-2,2,4-trimethyl-5H-chromeno[3,4-f]quinoline (Compound 50, Structure 7 of Scheme II, where R$^8$=acetylene)

Compound 50 was prepared in a similar fashion as that described in Example 34 from Compound 32 (Structure 6 of Scheme II) and ethynyltributyltin as a solid: $^1$H NMR (400 MHz, DMF-d$_7$) 7.77 (d, J=8.6, 1H), 7.66 (dt, J=10, 1.6, 1H), 7.29 (m, 1H), 7.00 (d, J=8.4, 1H), 6.86 (d, J=2.2, 1H), 6.70 (s, 1H), 5.74 (s, 1H), 3.81 (dd, J=2.4, 0.8, 1H), 2.59 (s, 3H), 1.49 (s, 3H), 1.37 (s, 3H).

EXAMPLE 40

Preparation of (±)-7,9-difluoro-5-cyano-1,2-dihydro-2,2,4-trimethyl-5H-chromeno[3,4-f]quinoline (Compound 51, Structure 7 of Scheme II, where R$^8$=cyano)

Compound 51 was prepared in a similar fashion as that described in Example 34 from Compound 32 (Structure 6 of Scheme II) and trimethylsilyl cyanide as a solid: $^1$H NMR (400 MHz, DMF-d$_7$) 7.56 (d, J=8.8, 1H), 7.46 (dq, J=10, 1.8, 1H), 7.1 (m, 1H), 7.04 (s, 1H), 6.79 (d, J=8.8, 1H), 6.64 (s, 1H), 5.50 (q, 1H), 2.26 (s, 3H), 1.20 (s, 3H), 1.06 (s, 3H).

EXAMPLE 41

Preparation of (±)-7,9-difluoro-5-butyl-1,2-dihydro-2,2,4-trimethyl-5H-chromeno[3,4-f]quinoline (Compound 52, Structure 7 of Scheme II, where R$^8$=butyl)

Compound 52 was prepared in a similar fashion as that described in Example 23 from Compound 11 (Structure 1 of Scheme II) and n-butyllithium as a solid: $^1$H NMR (600 MHz, DMF-d$_7$) 7.60 (d, J=7.1, 1H), 7.46 (d, J=7.1, 1H), 7.08 (m, 1H), 6.80 (d, J=5.7, 1H), 6.42 (s, 1H), 5.98 (d, J=7.1, 1H), 5.57 (s, 1H), 2.28 (s, 3H), 1.78 (m, 1H), 1.48 (m, 3H), 1.3 (m, 2H), 1.3 (s, 3H), 1.20 (s, 3H), 0.86 (t, J=4.2, 3H).

EXAMPLE 42

Preparation of (±)-7,9-difluoro-5-(2-thienyl)-1,2-dihydro-2,2,4-trimethyl-5H-chromeno[3,4-f]quinoline (Compound 53, Structure 7 of Scheme II, where R$^8$=2-thiophene)

Compound 53 was prepared in a similar fashion as that described in Example 34 from Compound 32 (Structure 6 of Scheme II) and 2-(tributylstannyl)thiophene as a solid: $^1$H NMR (600 MHz, DMF-d$_7$) 7.80 (d, J=8.7, 1H), 7.53 (dd, J=5.4, 1.2, 1H), 7.43 (d, J=10.2, 1H), 7.26 (s, 1H), 6.96 (m, 1H), 6.93 (m, 1H), 6.91 (d, J=8.7, 1H), 6.78 (d, J=3.6, 1H), 6.52 (s, 1H), 5.57 (s, 1H), 2.14 (s, 3H), 1.27 (s, 6H).

EXAMPLE 43

Preparation of (±)-7,9-difluoro-5-(2-furyl)-1,2-dihydro-2,2,4-trimethyl-5H-chromeno[3,4-f]quinoline (Compound 54, Structure 7 of Scheme II, where $R^8$=2-furyl)

Compound 54 was prepared in a similar fashion as that described in Example 23 from Compound 32 (Structure 6 of Scheme II) and 2-(tributylstannyl)furan as a solid: $^1$H NMR (600 MHz, DMF-$d_7$) 7.69 (s, 1H), 7.65 (d, J=8.7, 1H), 7.44 (dt, J=11.4, 1H), 6.99 (s, 1H), 6.94 (m, 1H), 6.88 (d, 8.4, 1H), 6.48 (s, 1H), 6.30 (q, J=1.5, 1H), 5.92 (d, J=3.3, 1H), 5.49 (s, 1H), 2.10 (s, 3H), 1.26 (s, 3H), 1.21 (s, 3H).

EXAMPLE 44

Preparation of (±)-7,9-difluoro-5-allyl-1,2-dihydro-2,2,4-trimethyl-5H-chromeno[3,4-f]quinoline (Compound 55, Structure 7 of Scheme II, where $R^8$=allyl)

Compound 55 was prepared in a similar fashion as that described in Example 34 from Compound 32 (Structure 6 of Scheme II) and allyltrimethylsilane as a solid: $^1$H NMR (400 MHz, DMF-$d_7$) 7.78 (d, J=8.6, 1H), 7.64, (dq, J=10.2, 1.8, 1H), 7.24 (m, 1H), 6.97 (d, J=8.6, 1H), 6.61 (d, J=1.6, 1H), 6.24 (dd, J=10, 4, 1H), 6.09 (m, 1H), 6.73 (t, J=1.6, 1H), 5.27 (m, 1H), 5.23 (m, 1H), 2.71 (m, 1H), 2.48 (m, 1H), 2.44 (s, 3H), 1.46 (s, 3H), 1.38 (s, 3H).

EXAMPLE 45

Preparation of (±)-7,9-difluoro-5-[3-(trifluoromethyl)phenyl]-1,2-dihydro-2,2,4-trimethyl-5H-chromeno[3,4-f]quinoline (Compound 56, Structure 7 of Scheme II, where $R^8$=3-trifluoromethylphenyl)

Compound 56 was prepared in a similar fashion as that described in Example 23 from Compound 11 (Structure 1 of Scheme II) and 3-bromobenzotrifluoride as a solid: $^1$H NMR (400 MHz, DMF-$d_7$) 7.87 (d, J=8.6, 1H), 7.84 (m, 1H), 7.78 (t, J=7.6, 2H), 7.72 (m, 1H), 7.57 (dq, J=10, 1.8, 1H), 7.38 (s, 1H), 7.12 (m, 1H), 7.11 (d, J=8.6, 1H), 6.78 (d, J=2, 1H), 6.71 (t, J=1.6, 1H), 2.21 (d, J=1.4, 3H), 1.45 (s, 3H), 1.44 (s, 3H).

EXAMPLE 46

Preparation of Ethyl (±)-7,9-difluoro-1,2-dihydro-α-methylene-2,2,4-trimethyl-5H-chromeno[3,4-f] quinoline-5-propanoate (Compound 57, Structure 7 of Scheme II, where $R^8$=2-ethoxycarbonyl-2-propenyl)

Compound 57 was prepared in a similar fashion as that described in Example 34 from Compound 32 (Structure 6 of Scheme II) and ethyl 2-(trimethylsilylmethyl)acrylate as a solid: $^1$H NMR (600 MHz, DMF-$d_7$) 7.52 (d, J=8.7, 1H), 7.38 (dq, J=10.2, 1.8, 1H), 6.94 (m, 1H), 6.69 (d, J=8.4, 1H), 6.35 (d, J=1.5, 1H), 6.17 (dd, J=10.5, 4.2, 1H), 6.12 (d, J=1.2, 1H), 5.45 (s, 1H), 5.40 (s, 1H), 4.12 (m, 2H), 2.57 (dd, J=15, 10.5, 1H), 2.44 (dd, J=15, 3.9, 1H), 2.23 (s, 3H), 1.21 (s, 3H), 1.18, (t, J=7.2, 3H), 1.06 (s, 3H).

EXAMPLE 47

Preparation of (±)-7,9-difluoro-1,2-dihydro-β-methylene-2,2,4-trimethyl-5H-chromeno[3,4-f]quinoline-5-propanol (Compound 58, Structure 7 of Scheme II, where $R^8$=2-hydroxymethyl-2-propenyl)

To a solution of 64 mg of compound 59 (Structure 7 of Scheme II, where $R^8$=2-acetyloxymethyl-2-propenyl) in 2 mL of methanol, 0.5 mL of THF and 0.5 mL of aqueous 20% KOH stirred at room temperature for 3 hours 2 M hydrochloric acid was added to adjust the pH to 7. A saturated solution of sodium hydrogencarbonate was added and the resulting mixture was extracted with ethyl acetate. The organic extract was dried ($Na_2SO_4$) and concentrated to yield 60 mg of compound 58 as a solid: $^1$H NMR (400 MHz, DMF-$d_7$) 7.46 (dd, J=8.6, 1.8, 1H), 7.32 (dq, J=10, 1.8, 1H), 6.90 (m, 1H), 6.65 (dd, J=8.4, 1.8, 1H), 6.11 (d, J=10.6, 1H), 5.40 (s, 1H), 4.98 (s, 1H), 4.66 (s, 1H), 4.20 (d, J=14.2, 1H), 3.90 (d, J=14.2, 1H), 2.36 (dd, J=15.6, 10.8, 1H), 2.17 (s, 3.5H), 2.13 (s, 0.5H), 1.14 (s, 3H), 1.05 (s, 3H).

EXAMPLE 48

Preparation of (±)-7,9-difluoro-1,2-dihydro-β-methylene-2,2,4-trimethyl-5H-chromeno[3,4-f]quinoline-5-propanol acetate (Compound 59, Structure 7 of Scheme II, where $R^8$=2-acetyloxymethyl-2-propenyl)

Compound 59 was prepared by a similar procedure as described in Example 34 from Compound 32 (Structure 6 of Scheme II) and ethyl 2-[(trimethylsilyl)methyl]-2-propen-1-yl acetate as a solid: $^1$H NMR (600 MHz, DMF-$d_7$) 7.63 (d, J=8.7, 1H), 7.49 (d, J=9.9, 1H), 7.07 (m, 1H), 6.82 (d, J=8.7, 1H), 6.45 (s, 1H), 6.26 (dd, J=10.8, 2.7, 1H), 5.58 (s, 1H), 5.23 (s, 1H), 5.05 (s, 1H), 4.71 (d, J=13.5, 1H), 4.60 (d, J=13.5, 1H), 2.63 (dd, J=16.2, 11.1, 1H), 2.35 (s, 1H), 2.32 (s, 3H), 2.08 (s, 3H), 1.29 (s, 3H), 1.22 (s, 3H).

EXAMPLE 49

Preparation of (±)-7,9-difluoro-5-(1-methylethenyl)-1,2-dihydro-2,2,4-trimethyl-5H-chromeno[3,4-f] quinoline (Compound 60, Structure 7 of Scheme II, where $R^8$=1-methylvinyl)

Compound 60 was prepared in a similar fashion as that described in Example 34 from Compound 32 (Structure 6 of Scheme II) and (propen-2-yl)tributyltin as a solid: $^1$H NMR (600 MHz, DMF-$d_7$) 7.76 (d, J=8.3, 1H), 7.57 (dq, J=10.2, 1.8, 1H), 7.21 (m, 1H), 7.02 (d, J=8.7, 1H), 6.58 (s, 1H), 6.44 (s, 1H), 5.60 (m, 1H), 5.23 (s, 1H), 4.63 (s, 1H), 2.37 (s, 3H), 2.31 (s, 3H), 1.45 (s, 3H), 1.40 (s, 3H).

EXAMPLE 50

Preparation of (±)-7,9-difluoro-5-(N-methyl-2-pyrrolyl)-1,2-dihydro-2,2,4-trimethyl-5H-chromeno[3,4-f]quinoline (Compound 61, Structure 7 of Scheme II, where $R^8$=N-methyl-2-pyrrolyl)

Compound 61 was prepared in a similar fashion as that described in Example 34 from Compound 32 (Structure 6 of Scheme II) and N-methyl-2-(tributylstannyl)pyrrole as a solid: $^1$H NMR (400 MHz, DMF-$d_7$) 7.65 (dd, J=8.6, 2, 1H), 7.43 (m, 1H), 7.05 (s, 1H), 6.92 (m, 1H), 6.89 (m, 1H), 6.81

(m, 1H), 6.43 (s, 1H), 5.74 (m, 1H), 5.48 (m, 1H), 5.42 (m, 1H), 3.95 (m, 3H), 1.98 (d, J=2, 3H), 1.29 (d, J=2.2, 3H), 1.21 (d, 3H).

EXAMPLE 51

Preparation of (±)-7,9-difluoro-5-phenylethynyl-1,2-dihydro-2,2,4-trimethyl-5H-chromeno[3,4-f]quinoline (Compound 62, Structure 7 of Scheme II, where $R^8$=phenylacetylene)

Compound 62 was prepared in a similar fashion as that described in Example 34 from Compound 32 (Structure 6 of Scheme II) and (phenylethynyl)tributyltin as a solid: $^1$H NMR (400 MHz, DMF-$d_7$) 7.64 (dd, J=8.6, 1H), 7.52 (m, 1H), 7.37 (m, 3H), 7.28 (m, 2H), 7.14 (m, 1H), 6.92 (d, J=3, 1H), 6.86 (m, 1H), 6.76 (s, 1H), 5.60 (s, 1H), 2.49 (d, J=1.8, 3H), 1.35 (d, J=2, 3H), 1.22 (d, J=2.2, 3H).

EXAMPLE 52

Preparation of (±)-7,9-difluoro-5-(benzo[b]thien-2-yl)-1,2-dihydro-2,2,4-trimethyl-5H-chromeno[3,4-f]quinoline (Compound 63, Structure 7 of Scheme II, where $R^8$=2-benzo[b]thiophene)

Compound 63 was prepared in a similar fashion as that described in Example 34 from Compound 32 (Structure 6 of Scheme II) and 2-(tributylstannyl)benzo[b]thiophene as a solid: $^1$H NMR (600 MHz, DMF-$d_7$) 8.11 (m, 1H), 7.94 (m, 1H), 7.89 (d, J=8.7, 1H), 7.61 (dq, J=9.9, 1H), 7.51 (m, 3H), 7.20 (s, 1H), 7.12 (m, 1H), 7.12 (d, J=8.4, 1H), 6.75 (d, J=1.5, 1H), 5.72 (s, 1H), 2.36 (d, J=1.2, 3H), 1.48 (s, 3H), 1.45 (s, 3H).

EXAMPLE 53

Preparation of (−)-7,9-difluoro-5-(benzo[b]thien-2-yl)-1,2-dihydro-2,2,4-trimethyl-5H-chromeno[3,4-f]quinoline and (+)-7,9-difluoro-5-(benzo[b]thien-2-yl)-1,2-dihydro-2,2,4-trimethyl-5H-chromeno[3,4-f]quinoline (Compound 64 and 65, Structure 7 of Scheme II, where $R^8$=2-benzo[b]thiophene)

Compounds 64 and 65 were prepared by chiral HPLC separation of Compound 63 (Structure 7 of Scheme II, where $R^8$=2-benzothiophene) as pure enantiomers. Retention times: (R,R) Whelk-O2 10/100; 0.46 cm×25 cm, flow 1 ml/min, heptanes/iso-propanol 98/2; Rt=14 min and 18 min. Compound 64 is the (−)-isomer; and compound 65 is the (+)-isomer.

EXAMPLE 54

Preparation of (±)-7,9-difluoro-5-(5-methyl-2-furyl)-1,2-dihydro-2,2,4-trimethyl-5H-chromeno[3,4-f]quinoline (Compound 66, Structure 7 of Scheme II, where $R^8$=5-methyl-2-furyl)

Compound 66 was prepared in a similar fashion as that described in Example 34 from Compound 32 (Structure 6 of Scheme II) and 5-methyl-2-(tributylstannyl)furan as a solid: $^1$H NMR (400 MHz, DMF-$d_7$) 7.82 (m, 1H), 7.62 (m, 1H), 7.12 (m, 2H), 7.05 (m, 1H), 6.65 (s, 1H), 6.07 (s, 1H), 5.92 (m, 1H), 5.67 (s, 1H), 2.41 (dd, J=8.4, 3H), 2.22 (d, J=8, 3H), 1.44 (m, 3H), 1.39 (m, 3H).

EXAMPLE 55

Preparation of (±)-7,9-difluoro-5-(2-benzo[b]furyl)-1,2-dihydro-2,2,4-trimethyl-5H-chromeno[3,4-f]quinoline (Compound 67, Structure 7 of Scheme II, where $R^8$=2-benzo[b]furyl)

Compound 67 was prepared in a similar fashion as that described in Example 34 from Compound 32 (Structure 6 of Scheme II) and 2-(tributylstannyl)benzo[b]furan as a solid: $^1$H NMR (400 MHz, CDCl$_3$) 7.49 (d, J=8.6, 1H), 7.40 (d, J=8.6, 1H), 7.36 (d, J=8.4, 1H), 7.26 (m, 1H), 7.14 (m, 1H), 7.08 (m, 2H), 6.71 (d, J=8.4, 1H), 6.58 (m, 1H), 6.23 (s, 1H), 5.48 (d, J=1.4, 1H), 4.05 (s, 1H), 2.04 (s, 3H), 1.30 (s, 3H), 1.25 (s, 3H).

EXAMPLE 56

Preparation of (±)-7,9-difluoro-5-[4-(dimethylamino)phenyl]-1,2-dihydro-2,2,4-trimethyl-5H-chromeno[3,4-f]quinoline (Compound 68, Structure 7 of Scheme II, where $R^8$=4-dimethylaminophenyl)

Compound 68 was prepared in a similar fashion as that described in Example 34 from Compound 32 (Structure 6 of Scheme II) and (3-[dimethylamino]phenyl)tributyltin as a solid: $^1$H NMR (400 MHz, DMSO-$d_6$) 7.54 (d, J=8.8, 1H), 7.32 (dq, J=10.2, 1H), 6.92 (m, 2H), 6.88 (m, 1H), 6.85 (s, 1H), 6.74 (d, J=8.6, 1H), 6.54 (m, 2H), 6.43 (d, J=1.8, 1H), 5.38 (s, 1H), 2.82 (s, 6H), 1.90 (s, 3H), 1.20 (s, 3H), 1.16 (s, 3H).

EXAMPLE 57

Preparation of (±)-7,9-difluoro-5-(5-methyl-2-thienyl)-1,2-dihydro-2,2,4-trimethyl-5H-chromeno[3,4-f]quinoline (Compound 69, Structure 7 of Scheme II, where $R^8$=5-methyl-2-thiophene)

Compound 69 was prepared in a similar fashion as that described in Example 34 from Compound 32 (Structure 6 of Scheme II) and 5-methyl-2-(tributylstannyl)thiophene as a solid: $^1$H NMR (400 MHz, DMSO-$d_6$) 7.55 (d, J=8.6, 1H), 7.36 (dq, J=10.2, 1.8, 1H), 7.05 (s, 1H), 6.96 (m, 1H), 6.75 (d, J=3.4, 1H), 6.52 (dd, J=3.8, 1.2, 1H), 6.48 (d, J=2, 1H), 6.40 (d, J=3.4, 1H), 5.41 (s, 1H), 2.11 (s, 3H), 2.01 (s, 3H), 1.18 (s, 3H), 1.17 (s, 3H).

EXAMPLE 58

Preparation of (±)-7,9-difluoro-5-(5-methoxy-2-furyl)-1,2-dihydro-2,2,4-trimethyl-5H-chromeno[3,4-f]quinoline (Compound 70, Structure 7 of Scheme II, where $R^8$=5-methoxy-2-furyl)

Compound 70 was prepared in a similar fashion as that described in Example 34 from Compound 32 (Structure 6 of Scheme II) and 5-methoxy-2-(tributylstannyl)furan as a solid: $^1$H NMR (600 MHz, CDCl$_3$) 7.35 (d, J=8.7, 1H), 7.06 (dt, J=9.6, 1H), 6.80 (s, 1H), 6.65 (d, J=8.4, 1H), 6.62 (m, 1H), 5.69 (d, J=3.3, 1H), 5.47 (s, 1H), 4.88 (d, J=3.3, 1H), 3.98 (s, 1H), 3.79 (s, 3H), 2.05 (d, J=0.9, 3H), 1.29 (s, 3H), 1.22 (s, 3H).

EXAMPLE 59

Preparation of (±)-7,9-difluoro-5-(2-propynyl)-1,2-dihydro-2,2,4-trimethyl-5H-chromeno[3,4-f]quinoline (Compound 71, Structure 7 of Scheme II, where $R^8$=2-propynyl)

Compound 71 was prepared in a similar fashion as that described in Example 34 from Compound 32 (Structure 6 of Scheme II) and 2-propynyltributyltin as a solid: $^1$H NMR (400 MHz, DMF-$d_7$) 7.57 (d, J=8.8, 1H), 7.43 (dq, J=10.4, 1.8, 1H), 7.05 (m, 1H), 6.77 (d, J=8.6, 1H), 6.44 (s, 1H), 6.19 (q, J=4.6, 1H), 5.51 (t, J=1.8, 1H), 2.84 (t, J=2.8, 1H), 2.64 (m, 1H), 2.48 (dq, J=17.6, 2.8, 1H), 2.27 (s, 3H), 1.25 (s, 3H), 1.16 (s, 3H).

EXAMPLE 60

Preparation of (−)-7,9-difluoro-5-(2-propynyl)-1,2-dihydro-2,2,4-trimethyl-5H-chromeno[3,4-f]quinoline and (+)-7,9-difluoro-5-(2-propynyl)-1,2-dihydro-2,2,4-trimethyl-5H-chromeno[3,4-f]quinoline (Compounds 72 and 73, Structure 7 of Scheme II, where $R^8$=2-propynyl)

Compounds 72 and 73 were prepared by chiral HPLC separation of Compound 71 (Structure 7 of Scheme II, where $R^8$=2-propynyl) as pure enantiomers. Retention times: OJ column 2.0 cm×50 cm, flow 10 ml/min, heptanes/ethanol 90/10; Rt=40 min and 45 min. Compound 72 is the (−)-isomer; and Compound 73 is the (+)-isomer.

EXAMPLE 61

Preparation of (±)-7,9-difluoro-5-(1-propynyl)-1,2-dihydro-2,2,4-trimethyl-5H-chromeno[3,4-f]quinoline (Compound 74, Structure 7 of Scheme II, where $R^8$=1-propynyl)

Compound 74 was prepared in a similar fashion as that described in Example 34 from Compound 32 (Structure 6 of Scheme II) and (1-propynyl)tributyltin as a solid: $^1$H NMR (400 MHz, DMSO-$d_6$) 7.46 (d, J=8.6, 1H), 7.42 (dq, J=10, 1.8, 1H), 7.08 (m, 1H), 6.67 (d, J=8.6, 1H), 6.54 (q, J=2.2, 1H), 6.48 (d, J=2, 1H), 5.46 (t, J=1.6, 1H), 2.29 (s, 3H), 1.69 (d, J=2, 3H), 1.25 (s, 3H), 1.11 (s, 3H).

EXAMPLE 62

Preparation of (−)-7,9-difluoro-5-(1-propynyl)-1,2-dihydro-2,2,4-trimethyl-5H-chromeno[3,4-f]quinoline and (+)-7,9-difluoro-5-(1-propynyl)-1,2-dihydro-2,2,4-trimethyl-5H-chromeno[3,4-f]quinoline (Compounds 75 and 76, Structure 7 of Scheme II, where $R^8$=1-propynyl)

Compounds 75 and 76 were prepared by chiral HPLC separation of Compound 74 (Structure 7 of Scheme II, where $R^8$=1-propynyl) as pure enantiomers. Retention times: OJ column 2.0 cm×50 cm, flow 10 ml/min, heptanes/ethanol 90/10; Rt=37 min and 47 min. Compound 75 is the (−)-isomer; and Compound 76 is the (+)-isomer.

EXAMPLE 63

Preparation of (±)-7,9-difluoro-5-(4,5-dimethyl-2-furyl)-1,2-dihydro-2,2,4-trimethyl-5H-chromeno[3,4-f]quinoline (Compound 77, Structure 7 of Scheme II, where $R^8$=4,5-dimethyl-2-furyl)

Compound 77 was prepared in a similar fashion as that described in Example 34 from Compound 32 (Structure 6 of Scheme II) and 2,3-dimethyl-5-(tributylstannyl)furan as a solid: $^1$H NMR (400 MHz, DMSO-$d_6$) 7.54 (d, J=8.6, 1H), 7.39 (dq, J=10, 1.8, 1H), 6.97 (m, 1H), 6.80 (s, 1H), 6.74 (d, J=8.4, 1H), 6.46 (d, J=1.8, 1H), 5.55 (s, 1H), 5.40 (s, 1H), 2.12 (s, 3H), 1.92 (s, 3H), 1.69 (s, 3H), 1.21 (s, 3H), 1.13 (s, 3H).

EXAMPLE 64

Preparation of (±)-7,9-difluoro-5-(2-methyl-1-propenyl)-1,2-dihydro-2,2,4-trimethyl-5H-chromeno[3,4-f]quinoline (Compound 78, Structure 7 of Scheme II, where $R^8$=2-methyl-1-propenyl)

Compound 78 was prepared in a similar fashion as that described in Example 34 from Compound 32 (Structure 6 of Scheme II) and 2-methylpropenylmagnesium bromide as a solid: $^1$H NMR (400 MHz, DMSO-$d_6$) 7.47 (d, J=8.6, 1H), 7.36 (m, 1H), 6.98 (m, 1H), 6.66 (d, J=8.4, 1H), 6.41 (d, J=1.8, 1H), 6.38 (d, J=7.4, 1H), 5.42 (s, 1H), 5.17 (d, J=7.6, 1H), 2.11 (s, 3H), 1.88 (s, 3H), 1.62 (s, 3H), 1.21 (s, 3H), 1.14 (s, 3H).

EXAMPLE 65

Preparation of (±)-7,9-difluoro-5-(3,4-dimethyl-2-thiennyl)-1,2-dihydro-2,2,4-trimethyl-5H-chromeno[3,4-f]quinoline (Compound 79, Structure 7 of Scheme II, where $R^8$=3,4-dimethyl-2-thiophene)

Compound 79 was prepared in a similar fashion as that described in Example 34 from Compound 32 (Structure 6 of Scheme II) and 3,4-dimethyl-2-(tributylstannyl)thiophene as a solid: $^1$H NMR (600 MHz, DMSO-$d_6$) 7.55 (d, J=9, 1H), 7.38 (m, 1H), 7.12 (s, 1H), 6.91 (m, 1H), 6.87 (s, 1H), 6.76 (d, J=8.4, 1H), 6.46 (d, J=1.8, 1H), 5.38 (s, 1H), 2.27 (s, 3H), 2.05 (s, 3H), 1.93 (s, 3H), 1.18 (s, 3H), 1.16 (s, 3H).

EXAMPLE 66

Preparation of (±)-7,9-difluoro-5-(3-(3-bromophenyl)phenyl)-1,2-dihydro-2,2,4-trimethyl-5H-chromeno[3,4-f]quinoline (Compound 80, Structure 7 of Scheme II, where $R^8$=3-(3-bromophenyl)phenyl)

Compound 80 was isolated as aminor product of the reaction described in example 31 as a solid: $^1$H NMR (600 MHz, DMSO-$d_6$) 7.65 (t, J=2.1, 1H), 7.58 (d, J=8.7, 1H), 7.55 (m, 1H), 7.49 (m, 1H), 7.41 (t, J=8.4, 1H), 7.35 (m, 2H), 7.09 (d, J=7.8, 1H), 7.08 (s, 1H), 6.93 (m, 1H), 6.79 (d, J=8.7, 1H), 6.53 (d, J=2.1, 1H), 5.45 (s, 1H), 1.97 (s, 3H), 1.21 (s, 6H).

EXAMPLE 67

Preparation of 7,9-difluoro-5(Z)-(2-methylbenzylidene)-1,2-dihydro-2,2,4-trimethyl-5H-chromeno[3,4-f]quinoline (Compound 81, Structure 2 of Scheme I, where $R^9$=2-methylphenyl)

This compound was prepared in a similar fashion as that described in Example 1 from 2-methylbenzyl Grignard reagent and Compound 11 (Structure 1 of Scheme I) as a yellow solid: $^1$H-NMR (400 MHz, $CDCl_3$) 8.30 (d, J=8.0, 1H), 7.38 (d, J=8.4, 1H), 7.31–7.24 (m, 1H), 7.17–7.10 (m, 4H), 6.73–6.82 (m, 1H), 6.66 (d, J=8.4, 1H), 5.96 (s, 1H), 5.53 (s, 1H), 4.24 (s, 1H), 2.28 (s, 3H), 2.14 (s, 3H), and 1.25 (bs, 6H).

EXAMPLE 68

The PR modulating activities and binding affinities of selected steroid receptor modulator compounds of the present invention were evaluated utilizing the cotransfection assay, and the standard receptor competitive binding assays, according to the following illustrative Examples. The receptor-selectivities of the selected analogues towards PR relative to other steroid hormone receptors were also assessed in the cotransfection assay under the same cell background. The potential tissue-selectivities of the selected analogues were examined by using the T47D alkaline phosphatase assay that was developed from human breast cancer cells with endogenous PRs.

Cotransfection Assay

The function and detailed preparation procedure of the cotransfection assays have been described previously (Pathirana, C. et al., Nonsteroidal Human Progesterone Receptor Modulators from the Marine Alga Cymopolia Barbata. *Mol. Pharm.* 1995, 47, 630–635). Briefly, the cotransfection assays were carried out in CV-1 cells (African green monkey kidney fibroblasts), which were transiently transfected, by the standard calcium phosphate coprecipitation procedure (Berger, T. S. et al., Interaction of Glucocorticoid Analogues with the Human Glucocorticoid Receptor. *J. Steroid Biochem. Mol. Bio.* 1992, 41, 733–738) with the Plasmid containing receptor, MTV-LUC reporter, pRS-β-Gal, and filler DNA (Rous sarcoma virus chloramphenicol acetyltransferase). The agonist activity was determined by examining the LUC expression (normalized response) and the efficacy readout was a relative value to the maximal LUC expression produced by a reference agonist as 100%, e.g., progesterone for hPR, dihydrotestosterone (DHT) for human androgen receptor (hAR), dexamethasone for hGR, aldosterone for human mineralocorticoid receptor (hMR) and estradiol for human estrogen receptor (hER). Antagonist efficacy was determined as a function (%) of maximal inhibition of a reference agonist at $EC_{50}$ concentration. All the cotransfection experiments were carried out in 96-well plates by automation (Beckman Biomomek automated workstation).

Receptor Binding Assays

The preparation of receptor binding assays for hPR-A was described in literature (Pathirana, C. et al., Nonsteroidal Human Progesterone Receptor Modulators from the Marie Alga Cymopolia Barbata. *Mol. Pharm.* 1995, 47, 630–635.)

T47D Alkaline Phosphatase Assay

The T47D alkaline phosphatase assays were performed as described previously (Lorenzo, D. D. et. Al., Progestin Regulation of Alkaline phosphatase in the Human Breast Cancer Cell Line T47D, *Cancer Res.* 1991, 51, 4470).

The agonist, antagonist and binding activity assay results of selected progesterone receptor modulator compounds of the present invention and the standard reference compounds on PR are shown in Table 1 below. Efficacy is reported as the percent maximal response observed for each compound relative to the reference agonist and antagonist compounds indicated above. Also reported in Table 1 for each compound is its antagonist potency or $IC_{50}$ (which is the concentration (nM), required to reduce the maximal response by 50%), and its agonist potency or $EC_{50}$ (nM), (which is the effective concentration that produced 50% of the maximum response). Table 1 also lists the PR modulating activity in T47D cells to assess the potential tissue-selectivity comparing to marketed steroidal progestins or antiprogestins. All of the reference steroids demonstrated full agonist or antagonist activties in both cell lines; however, the 7,9-difluoro compounds of the subject invention behaved as partial agonist/antagonist activities in human breast cancer cell line despite the full agonist or antagonist activities in the CV-1 cells.

TABLE 1

Agonist, antagonist and binding activity of progesterone receptor modulator compounds of present invention and the reference agonist compounds and reference antagonists compounds.

| Cmpd No. | hPR Agonist CV-1 Cells | | hPR Antagonist CV-1 Cells | | hPR Agonist T47D cells | | hPR Antagonists T47D Cells | | PR binding |
|---|---|---|---|---|---|---|---|---|---|
| | Eff. (%) | $EC_{50}$ (nM) | Eff. (%) | $IC_{50}$ (nM) | Eff. (%) | $EC_{50}$ (nM) | Eff. (%) | $IC_{50}$ (nM) | $K_i$ (nM) |
| Prog. | 100 | 0.5 | na | na | 100 | 2.3 | na | na | 3.5 |
| MPA | 88 | 0.4 | na | na | 114 | 0.7 | na | na | 1.4 |
| Norethindrone | 170 | 1.2 | na | na | 103 | 0.7 | na | na | 1.2 |
| Levonorgestrel | 216 | 0.1 | na | na | 96 | 0.5 | na | na | 0.4 |
| Drospirenone | 87 | 2.2 | na | na | 117 | 6.0 | na | na | 12 |
| 3-ketodesogestrel | 190 | 0.1 | na | na | 94 | 0.2 | na | na | 0.3 |
| RU486 | na | na | 94 | 0.6 | na | na | 94 | 3.7 | 1.1 |
| ZK299 | na | na | 99 | 1.6 | na | na | 86 | 2.8 | 18 |
| 10 | 153 | 4.9 | na | na | 54 | 30 | 49 | 97 | 6.8 |
| 14 | 103 | 7.4 | na | na | 58 | 49 | 44 | 116 | 6.0 |

TABLE 1-continued

Agonist, antagonist and binding activity of progesterone receptor modulator compounds of present invention and the reference agonist compounds and reference antagonists compounds.

| Cmpd No. | hPR Agonist CV-1 Cells | | hPR Antagonist CV-1 Cells | | hPR Agonist T47D cells | | hPR Antagonists T47D Cells | | PR binding |
|---|---|---|---|---|---|---|---|---|---|
| | Eff. (%) | $EC_{50}$ (nM) | Eff. (%) | $IC_{50}$ (nM) | Eff. (%) | $EC_{50}$ (nM) | Eff. (%) | $IC_{50}$ (nM) | $K_i$ (nM) |
| 15 | 191 | 3.8 | na | na | 56 | 19 | 52 | 711 | 9.7 |
| 17 | 169 | 2.9 | na | na | 62 | 12 | 42 | 389 | 9.5 |
| 18 | 142 | 1.3 | na | na | 57 | 17 | 58 | 55 | 3.9 |
| 19 | 212 | 1.4 | na | na | 65 | 8.7 | 35 | 360 | 8.5 |
| 20 | 147 | 2.8 | na | na | 63 | 6.6 | 59 | 170 | 2.9 |
| 24 | 52 | 9.4 | na | na | 72 | 79 | 26 | 830 | 58 |
| 26 | 159 | 0.6 | na | na | 63 | 7.5 | 46 | 610 | 9.0 |
| 29 | 191 | 2.3 | na | na | 62 | 8.7 | 40 | 170 | 7.0 |
| 30 | 186 | 5.3 | na | na | 66 | 33 | 44 | 840 | 4.5 |
| 31 | 171 | 2.7 | na | na | 66 | 14 | 39 | 610 | 7.9 |
| 32 | na | na | 76 | 75 | 36 | 315 | 35 | 250 | 37 |
| 33 | 85 | 3.5 | na | na | 62 | 35 | na | na | 2.7 |
| 34 | 114 | 1.2 | na | na | 60 | 34 | 47 | 565 | 2.5 |
| 37 | 89 | 1.24 | na | na | 50 | 130 | 56 | 150 | 2.2 |
| 38 | 110 | 1.2 | na | na | 54 | 6.2 | nt | nt | 2.0 |
| 39 | 26 | 28 | 62 | 24 | na | na | 29 | 4100 | nt |
| 41 | 146 | 1.87 | na | na | 54 | 42 | 50 | 135 | 2.8 |
| 45 | na | na | 79 | 42 | 77 | 195 | na | na | 18 |
| 63 | 154 | 2.3 | na | na | 61 | 20 | 49 | 490 | 6.5 |
| 74 | 89 | 0.7 | na | na | 58 | 4.6 | 40 | 53 | 3.5 | na = not active (i.e. efficacy of <20 and potency of >10,000)
nt = not tested

The receptor-selectivity profile of selected analogues was examined in the cotransfection assays with different steroid hormone receptors in comparison with the steroidal reference compounds and Table 2 lists the receptor-selectivity potency ratio of selected 7,9-difluoro analogues and PR modulating steroids. In general, the nonsteroidal analogues demonstrated more selectivity towards hPR than the steroids.

TABLE 2

Progesterone receptor-selectivity of selective PR modulator compounds of present invention and the reference steroidal progestins.

| Cmpd | hAR $EC_{50}$ or $IC_{50}$/ hPR $EC_{50}$ | hGR $EC_{50}$ or $IC_{50}$/ hPR $EC_{50}$ | hMR $EC_{50}$ or $IC_{50}$/ hPR $EC_{50}$ | hER $EC_{50}$ or $IC_{50}$/ hPR $EC_{50}$ |
|---|---|---|---|---|
| Prog | 23 | >1000 | 25 | >1000 |
| MPA | 41 | 67 | >1000 | >1000 |
| Norethindrone | 33 | 34 | >1000 | 9 |
| Levonorgestrel | >1000 | 142 | >1000 | >1000 |
| 3-ketodesogestrel | >1000 | 896 | >1000 | >1000 |
| 10 | 320 | 290 | >1000 | >1000 |
| 14 | 54 | 365 | >1000 | >1000 |
| 15 | 2 | 30 | >1000 | >1000 |
| 17 | 622 | 66 | >1000 | >1000 |
| 18 | 170 | 77 | >1000 | >1000 |
| 19 | >1000 | 432 | >1000 | >1000 |
| 20 | 8 | 27 | >1000 | >1000 |
| 26 | 742 | 342 | >1000 | >1000 |
| 29 | 6 | 83 | >1000 | >1000 |
| 30 | 377 | 19 | >1000 | >1000 |
| 31 | 517 | 59 | >1000 | >1000 |
| 33 | 37 | 10 | >1000 | >1000 |
| 34 | 8.5 | >1000 | >1000 | >1000 |
| 37 | 558 | 54 | >1000 | >1000 |
| 41 | 252 | 105 | 905 | >1000 |
| 63 | 136 | 8.8 | >1000 | 685 |
| 74 | 100 | >1000 | >1000 | >1000 |

EXAMPLE 69

The 7,9-difluoro substituents at the D-ring of formulae I and II of the present invention are generally superior to any other substituents in modulating PR activities, which is unexpected and surprising, in view of U.S. Pat. Nos. 5,693,646 and 5,696,127. The superiority of the 7,9-difluoro analogue compounds of the present invention was demonstrated utilizing the hPR cotransfection assay according to the following illustrative Examples. The $EC_{50}$ comparison between the new 7,9-difluoro compounds and analogues with substitution patterns different from 7,9-difluoro (disclosed in U.S. Pat. Nos. 5,693,646 and 5,696,127) are tabulated in Tables 3 and 4.

TABLE 3 hPR agonist potencies (EC$_{50}$ in nM) of selected 7,9-difluoro compounds of present invention (Formula I) and analogues with other D-ring substitution patterns in the cotransfection assay.

| X → | | 7,9-diF | H | 9-F | 9-OMe | 9-Cl | 9-Me | 8-F |
|---|---|---|---|---|---|---|---|---|
| R$^8$ | # | EC$_{50}$ | EC$_{50}$ | EC$_{50}$ | EC$_{50}$ | EC$_{50}$ | EC$_{50}$ | EC$_{50}$ |
| Ph | 33 | 3.5 | 203$^a$ | 7.4$^b$ | —$^c$ | 6.9$^b$ | — | — |
| 3-F-Ph | 40 | 6.66 | 9$^a$ | — | — | 3.7$^b$ | — | — |
| 3-Cl-Ph | 41 | 1.87 | 18$^b$ | 2.8$^b$ | — | 3.6$^b$ | 4.85 | — |
| 4-Cl-Ph | 43 | 5.1 | 15$^b$ | 8.1$^b$ | 3.1$^b$ | 9$^b$ | — | 10$^b$ |
| 3-Br-Ph | 42 | 3.65 | 8$^b$ | — | — | — | — | — |
| 4-Br-Ph | 36 | 4.96 | 14$^b$ | — | — | 5.2$^b$ | — | — |
| 3-Me-Ph | 34 | 1.2 | 145 | 5.0$^b$ | 11 | 7.1$^b$ | 44 | — |
| 3-CF$_3$-Ph | 56 | 1.6 | 13$^a$ | 10$^b$ | — | 7.4 | — | — |
| 4-Cl-3-Me-Ph | 37 | 1.24 | 14$^b$ | 2.7$^b$ | — | 9.4 | 7.45 | — |
| Benzodioxol-5-yl | 35 | 3.85 | 48 | — | — | — | — | — |
| Me | 44 | 1.4 | 2067 | 13 | — | 3 | — | — |
| Et | 46 | 6.93 | — | 9 | — | — | — | — |
| Allyl | 55 | 3.6 | 839 | 7.5 | — | — | — | — |
| Bu | 52 | 15 | 16$^a$ | 16$^a$ | 9 | 7 | 16 | 5285 |

$^a$EC$_{50}$ data from U.S. Pat. Nos. 5693646/5693647/5696127;
$^b$EC$_{50}$ data from J. Med. Chem. 41 (1998), 291 and 303;
$^c$"—" means compound not prepared.

TABLE 4 hPR agonist potencies (EC$_{50}$ in nM) of selected 7,9-difluoro compounds of present invention (Formula II) and analogues with other D-ring substitution patterns in the cotransfection assay.

| X → | | 7,9-diF | H | 9-F | 8-OH | 9-OH | 8-OMe | 9-OMe | 7-Cl | 9-Cl | 9-Me | 8-F | 8,9-diF |
|---|---|---|---|---|---|---|---|---|---|---|---|---|---|
| R$^9$ | # | EC$_{50}$ | EC$_{50}$ | EC$_{50}$ | EC$_{50}$ | EC$_{50}$ | EC$_{50}$ | EC$_{50}$ | EC$_{50}$ | EC$_{50}$ | EC$_{50}$ | EC$_{50}$ | EC$_{50}$ |
| Phenyl | 10 | 4.9 | 33$^a$ | 5.25 | —$^c$ | 54.4 | — | 5.5 | 67 | 6.2 | 6.24 | — | 187 | — |
| 2-F-Ph | 12 | 2.55 | 29$^b$ | 7.3 | — | — | — | 45 | — | — | 26.5 | — | — | — |
| 3-F-Ph | 15 | 3.8 | 7.6$^b$ | 7 | — | 5.75 | — | 8.6 | — | — | 11.6 | 7.95 | 109 | — |
| 4-F-Ph | 16 | 3.7 | 59.5$^b$ | 3.95 | — | — | — | — | — | — | — | — | — | — |
| 2-Cl-Ph | 13 | 1.92 | 57.8$^b$ | 12 | — | — | — | >1000 | — | — | — | — | — | — |
| 2,5-diF-Ph | 17 | 2.9 | 14.7$^b$ | 3 | 10 | 10 | — | — | — | — | 25 | — | — | — |
| 2-Me-3-F-Ph | 21 | 8.2 | — | 8.4 | — | — | — | — | — | — | — | — | — | — |
| 2-Me-5-F-Ph | 19 | 1.4 | 2.6 | 2.1 | — | — | — | — | — | — | 2.1 | — | — | 3.95 |
| 2-MeO-5-F-Ph | 26 | 0.6 | — | 0.9 | — | 11.5 | — | — | — | — | — | — | — | — |
| 2-MeO-Ph | 18 | 1.3 | — | 0.93 | — | — | — | 24.0 | — | — | — | — | — | — |
| 2-Me-Ph | 81 | 1.66 | 5.7$^b$ | 4$^a$ | — | 9.3 | — | 3.5 | 67.5 | — | 8.5 | — | 13 | 13 |
| 4-pyridinyl | 14 | 7.4 | — | 5.8 | — | — | — | 36 | — | — | — | — | — | — |
| 3-Me-4-pyridinyl | 20 | 2.8 | — | 2.0 | — | — | — | 24 | — | — | — | — | — | — |
| 2-Thienyl | 31 | 2.7 | — | 18 | — | — | — | — | — | — | — | — | — | — |

$^a$EC$_{50}$ data from U.S. Pat. Nos. 5693646/5693647/5696127;
$^b$EC$_{50}$ data from J. Med. Chem. 41 (1998), 291 and 303;
$^c$"—" means compound not prepared.

EXAMPLE 70

The 7,9-difluoro substituents at the D-ring of formulae I and II of the present invention are generally superior to any other substituents in tissue-selectivity, which is unexpected and surprising, in view of U.S. Pat. Nos. 5,693,646 and 5,696,127. The superiority of the 7,9-difluoro analogue compounds of the present invention was further characterized utilizing a multi-endpoint adult rat model according to the following illustrative Examples. In this assay, advantage is taken of the fact that in the uterus, estrogens induce a proliferation and increase in the epithelial cell height and uterine wet weight, which can be antagonized by progestins. In the breast, estrogens induce a proliferation of the ductal network while progestins stimulate the growth of the lobular-alveolar end buds, which grow from the distal end of the ducts. The assay is carried out in ovariectomized female rats by treating them for three days with estrone or estrone plus varying doses of a progestin; in this case MPA was used. Proliferating cells or inhibition of proliferating cells were quantitated either by measurements of cell height in sectioned and stained tissue samples or, in the case of the breast, immuno-histochemically labeled Brdu incorporated nuclei. The tissue-selectivity comparison between the new 7,9-difluoro compounds and analogues with substitution patterns different from 7,9-difluoro (disclosed in U.S. Pat. Nos. 5,693,646 and 5,696,127) are tabulated in Tables 5 and 6. The uterus/breast tissue-selectivity is presented as the ratio of relative efficacy to MPA in uterus verse in breast tissue at the same highest dose tested.

TABLE 5

The uterus/breast tissue-selectivity of selected 7,9-difluoro compounds of present invention (Formula I) and analogues with other D-ring substitution patterns in an adult rat model.

| $R^8$ | 7,9-diF | | H | 9-F |
|---|---|---|---|---|
| | Compd # | selectivity | selectivity | selectivity |
| Ph | 33 | —ᵃ | 0.78 | — |
| n-butyl | 52 | — | — | 2.0 |
| 2-benzo-thiophene | 64 | 2.8 | — | — |
| 4-Cl-3-Me—Ph | 38 | 2.8 | — | — |
| 1-propynyl | 75 | 4.2 | — | — |
| 4-Cl—Ph | 43 | — | 1.5 | — |
| 3-CF$_3$—Ph | 56 | — | 3.5 | — |

ᵃ"—" means compound not tested in the assay.

TABLE 6

The uterus/breast tissue-selectivity of selected 7,9-difluoro compounds of present invention (Formula II) and analogues with other D-ring substitution patterns in an adult rat model.

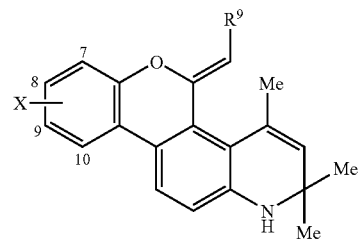

| $R^8$ | 7,9-diF | | H | 9-F |
|---|---|---|---|---|
| | Compd # | selectivity | selectivity | selectivity |
| 2,5-diF—Ph | 17 | 2.7 | —ᵃ | — |
| 3-F—Ph | 15 | — | 0.69 | 2.2 |
| 2-thienyl | 31 | 3.5 | — | — |
| 2-Me-5-F—Ph | 19 | 3.5 | — | — |
| 2-Me—Ph | 81 | — | — | 2.3 |

ᵃ"—" means compound not tested in the assay.

EXAMPLE 71

The 7,9-difluoro substituents at the D-ring of formulae I and II of the present invention are generally superior to any other substituents in PR agonist activity in vivo, which is unexpected and surprising, in view of U.S. Pat. Nos. 5,693,646 and 5,696,127. The superiority of the 7,9-difluoro analogue compounds of the present invention was further characterized utilizing the McPhail rabbit model according to the following illustrative Examples. The Clauberg or McPhail assay is a classic assay utilizing rabbits to measure progestational activity. The reason rabbit is used is because the results observed in rabbit have proved to be a good indicator and predictor of activity in the human. In this assay, immature rabbits are treated initially with estradiol, which induces growth in the uterus. This is followed by a progestin, which causes a large change in the glandular content of the uterus. It is this change in the glandular component which is a measure of the progestational activity of a progestin. The measurement of these glandular changes is carried out histologically using stained sections of the uterus. The in vivo comparison between the new 7,9-difluoro compounds and analogues with substitution patterns different from 7,9-difluoro (U.S. Pat. Nos. 5,693,646 and 5,696,127) is tabulated in Tables 7 and 8. The in vivo potency of the progestins is presented as the minimum active dose (MAD).

TABLE 7

The potency (MAD in mg/kg) of selected 7,9-difluoro compounds of present invention (Formula I) and analogues with other D-ring substitution patterns in the McPhail assay.

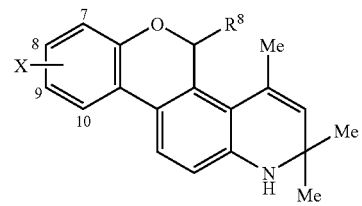

| X → | 7,9-diF | | 7-F | 9-F | 9-Me |
|---|---|---|---|---|---|
| $R^8$ | Compd # | MAD | MAD | MAD | MAD |
| 3-F—Ph | 40 | —[a] | — | — | >2 |
| 3-Me—Ph | 34 | 1.0 | — | — | — |
| 2-benzo-thiophene | 64 | 0.25 | — | — | — |
| 4-Cl-3-Me—Ph | 38 | 0.25 | 0.5 | 1.0 | — |
| 1-propynyl | 75 | <0.5 | — | — | — |
| 2-propynyl | 71 | <0.5 | — | — | — |
| 3-Cl—Ph | 41 | 0.75 | — | — | — |

[a] "—" means compound not tested in the assay.

TABLE 8

The potency (MAD in mg/kg) of selected 7,9-difluoro compounds of present invention (Formula II) and analogues with other D-ring substitution patterns in the McPhail assay.

| X → | 7,9-diF | | 7-F | 9-F |
|---|---|---|---|---|
| $R^8$ | Compd # | MAD | MAD | MAD |
| 2,5-diF—Ph | 17 | 0.25 | 0.5 | —[a] |
| 2-F—Ph | 12 | 0.5 | — | — |
| 3-F—Ph | 15 | 0.18 | — | — |
| 2-MeO—Ph | 18 | 2.0 | — | — |
| 2-Me-5-F—Ph | 19 | 0.1 | 1.0 | — |
| 2-MeO-5-F—Ph | 26 | 2.0 | — | — |
| 2-Me—Ph | 81 | — | — | 1.2 |
| 3-Me-pyridine-4- | 20 | 0.25 | — | — |

[a] "—" means compound not tested in the assay.

Pharmacological and Other Applications

The following Example provides illustrative pharmaceutical composition formulations:

EXAMPLE 72

Hard gelatin capsules are prepared using the following ingredients:

| | Quantity (mg/capsule) |
|---|---|
| COMPOUND 10 | 10 |
| Starch, dried | 200 |
| Magnesium stearate | 10 |
| Total | 220 mg |

The above ingredients are mixed and filled into hard gelatin capsules in 220 mg quantities.

A tablet is prepared using the ingredients below:

| | Quantity (mg/tablet) |
|---|---|
| COMPOUND 10 | 10 |
| Cellulose, microcrystalline | 200 |
| Silicon dioxide, fumed | 10 |
| Stearic acid | 10 |
| Total | 230 mg |

The components are blended and compressed to form tablets each weighing 230 mg.

Tablets, each containing 10 mg of active ingredient, are made as follows:

| | Quantity (mg/tablet) |
|---|---|
| COMPOUND 10 | 10 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 100 mg |

The active ingredient, starch and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate and talc, previously passed through a No. 60 mesh U.S. sieve are then added to the granules which, after mixing, are compressed on a tablet machine to yield tablets each weighing 150 mg.

Suppositories, each containing 225 mg of active ingredient, may be made as follows:

| | Quantity (mg/suppository) |
|---|---|
| COMPOUND 10 | 20 |
| Saturated fatty acid glycerides | 2,000 |
| Total | 2,020 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

An intravenous formulation may be prepared as follows:

|  | Quantity |
| --- | --- |
| COMPOUND 10 | 10 mg |
| isotonic saline | 1000 mL |
| glycerol | 100 mL |

The compound is dissolved in the glycerol and then the solution is slowly diluted with isotonic saline. The solution of the above ingredients is then administered intravenously at a rate of 1 mL per minute to a patient.

The present invention includes any combination of the various species and subgeneric groupings falling within the generic disclosure. This invention therefore includes the generic description of the invention with a proviso or negative limitation removing any subject matter from the genus, regardless of whether or not the excised material is specifically recited herein.

The scope of the invention is not limited by the description of the examples. Modifications and alterations of the present invention will be apparent to those skilled in the art without departing from the scope and spirit of the present invention.

Therefore, it will be appreciated that the scope of this invention is to be defined by the appended claims, rather than by the specific examples which have been presented by way of example.

What is claimed is:

1. A compound of the formula:

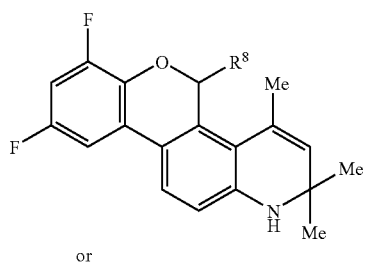

(I)

or

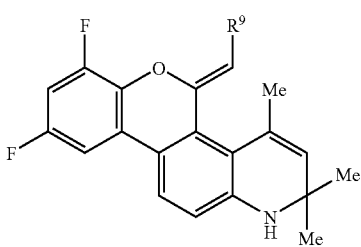

(II)

wherein:
$R^8$ is selected from the group of $C_1$–$C_{12}$ alkyl, $C_1$–$C_{12}$ heteroalkyl, $C_1$–$C_{12}$ haloalkyl, $C_2$–$C_{12}$ alkenyl, $C_2$–$C_{12}$ heteroalkenyl, $C_2$–$C_{12}$ haloalkenyl, $C_2$–$C_{12}$ alkynyl, $C_2$–$C_{12}$ heteroalkynyl, $C_2$–$C_{12}$ haloalkynyl, aryl and heteroaryl, optionally substituted with one or more substituents independently selected from the group of hydrogen, $C_1$–$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_2CH_3$, $C(O)NH_2$, $OR^{10}$, $SR^{10}$, and $NR^{10}R^{11}$;

$R^9$ is selected from the group of hydrogen, F, Cl, Br, I, CN, $C_1$–$C_8$ alkyl, $C_1$–$C_8$ heteroalkyl, $C_1$–$C_8$ haloalkyl, $C_2$–$C_8$ alkenyl or cycloalkenyl, $C_2$–$C_8$ heteroalkenyl, $C_2$–$C_8$ haloalkenyl, $C_2$–$C_8$ alkynyl, $C_2$–$C_8$ heteroalkynyl, $C_2$–$C_8$ haloalkynyl, aryl and heteroaryl, optionally substituted with one or more substituents independently selected from the group of hydrogen, $C_1$–$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_2CH_3$, $C(O)NH_2$, $OR^{10}$, $SR^{10}$, and $NR^{10}R^{11}$;

$R^{10}$ and $R^{11}$ each independently is hydrogen, or $C_1$–$C_4$ alkyl; or a pharmaceutically acceptable salt thereof.

2. A compound according to claim 1, wherein $R^8$ is selected from the group of $C_1$–$C_8$ alkyl, $C_1$–$C_8$ heteroalkyl, $C_1$–$C_8$ haloalkyl, $C_2$–$C_8$ alkenyl, $C_2$–$C_8$ heteroalkenyl, $C_2$–$C_8$ haloalkenyl, $C_2$–$C_8$ alkynyl, $C_2$–$C_8$ heteroalkynyl, $C_2$–$C_8$ haloalkynyl, aryl and heteroaryl, optionally substituted with one or more substituents independently selected from the group of hydrogen, $C_1$–$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_2CH_3$, $C(O)NH_2$, $OR^{10}$, $SR^{10}$, and $NR^{10}R^{11}$.

3. A compound according to claim 2, wherein $R^8$ is selected from the group of $C_1$–$C_4$ alkyl, $C_1$–$C_4$ heteroalkyl, $C_1$–$C_4$ haloalkyl, $C_2$–$C_4$ alkenyl, $C_2$–$C_4$ heteroalkenyl, $C_2$–$C_4$ haloalkenyl, $C_2$–$C_4$ alkynyl, $C_2$–$C_4$ heteroalkynyl, and $C_2$–$C_4$ haloalkynyl.

4. A compound according to claim 2, wherein $R^8$ selected from the group of aryl and heteroaryl radicals, wherein said aryl and heteroaryl radicals are optionally substituted with one or more substituents independently selected from the group of hydrogen, $C_1$–$C_4$ alkyl, F, Cl, Br, CN, $NH_2$, $NHCH_3$, $N(CH_3)_2$, SH, $SCH_3$, OH, $OCH_3$, $OCF_3$, $CF_3$, $C(O)CH_3$, $OR^{10}$, $SR^{10}$, and $NR^{10}R^{11}$.

5. A compound according to claim 2, wherein $R^8$ is selected from the group of

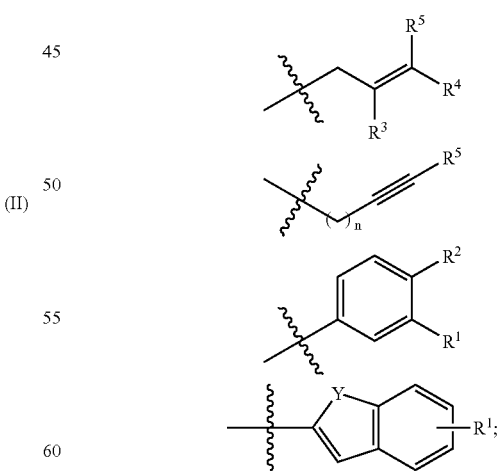

wherein:
$R^1$ and $R^2$ each independently is selected from the group of hydrogen, F, Cl, Br and $C_1$–$C_4$ alkyl;
$R^3$ through $R^5$ each independently is selected from group of hydrogen, F, Cl, and $C_1$–$C_4$ alkyl;

n is 0 or 1; and

Y is selected from the group of O, S, and $NR^{10}$.

6. A compound according to claim 1, wherein $R^9$ is selected from the group of hydrogen, F, Cl, Br, CN, $C_1$–$C_6$ alkyl, $C_1$–$C_6$ heteroalkyl, $C_1$–$C_6$ haloalkyl, $C_2$–$C_6$ alkenyl or cycloalkenyl, $C_2$–$C_6$ heteroalkenyl, $C_2$–$C_6$ haloalkenyl, $C_2$–$C_6$ alkynyl, $C_2$–$C_6$ heteroalkynyl, $C_2$–$C_6$ haloalkynyl, aryl and heteroaryl optionally substituted with one or more substituents independently selected from the group of hydrogen, $C_1$–$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_2CH_3$, $C(O)NH_2$, $OR^{10}$, $SR^{10}$, and $NR^{10}R^{11}$.

7. A compound according to claim 6, wherein $R^9$ is selected from the group of hydrogen, Br, Cl, $C_1$–$C_4$ alkyl, $C_1$–$C_4$ heteroalkyl, $C_1$–$C_4$ haloalkyl, $C_2$–$C_4$ alkenyl, $C_2$–$C_4$ heteroalkenyl, $C_2$–$C_4$ haloalkenyl, $C_2$–$C_4$ alkynyl and $C_2$–$C_4$ heteroalkynyl, $C_2$–$C_4$ haloalkynyl.

8. A compound according to claim 6, wherein $R^9$ is selected from the group of aryl and heteroaryl radicals, wherein said aryl and heteroaryl radicals are optionally substituted with one or more substituents independently selected from the group of hydrogen, $C_1$–$C_4$ alkyl, F, Cl, Br, CN, $NH_2$, $NHCH_3$, $N(CH_3)_2$, SH, $SCH_3$, OH, $OCH_3$, $OCF_3$, $OR^{10}$, $SR^{10}$, and $NR^{10}R^{11}$.

9. A compound according to claim 6, wherein R9 is selected from the group of

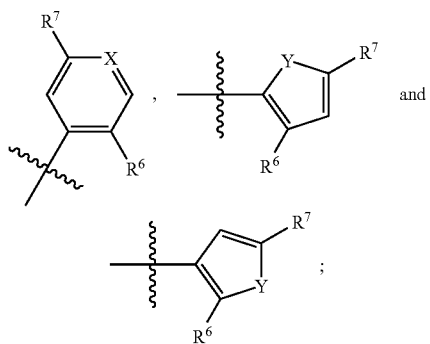

wherein:
$R^6$ is selected from the group of hydrogen, F, Cl, Br, $C_1$–$C_4$ alkyl, $OR^{10}$, $SR^{10}$, and $NR^{10}R^{11}$;
$R^7$ is hydrogen, F, or Cl;
$R^{10}$ and $R^{11}$ each independently is hydrogen, or $C_1$–$C_4$ alkyl;
X is CH or N; and
Y is selected from the group of O, S, and $NR^{10}$.

10. A compound according to claim 9, wherein:
$R^9$ is

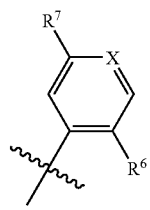

$R^6$ is selected from the group of hydrogen, F, Cl, $C_1$–$C_4$ alkyl, OMe, OEt, NHMe, and $NMe_2$;
$R^7$ is hydrogen, F, or Cl; and
X is CH or N.

11. A compound according to claim 9, where $R^6$ is selected from the group of F, Me, Et, OMe, OEt, SMe, and $NMe_2$.

12. A compound according to claim 1, wherein said compound is selected from the group of:

7,9-difluoro-5(Z)-benzylidene-1,2-dihydro-2,2,4-trimethyl-5H-chromeno[3,4-f]quinoline (Compound 10);

7,9-difluoro-5(Z)-(2-fluorobenzylidene)-1,2-dihydro-2,2,4-trimethyl-5H-chromeno[3,4-f]quinoline (Compound 12);

7,9-difluoro-5(Z)-(2-chlorobenzylidene)-1,2-dihydro-2,2,4-trimethyl-5H-chromeno [3,4-f]quinoline (Compound 13);

7,9-difluoro-5(Z)-(4-picolylidene)-1,2-dihydro-2,2,4-trimethyl-5H-chromeno [3,4-f]quinoline (Compound 14);

7,9-difluoro-5(Z)-(3-fluorobenzylidene)-1,2-dihydro-2,2,4-trimethyl-5H-chromeno [3,4-f]quinoline (Compound 15);

7,9-difluoro-5(Z)-(4-fluorobenzylidene)-1,2-dihydro-2,2,4-trimethyl-5H-chromeno [3,4-f]quinoline (Compound 16);

7,9-difluoro-5(Z)-(2,5-difluorobenzylidene)-1,2-dihydro-2,2,4-trimethyl-5H-chromeno [3,4-f]quinoline (Compound 17);

7,9-difluoro-5(Z)-(2-methoxybenzylidene)-1,2-dihydro-2,2,4-trimethyl-5H-chromeno [3,4-f]quinoline (Compound 18);

7,9-difluoro-5(Z)-(2-methyl-5-fluorobenzylidene)-1,2-dihydro-2,2,4-trimethyl-5H-chromeno [3,4-f]quinoline (Compound 19);

7,9-difluoro-5(Z)-(3-methyl-4-picolylidene)-1,2-dihydro-2,2,4-trimethyl-5H-chromeno [3,4-f]quinoline (Compound 20);

7,9-difluoro-5(Z)-(2-methyl-3-fluorobenzylidene)-1,2-dihydro-2,2,4-trimethyl-5H-chromeno [3,4-f]quinoline (Compound 21);

7,9-difluoro-5(Z)-(3-methyl-2-picolylidene)-1,2-dihydro-2,2,4-trimethyl-5H-chromeno [3,4-f]quinoline (Compound 22);

7,9-difluoro-5(Z)-(2,3-dimethylbenzylidene)-1,2-dihydro-2,2,4-trimethyl-5H-chromeno [3,4-f]quinoline (Compound 23);

7,9-difluoro-5(Z)-cyanomethylidene-1,2-dihydro-2,2,4-trimethyl-5H-chromeno [3,4-f]quinoline (Compound 24);

7,9-difluoro-5(Z)-hexylidene-1,2-dihydro-2,2,4-trimethyl-5H-chromeno [3,4-f]quinoline (Compound 25);

7,9-difluoro-5(Z)-(2-methoxy-5-fluorobenzylidene)-1,2-dihydro-2,2,4-trimethyl-5H-chromeno [3,4-f]quinoline (Compound 26);

7,9-difluoro-5(Z)-(2,4,5-trifluorobenzylidene)-1,2-dihydro-2,2,4-trimethyl-5H-chromeno [3,4-f]quinoline (Compound 27);

7,9-difluoro-5-methylidene-1,2-dihydro-2,2,4-trimethyl-5H-chromeno [3,4-f]quinoline (Compound 28);

7,9-difluoro-5(Z)-bromomethylidene-1,2-dihydro-2,2,4-trimethyl-5H-chromeno [3,4-f]quinoline (Compound 29);

7,9-difluoro-5(Z)-(3-thienylmethylidene)-1,2-dihydro-2,2,4-trimethyl-5H-chromeno [3,4-f]quinoline (Compound 30);

7,9-difluoro-5(Z)-(2-thienylmethylidene)-1,2-dihydro-2,2,4-trimethyl-5H-chromeno [3,4-f]quinoline (Compound 31);

(±)-7,9-difluoro-5-methoxy-1,2-dihydro-2,2,4-trimethyl-5H-chromeno [3,4-f]quinoline (Compound 32);

(±)-7,9-difluoro-5-phenyl-1,2-dihydro-2,2,4-trimethyl-5H-chromeno [3,4-f]quinoline (Compound 33);

(±)-7,9-difluoro-5-(3-methylphenyl)-1,2-dihydro-2,2,4-trimethyl-5H-chromeno [3,4-f]quinoline (Compound 34);

(±)-7,9-difluoro-5-(1,3-benzodioxol-5-yl)-1,2-dihydro-2,2,4-trimethyl-5H-chromeno [3,4-f]quinoline (Compound 35);

(±)-7,9-difluoro-5-(4-bromophenyl)-1,2-dihydro-2,2,4-trimethyl-5H-chromeno [3,4-f]quinoline (Compound 36);

(±)-7,9-difluoro-5-(4-chloro-3-methylphenyl)-1,2-dihydro-2,2,4-trimethyl-5H-chromeno [3,4-f]quinoline (Compound 37);

(−)-7,9-difluoro-5-(4-chloro-3-methylphenyl)-1,2-dihydro-2,2,4-trimethyl-5H-chromeno [3,4-f]quinoline (Compound 38);

(+)-7,9-difluoro-5-(4-chloro-3-methylphenyl)-1,2-dihydro-2,2,4-trimethyl-5H-chromeno [3,4-f]quinoline (Compound 39);

(±)-7,9-difluoro-5-(3-fluorophenyl)-1,2-dihydro-2,2,4-trimethyl-5H-chromeno [3,4-f]quinoline (Compound 40);

(±)-7,9-difluoro-5-(3-chlorophenyl)-1,2-dihydro-2,2,4-trimethyl-5H-chromeno [3,4-f]quinoline (Compound 41);

(±)-7,9-difluoro-5-(3-bromophenyl)-1,2-dihydro-2,2,4-trimethyl-5H-chromeno [3,4-f]quinoline (Compound 42);

(±)-7,9-difluoro-5-(4-chlorophenyl)-1,2-dihydro-2,2,4-trimethyl-5H-chromeno [3,4-f]quinoline (Compound 43);

(±)-7,9-difluoro-1,2-dihydro-2,2,4,5-tetramethyl-5H-chromeno [3,4-f]quinoline (Compound 44);

(±)-7,9-difluoro-5-(2-oxo-2-phenylethyl)-1,2-dihydro-2,2,4-trimethyl-5H-chromeno [3,4-f]quinoline (Compound 45);

(±)-7,9-difluoro-5-ethyl-1,2-dihydro-2,2,4-trimethyl-5H-chromeno [3,4-f]quinoline (Compound 46);

(±)-7,9-difluoro-5-ethenyl-1,2-dihydro-2,2,4-trimethyl-5H-chromeno [3,4-f]quinoline (Compound 47);

(±)-7,9-difluoro-5-(2-oxo-3-butenyl)-1,2-dihydro-2,2,4-trimethyl-5H-chromeno [3,4-f]quinoline (Compound 48);

(±)-7,9-difluoro-1,2-dihydro-α,α,2,2,4-pentamethyl-5H-chromeno [3,4-f]quinoline-5-ethanoate (Compound 49);

(±)-7,9-difluoro-5-ethynyl-1,2-dihydro-2,2,4-trimethyl-5H-chromeno [3,4-f]quinoline (Compound 50);

(±)-7,9-difluoro-5-cyano-1,2-dihydro-2,2,4-trimethyl-5H-chromeno [3,4-f]quinoline (Compound 51);

(±)-7,9-difluoro-5-butyl-1,2-dihydro-2,2,4-trimethyl-5H-chromeno [3,4-f]quinoline (Compound 52);

(±)-7,9-difluoro-5-(2-thienyl)-1,2-dihydro-2,2,4-trimethyl-5H-chromeno [3,4-f]quinoline (Compound 53);

(±)-7,9-difluoro-5-(2-furyl)-1,2-dihydro-2,2,4-trimethyl-5H-chromeno [3,4-f]quinoline (Compound 54);

(±)-7,9-difluoro-5-allyl-1,2-dihydro-2,2,4-trimethyl-5H-chromeno [3,4-f]quinoline (Compound 55);

(±)-7,9-difluoro-5-[3-(trifluoromethyl)phenyl]-1,2-dihydro-2,2,4-trimethyl-5H-chromeno [3,4-f]quinoline (Compound 56);

Ethyl (±)-7,9-difluoro-1,2-dihydro-α-methylene-2,2,4-trimethyl-5H-chromeno [3,4-f]quinoline-5-propanoate (Compound 57);

(±)-7,9-difluoro-1,2-dihydro-β-methylene-2,2,4-trimethyl-5H-chromeno [3,4-f]quinoline-5-propanol (Compound 58);

(±)-7,9-difluoro-1,2-dihydro-β-methylene-2,2,4-trimethyl-5H-chromeno [3,4-f]quinoline-5-propanol acetate (Compound 59);

(±)-7,9-difluoro-5-(1-methylethenyl)-1,2-dihydro-2,2,4-trimethyl-5H-chromeno [3,4-f]quinoline (Compound 60);

(±)-7,9-difluoro-5-(N-methyl-2-pyrrolyl)-1,2-dihydro-2,2,4-trimethyl-5H-chromeno [3,4-f]quinoline (Compound 61);

(±)-7,9-difluoro-5-phenylethynyl-1,2-dihydro-2,2,4-trimethyl-5H-chromeno [3,4-f]quinoline (Compound 62);

(±)-7,9-difluoro-5-(benzo[b]thien-2-yl)-1,2-dihydro-2,2,4-trimethyl-5H-chromeno [3,4-f]quinoline (Compound 63);

(−)-7,9-difluoro-5-(benzo[b]thien-2-yl)-1,2-dihydro-2,2,4-trimethyl-5H-chromeno [3,4-f]quinoline (Compound 64);

(+)-7,9-difluoro-5-(benzo[b]thie-2yl)-1,2-dihydro-2,2,4-trimethyl-5H-chromeno [3,4-f]quinoline (Compound 65);

(±)-7,9-difluoro-5-(5-methyl-2-furyl)-1,2-dihydro-2,2,4-trimethyl-5H-chromeno [3,4-f]quinoline (Compound 66);

(±)-7,9-difluoro-5-(2-benzo[b]furyl)-1,2-dihydro-2,2,4-trimethyl-5H-chromeno [3,4-f]quinoline (Compound 67);

(±)-7,9-difluoro-5-[4-(dimethylamino)phenyl]-1,2-dihydro-2,2,4-trimethyl-5H-chromeno [3,4-f]quinoline (Compound 68);

(±)-7,9-difluoro-5-(5-methyl-2-thienyl)-1,2-dihydro-2,2,4-trimethyl-5H-chromeno [3,4-f]quinoline (Compound 69);

(±)-7,9-difluoro-5-(5-methoxy-2-furyl)-1,2-dihydro-2,2,4-trimethyl-5H-chromeno [3,4-f]quinoline (Compound 70);

(±)-7,9-difluoro-5-(2-propynyl)-1,2-dihydro-2,2,4-trimethyl-5H-chromeno [3,4-f]quinoline (Compound 71);

(−)-7,9-difluoro-5-(2-propynyl)-1,2-dihydro-2,2,4-trimethyl-5H-chromeno [3,4-f]quinoline (Compound 72);

(+)-7,9-difluoro-5-(2-propynyl)-1,2-dihydro-2,2,4-trimethyl-5H-chromeno [3,4-f]quinoline (Compound 73);

(±)-7,9-difluoro-5-(1-propynyl)-1,2-dihydro-2,2,4-trimethyl-5H-chromeno [3,4-f]quinoline (Compound 74);

(−)-7,9-difluoro-5-(1-propynyl)-1,2-dihydro-2,2,4-trimethyl-5H-chromeno [3,4-f]quinoline (Compound 75);

(+)-7,9-difluoro-5-(1-propynyl)-1,2-dihydro-2,2,4-trimethyl-5H-chromeno [3,4-f]quinoline (Compound 76);

(±)-7,9-difluoro-5-(4,5-dimethyl-2-furyl)-1,2-dihydro-2,2,4-trimethyl-5H-chromeno [3,4-f]quinoline (Compound 77);

(±)-7,9-difluoro-5-(2-methyl-1-propenyl)-1,2-dihydro-2,2,4-trimethyl-5H-chromeno [3,4-f]quinoline (Compound 78);

(±)-7,9-difluoro-5-(3,4-dimethyl-2-thienyl)-1,2-dihydro-2,2,4-trimethyl-5H-chromeno [3,4-f]quinoline (Compound 79);

(±)-7,9-difluoro-5-(3-(3-bromophenyl)phenyl)-1,2-dihydro-2,2,4-trimethyl-5H-chromeno [3,4-f]quinoline (Compound 80); and 7,9-difluoro-5-(2-methylbenzylidene)-1,2-dihydro-2,2,4-trimethyl-5H-chromeno [3,4-f]quinoline (Compound 81).

13. A compound according to claim 1, wherein said compound is selected from the group of:

7,9-difluoro-5(Z)-benzylidene-1,2-dihydro-2,2,4-trimethyl-5H-chromeno [3,4-f]quinoline (Compound 10);

7,9-difluoro-5(Z)-(2-fluorobenzylidene)-1,2-dihydro-2,2,4-trimethyl-5H-chromeno [3,4-f]quinoline (Compound 12);

7,9-difluoro-5(Z)-(3-fluorobenzylidene)-1,2-dihydro-2,2,4-trimethyl-5H-chromeno [3,4-f]quinoline (Compound 15);

7,9-difluoro-5(Z)-(2,5-difluorobenzylidene)-1,2-dihydro-2,2,4-trimethyl-5H-chromeno [3,4-f]quinoline (Compound 17);

7,9-difluoro-5(Z)-(2-methoxybenzylidene)-1,2-dihydro-2,2,4-trimethyl-5H-chromeno [3,4-f]quinoline (Compound 18);

7,9-difluoro-5(Z)-(2-methyl-5-fluorobenzylidene)-1,2-dihydro-2,2,4-trimethyl-5H-chromeno [3,4-f]quinoline (Compound 19);

7,9-difluoro-5(Z)-(3-methyl-4-picolylidene)-1,2-dihydro-2,2,4-trimethyl-5H-chromeno [3,4-f]quinoline (Compound 20);

7,9-difluoro-5(Z)-(2-methoxy-5-fluorobenzylidene)-1,2-dihydro-2,2,4-trimethyl-5H-chromeno [3,4-f]quinoline (Compound 26);

7,9-difluoro-5(Z)-(3-thienylmethylidene)-1,2-dihydro-2,2,4-trimethyl-5H-chromeno [3,4-f]quinoline (Compound 30);

7,9-difluoro-5(Z)-(2-thienylmethylidene)-1,2-dihydro-2,2,4-trimethyl-5H-chromeno [3,4-f]quinoline (Compound 31);

(±)-7,9-difluoro-5-(3-methylphenyl)-1,2-dihydro-2,2,4-trimethyl-5H-chromeno [3,4-f]quinoline (Compound 34);

(−)-7,9-difluoro-5-(4-chloro-3-methylphenyl)-1,2-dihydro-2,2,4-trimethyl-5H-chromeno [3,4-f]quinoline (Compound 38);

(±)-7,9-difluoro-5-(3-chlorophenyl)-1,2-dihydro-2,2,4-trimethyl-5H-chromeno [3,4-f]quinoline (Compound 41);

(±)-7,9-difluoro-1,2-dihydro-2,2,4,5-tetramethyl-5H-chromeno [3,4-f]quinoline (Compound 44);

(±)-7,9-difluoro-5-allyl-1,2-dihydro-2,2,4-trimethyl-5H-chromeno [3,4-f]quinoline (Compound 55);

(+)-7,9-difluoro-5-(3-trifluoromethylphenyl)-1,2-dihydro-2,2,4-trimethyl-5H-chromeno [3,4-f]quinoline (Compound 56);

(±)-7,9-difluoro-5-(benzo[b]thien-2-yl)-1,2-dihydro-2,2,4-trimethyl-5H-chromeno [3,4-f]quinoline (Compound 63);

(−)-7,9-difluoro-5-(benzo[b]thien-2-yl)-1,2-dihydro-2,2,4-trimethyl-5H-chromeno [3,4-f]quinoline (Compound 64);

(+)-7,9-difluoro-5-(benzo[b]thien-2-yl)-1,2-dihydro-2,2,4-trimethyl-5H-chromeno [3,4-f]quinoline (Compound 65);

(−)-7,9-difluoro-5-(2-propynyl)-1,2-dihydro-2,2,4-trimethyl-5H-chromeno [3,4-f]quinoline (Compound 72);

(−)-7,9-difluoro-5-(1-propynyl)-1,2-dihydro-2,2,4-trimethyl-5H-chromeno [3,4-f]quinoline (Compound 75); and 7,9-difluoro-5-(2-methylbenzylidene)-1,2-dihydro-2,2,4-trimethyl-5H-chromeno [3,4-f]quinoline (Compound 81).

14. A compound according to claim 1, wherein said compound is selected from the group of:

7,9-difluoro-5(Z)-(2,5-difluorobenzylidene)-1,2-dihydro-2,2,4-trimethyl-5H-chromeno [3,4-f]quinoline (Compound 17);

7,9-difluoro-5(Z)-(2-methyl-5-fluorobenzylidene)-1,2-dihydro-2,2,4-trimethyl-5H-chromeno [3,4-f]quinoline (Compound 19);

7,9-difluoro-5(Z)-(3-methyl-4-picolylidene)-1,2-dihydro-2,2,4-trimethyl-5H-chromeno [3,4-f]quinoline (Compound 20);

7,9-difluoro-5(Z)-(2-methoxy-5-fluorobenzylidene)-1,2-dihydro-2,2,4-trimethyl-5H-chromeno [3,4-f]quinoline (Compound 26);

(−)-7,9-difluoro-5-(4-chloro-3-methylphenyl)-1,2-dihydro-2,2,4-trimethyl-5H-chromeno [3,4-f]quinoline (Compound 38);

(±)-7,9-difluoro-5-(benzo[b]thien-2-yl)-1,2-dihydro-2,2,4-trimethyl-5H-chromeno [3,4-f]quinoline (Compound 63);

(−)-7,9-difluoro-5-(benzo[b]thien-2-yl)-1,2-dihydro-2,2,4-trimethyl-5H-chromeno [3,4-f]quinoline (Compound 64);

(+)-7,9-difluoro-5-(benzo[b]thien-2-yl)-1,2-dihydro-2,2,4-trimethyl-5H-chromeno [3,4-f]quinoline (Compound 65); and (−)-7,9-difluoro-5-(2-propynyl)-1,2-dihydro-2,2,4-trimethyl-5H-chromeno [3,4-f]quinoline (Compound 72).

15. A pharmaceutical composition comprising a pharmaceutically acceptable carrier and a compound of formula:

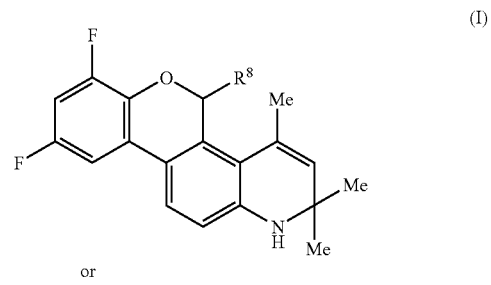

(I)

or

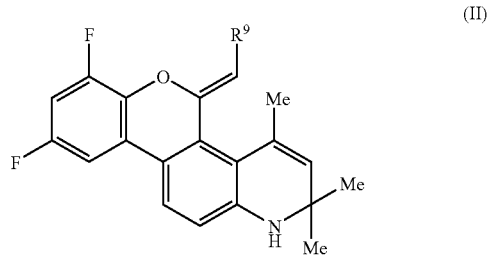

(II)

wherein:

$R^8$ is selected from the group of $C_1$–$C_{12}$ alkyl, $C_1$–$C_{12}$ heteroalkyl, $C_1$–$C_{12}$ haloalkyl, $C_2$–$C_{12}$ alkenyl, $C_2$–$C_{12}$ heteroalkenyl, $C_2$–$C_{12}$ haloalkenyl, $C_2$–$C_{12}$ alkynyl, $C_2$–$C_{12}$ heteroalkynyl, $C_2$–$C_{12}$ haloalkynyl, aryl and heteroaryl optionally substituted with one or more substituents independently selected from the group of hydrogen, $C_1$–$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_2CH_3$, $C(O)NH_2$, $OR^{10}$, $SR^{10}$, and $NR^{10}R^{11}$;

R⁹ is selected from the group of hydrogen, F, Cl, Br, I, CN, $C_1$–$C_8$ alkyl, $C_1$–$C_8$ heteroalkyl, $C_1$–$C_8$ haloalkyl, $C_2$–$C_8$ alkenyl or cycloalkenyl, $C_2$–$C_8$ heteroalkenyl, $C_2$–$C_8$ haloalkenyl, $C_2$–$C_8$ alkynyl, $C_2$–$C_8$ heteroalkynyl, $C_2$–$C_8$ haloalkynyl, aryl and heteroaryl optionally substituted with one or more substituents independently selected from the group of hydrogen, $C_1$–$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_2CH_3$, $C(O)NH_2$, $OR^{10}$, $SR^{10}$, and $NR^{10}R^{11}$; and
R¹⁰ and R¹¹ each independently is hydrogen, or $C_1$–$C_4$ alkyl; or a pharmaceutically acceptable salt thereof.

16. A pharmaceutical composition according to claim 15, wherein R⁸ is selected from the group of $C_1$–$C_8$ alkyl, $C_1$–$C_8$ heteroalkyl, $C_1$–$C_8$ haloalkyl, $C_2$–$C_8$ alkenyl, $C_2$–$C_8$ heteroalkenyl, $C_2$–$C_8$ haloalkenyl, $C_2$–$C_8$ alkynyl, $C_2$–$C_8$ heteroalkynyl, $C_2$–$C_8$ haloalkynyl, aryl and heteroaryl, optionally substituted with one or more substituents independently selected from the group of hydrogen, $C_1$–$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_2CH_3$, $C(O)NH_2$, $OR^{10}$, $SR^{10}$, and $NR^{10}R^{11}$.

17. A pharmaceutical composition according to claim 16, wherein R⁸ is selected from the group of $C_1$–$C_4$ alkyl, $C_1$–$C_4$ heteroalkyl, $C_1$–$C_4$ haloalkyl, $C_2$–$C_4$ alkenyl, $C_2$–$C_4$ heteroalkenyl, $C_2$–$C_4$ haloalkenyl, and $C_2$–$C_4$ alkynyl, $C_2$–$C_4$ heteroalkynyl and $C_2$–$C_4$ haloalkynyl.

18. A pharmaceutical composition according to claim 16, wherein R⁸ is selected from the group of aryl and heteroaryl radicals, wherein said aryl and heteroaryl radicals are optionally substituted with one or more substituents independently selected from the group of hydrogen, $C_1$–$C_4$ alkyl, F, Cl, Br, CN, $NH_2$, $NHCH_3$, $N(CH_3)_2$, SH, $SCH_3$, OH, $OCH_3$, $OCF_3$, $CF_3$, $C(O)CH_3$, $OR^{10}$, $SR^{10}$, and $NR^{10}R^{11}$.

19. A pharmaceutical composition according to claim 16, wherein R⁸ is selected from the group of

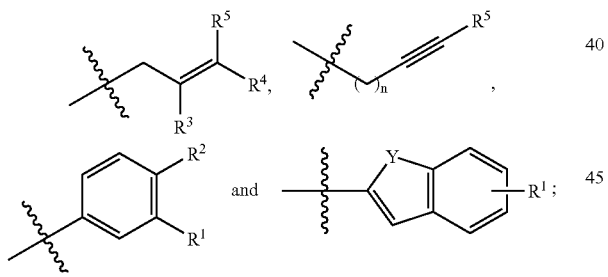

wherein:
R¹ and R² each independently is selected from the group of hydrogen, F, Cl, Br and $C_1$–$C_4$ alkyl;
R³ through R⁵ each independently is selected from the group of hydrogen, F, Cl, and $C_1$–$C_4$ alkyl;
n is 0 or 1; and
Y is selected from the group of O, S, and $NR^{10}$.

20. A pharmaceutical composition according to claim 15, wherein R⁹ is selected from the group of hydrogen, F, Cl, Br, CN, $C_1$–$C_6$ alkyl, $C_1$–$C_6$ heteroalkyl, $C_1$–$C_6$ haloalkyl, $C_2$–$C_6$ alkenyl or cycloalkenyl, $C_2$–$C_6$ heteroalkenyl, $C_2$–$C_6$ haloalkenyl, $C_2$–$C_6$ alkynyl, $C_2$–$C_6$ heteroalkynyl, $C_2$–$C_6$ haloalkynyl, aryl and heteroaryl, optionally substituted with one or more substituents independently selected from the group of hydrogen, $C_1$–$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_{2CH3}$, $C(O)NH_2$, $OR^{10}$, $SR^{10}$, and $NR^{10}R^{11}$.

21. A pharmaceutical composition according to claim 20, wherein R⁹ is selected from the group of hydrogen, Br, Cl, $C_1$–$C_4$ alkyl, $C_1$–$C_4$ heteroalkyl, $C_1$–$C_4$ haloalkyl, $C_2$–$C_4$ alkenyl, $C_2$–$C_4$ heteroalkenyl, $C_2$–$C_4$ haloalkenyl, $C_2$–$C_4$ alkynyl, $C_2$–$C_4$ heteroalkynyl, and $C_2$–$C_4$ haloalkynyl.

22. A pharmaceutical composition according to claim 20, wherein R⁹ is selected from the group of aryl and heteroaryl radicals, wherein said aryl and heteroaryl radicals are optionally substituted with one or more substituents independently selected from the group of hydrogen, $C_1$–$C_4$ alkyl, F, Cl, Br, CN, $NH_2$, $NHCH_3$, $N(CH_3)_2$, SH, $SCH_3$, OH, $OCH_3$, $OCF_3$, $OR^{10}$, $SR^{10}$, and $NR^{10}R^{11}$.

23. A pharmaceutical composition according to claim 22, wherein R⁹ is selected from the group of

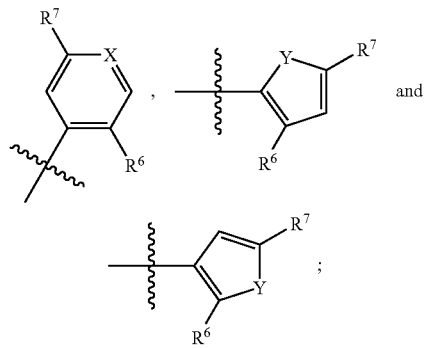

wherein:
R⁶ is selected from the group of hydrogen, F, Cl, Br, $C_1$–$C_4$ alkyl, $OR^{10}$, $SR^{10}$, and $NR^{10}R^{11}$;
R⁷ is hydrogen, F, or Cl;
R¹⁰ and R¹¹ each independently is hydrogen, or $C_1$–$C_4$ alkyl;
X is CH or N; and
Y is selected from group of O, S, and $NR^{10}$.

24. A pharmaceutical composition according to claim 23, wherein R⁹ is

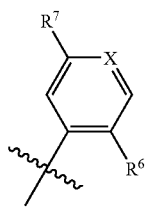

wherein
R⁶ is selected from the group of hydrogen, F, Cl, $C_1$–$C_4$ alkyl, OMe, OEt, NHMe, and $NMe_2$; and
R⁷ is hydrogen, F, or Cl.

25. A pharmaceutical composition according to claim 23, where R⁶ is selected from the group of F, Me, Et, OMe, OEt, SMe, and $NMe_2$.

* * * * *

UNITED STATES PATENT AND TRADEMARK OFFICE
CERTIFICATE OF CORRECTION

PATENT NO. : 7,163,946 B2
APPLICATION NO. : 10/684212
DATED : January 16, 2007
INVENTOR(S) : Lin Zhi et al.

It is certified that error appears in the above-identified patent and that said Letters Patent is hereby corrected as shown below:

IN THE TITLE PAGES:
In Item [56] References Cited, in OTHER PUBLICATIONS:
in Chemical Abstracts, vol. 87, No. 13, please replace "Migachev,et al." with
--Migachev, et al.--
in Database CAPLUS, Chemical Abstracts AN=1975:111718, please replace "1295" with --1292--
in Database CAPLUS, Chemical Abstracts AN=118:147477, please replace "Preparationof" with --Preparation of--
in Database Crossfire Beilstein 'Online!, XP 002002690, please replace "101-101" with --100-101--
in Database Crossfire Beilstein 'Online!, XP 002002692, please replace "'Online!0" with --'Online!,-- and please replace "457" with --57--
in Database Crossfire Beilstein 'Online!, XP 022002695, please replace "48005330" with --4800533,--
in Samsonova et al., please replace "et l.," with --et al.,--

At column 7, in Table A, row 1, please replace "$R_1$" with --$R^1$--
at column 7, in Table A, row 2, please replace "$R_2$" with --$R^2$--
at column 7, in Table A, row 3, please replace "$R_3$" with --$R^3$--
at column 7, in Table A, row 4, please replace "$R_4$" with --$R^4$--
at column 7, in Table A, row 5, please replace "$R_5$" with --$R^5$--
at column 7, in Table A, row 6, please replace "$R_6$" with --$R^6$--
at column 7, in Table A, row 7, please replace "$R_7$" with --$R^7$--
at column 7, in Table A, row 8, please replace "$R_8$" with --$R^8$--
at column 7, in Table A, row 9, please replace "$R_9$" with --$R^9$--
at column 7, in Table A, row 10, please replace "$R_{10}$" with --$R^{10}$--
at column 7, in Table A, row 11, please replace "$R_{11}$" with --$R^{11}$--

Please replace Claims 1, 5, 9, 11, 12, 13, 20 and 23 with the following Claims:

--1. A compound of the formula:

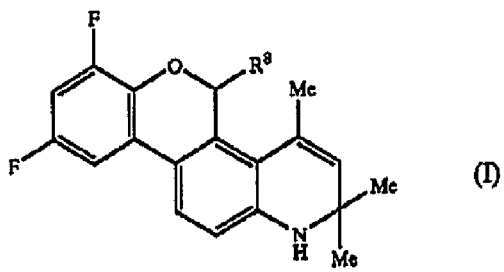

UNITED STATES PATENT AND TRADEMARK OFFICE
CERTIFICATE OF CORRECTION

PATENT NO.       : 7,163,946 B2
APPLICATION NO.  : 10/684212
DATED            : January 16, 2007
INVENTOR(S)      : Lin Zhi et al.

It is certified that error appears in the above-identified patent and that said Letters Patent is hereby corrected as shown below:

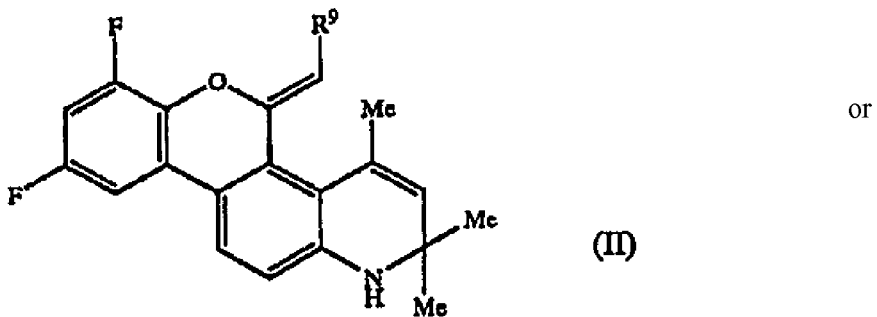

or (II)

wherein:

$R^8$ is selected from the group of $C_1$-$C_{12}$ alkyl, $C_1$-$C_{12}$ heteroalkyl, $C_1$-$C_{12}$ haloalkyl, $C_2$-$C_{12}$ alkenyl, $C_2$-$C_{12}$ heteroalkenyl, $C_2$-$C_{12}$ haloalkenyl, $C_2$-$C_{12}$ alkynyl, $C_2$-$C_{12}$ heteroalkynyl, $C_2$-$C_{12}$ haloalkynyl, aryl and heteroaryl, optionally substituted with one or more substituents independently selected from the group of hydrogen, $C_1$-$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_2CH_3$, $C(O)NH_2$, $OR^{10}$, $SR^{10}$, and $NR^{10}R^{11}$;

$R^9$ is selected from the group of hydrogen, F, Cl, Br, I, CN, $C_1$-$C_8$ alkyl, $C_1$-$C_8$ heteroalkyl, $C_1$-$C_8$ haloalkyl, $C_2$-$C_8$ alkenyl or cycloalkenyl, $C_2$-$C_8$ heteroalkenyl, $C_2$-$C_8$ haloalkenyl, $C_2$-$C_8$ alkynyl, $C_2$-$C_8$ heteroalkynyl, $C_2$-$C_8$ haloalkynyl, aryl and heteroaryl, optionally substituted with one or more substituents independently selected from the group of hydrogen, $C_1$-$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_2CH_3$, $C(O)NH_2$, $OR^{10}$, $SR^{10}$, and $NR^{10}R^{11}$;

$R^{10}$ and $R^{11}$ each independently is hydrogen, or $C_1$-$C_4$ alkyl; or a pharmaceutically acceptable salt thereof.

5. A compound according to claim 2, wherein $R^8$ is selected from the group of

UNITED STATES PATENT AND TRADEMARK OFFICE
CERTIFICATE OF CORRECTION

PATENT NO. : 7,163,946 B2  
APPLICATION NO. : 10/684212  
DATED : January 16, 2007  
INVENTOR(S) : Lin Zhi et al.

It is certified that error appears in the above-identified patent and that said Letters Patent is hereby corrected as shown below:

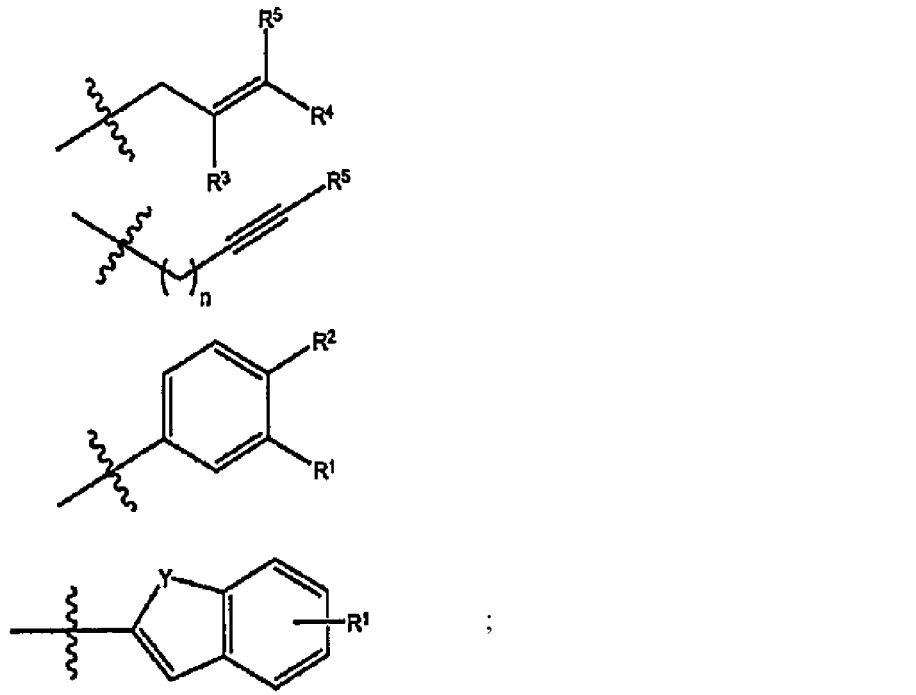

wherein:
$R^1$ and $R^2$ each independently is selected from the group of hydrogen, F, Cl, Br and $C_1$-$C_4$ alkyl;
$R^3$ through $R^5$ each independently is selected from the group of hydrogen, F, Cl, and $C_1$-$C_4$ alkyl;
n is 0 or 1; and
Y is selected from the group of O, S, and $NR^{10}$.

9. A compound according to claim 6, wherein $R^9$ is selected from the group of

UNITED STATES PATENT AND TRADEMARK OFFICE
CERTIFICATE OF CORRECTION

PATENT NO. : 7,163,946 B2
APPLICATION NO. : 10/684212
DATED : January 16, 2007
INVENTOR(S) : Lin Zhi et al.

It is certified that error appears in the above-identified patent and that said Letters Patent is hereby corrected as shown below:

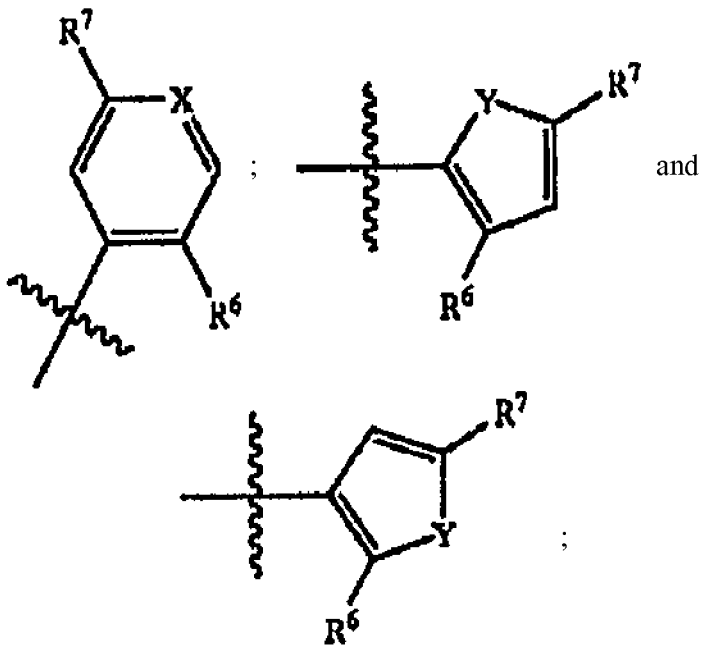

wherein:
$R^6$ is selected from the group of hydrogen, F, Cl, Br, $C_1$-$C_4$ alkyl, $OR^{10}$, $SR^{10}$, and $NR^{10}R^{11}$;
$R^7$ is hydrogen, F, or Cl;
$R^{10}$ and $R^{11}$ each independently is hydrogen, or $C_1$-$C_4$ alkyl;
X is CH or N; and
Y is selected from the group of O, S, and $NR^{10}$.

11. A compound according to claim 9, wherein $R^6$ is selected from the group of F, Me, Et, OMe, OEt, SMe, and $NMe_2$.

12. A compound according to claim 1, wherein said compound is selected from the group of:
7,9-difluoro-5(Z)-benzylidene-1,2-dihydro-2,2,4-trimethyl-5H-chromeno[3,4-*f*]-quinoline (Compound 10);
7,9-difluoro-5(Z)-(2-fluorobenzylidene)-1,2-dihydro-2,2,4-trimethyl-5H-chromeno-[3,4-*f*]-quinoline (Compound 12);
7,9-difluoro-5(Z)-(2-chlorobenzylidene)-1,2-dihydro-2,2,4-trimethyl-5H-chromeno-[3,4-*f*]quinoline (Compound 13);

UNITED STATES PATENT AND TRADEMARK OFFICE
CERTIFICATE OF CORRECTION

PATENT NO. : 7,163,946 B2
APPLICATION NO. : 10/684212
DATED : January 16, 2007
INVENTOR(S) : Lin Zhi et al.

It is certified that error appears in the above-identified patent and that said Letters Patent is hereby corrected as shown below:

7,9-difluoro-5(Z)-(4-picolylidene)-1,2-dihydro-2,2,4-trimethyl-5H-chromeno [3,4-*f*]-quinoline (Compound 14);
7,9-difluoro-5(Z)-(3-fluorobenzylidene)-1,2-dihydro-2,2,4-trimethyl-5H-chromeno-[3,4-*f*]quinoline (Compound 15);
7,9-difluoro-5(Z)-(4-fluorobenzylidene)-1,2-dihydro-2,2,4-trimethyl-5H-chromeno-[3,4-*f*]quinoline (Compound 16);
7,9-difluoro-5(Z)-(2,5-difluorobenzylidene)-1,2-dihydro-2,2,4-trimethyl-5H-chromeno-[3,4-*f*]quinoline (Compound 17);
7,9-difluoro-5(Z)-(2-methoxybenzylidene)-1,2-dihydro-2,2,4-trimethyl-5H-chromeno-[3,4-*f*]quinoline (Compound 18);
7,9-difluoro-5(Z)-(2-methyl-5-fluorobenzylidene)-1,2-dihydro-2,2,4-trimethyl-5H-chromeno[3,4-*f*]quinoline (Compound 19);
7,9-difluoro-5(Z)-(3-methyl-4-picolylidene)-1,2-dihydro-2,2,4-trimethyl-5H-chromeno[3,4-*f*]quinoline (Compound 20);
7,9-difluoro-5(Z)-(2-methyl-3-fluorobenzylidene)-1,2-dihydro-2,2,4-trimethyl-5H-chromeno[3,4-*f*]quinoline (Compound 21);
7,9-difluoro-5(Z)-(3-methyl-2-picolylidene)-1,2-dihydro-2,2,4-trimethyl-5H-chromeno[3,4-*f*]quinoline (Compound 22);
7,9-difluoro-5(Z)-(2,3-dimethylbenzylidene)-1,2-dihydro-2,2,4-trimethyl-5H-chromeno[3,4-*f*]quinoline (Compound 23);
7,9-difluoro-5(Z)-cyanomethylidene-1,2-dihydro-2,2,4-trimethyl-5H-chromeno-[3,4-*f*]-quinoline (Compound 24);
7,9-difluoro-5(Z)-hexylidene-1,2-dihydro-2,2,4-trimethyl-5H-chromeno[3,4-*f*]-quinoline (Compound 25);
7,9-difluoro-5(Z)-(2-methoxy-5-fluorobenzylidene)-1,2-dihydro-2,2,4-trimethyl-5H-chromeno[3,4-*f*]quinoline (Compound 26);
7,9-difluoro-5(Z)-(2,4,5-trifluorobenzylidene)-1,2-dihydro-2,2,4-trimethyl-5H-chromeno[3,4-*f*]quinoline (Compound 27);
7,9-difluoro-5-methylidene-1,2-dihydro-2,2,4-trimethyl-5H-chromeno [3,4-*f*]-quinoline (Compound 28);
7,9-difluoro-5(Z)-bromomethylidene-1,2-dihydro-2,2,4-trimethyl-5H-chromeno [3,4-*f*]-quinoline (Compound 29);
7,9-difluoro-5(Z)-(3-thienylmethylidene)-1,2-dihydro-2,2,4-trimethyl-5H-chromeno[3,4-*f*]quinoline (Compound 30);
7,9-difluoro-5(Z)-(2-thienylmethylidene)-1,2-dihydro-2,2,4-trimethyl-5H-chromeno[3,4-*f*]quinoline (Compound 31);
(±)-7,9-difluoro-5-methoxy-1,2-dihydro-2,2,4-trimethyl-5H-chromeno[3,4-*f*]-quinoline (Compound 32);
(±)-7,9-difluoro-5-phenyl-1,2-dihydro-2,2,4-trimethyl-5H-chromeno[3,4-*f*] quinoline (Compound 33);

UNITED STATES PATENT AND TRADEMARK OFFICE
CERTIFICATE OF CORRECTION

PATENT NO. : 7,163,946 B2
APPLICATION NO. : 10/684212
DATED : January 16, 2007
INVENTOR(S) : Lin Zhi et al.

It is certified that error appears in the above-identified patent and that said Letters Patent is hereby corrected as shown below:

(±)-7,9-difluoro-5-(3-methylphenyl)-1,2-dihydro-2,2,4-trimethyl-5H-chromeno[3,4-*f*]quinoline (Compound 34);
(±)-7,9-difluoro-5-(1,3-benzodioxol-5-yl)-1,2-dihydro-2,2,4-trimethyl-5H-chromeno[3,4-*f*]quinoline (Compound 35);
(±)-7,9-difluoro-5-(4-bromophenyl)-1,2-dihydro-2,2,4-trimethyl-5H-chromeno[3,4-*f*]-quinoline (Compound 36);
(±)-7,9-difluoro-5-(4-chloro-3-methylphenyl)-1,2-dihydro-2,2,4-trimethyl-5H-chromeno[3,4-*f*]quinoline (Compound 37);
(-)-7,9-difluoro-5-(4-chloro-3-methylphenyl)-1,2-dihydro-2,2,4-trimethyl-5H-chromeno[3,4-*f*]quinoline (Compound 38);
(+)-7,9-difluoro-5-(4-chloro-3-methylphenyl)-1,2-dihydro-2,2,4-trimethyl-5H-chromeno[3,4-*f*]quinoline (Compound 39);
(±)-7,9-difluoro-5-(3-fluorophenyl)-1,2-dihydro-2,2,4-trimethyl-5H-chromeno[3,4-*f*]-quinoline (Compound 40);
(±)-7,9-difluoro-5-(3-chlorophenyl)-1,2-dihydro-2,2,4-trimethyl-5H-chromeno[3,4-*f*]-quinoline (Compound 41);
(±)-7,9-difluoro-5-(3-bromophenyl)-1,2-dihydro-2,2,4-trimethyl-5H-chromeno[3,4-*f*]-quinoline (Compound 42);
(±)-7,9-difluoro-5-(4-chlorophenyl)-1,2-dihydro-2,2,4-trimethyl-5H-chromeno[3,4-*f*]-quinoline (Compound 43);
(±)-7,9-difluoro-1,2-dihydro-2,2,4,5-tetramethyl-5H-chromeno[3,4-*f*]quinoline (Compound 44);
(±)-7,9-difluoro-5-(2-oxo-2-phenylethyl)-1,2-dihydro-2,2,4-trimethyl-5H-chromeno-[3,4-*f*]quinoline (Compound 45);
(±)-7,9-difluoro-5-ethyl-1,2-dihydro-2,2,4-trimethyl-5H-chromeno[3,4-*f*]quinoline (Compound 46);
(±)-7,9-difluoro-5-ethenyl-1,2-dihydro-2,2,4-trimethyl-5H-chromeno[3,4-*f*]-quinoline (Compound 47);
(±)-7,9-difluoro-5-(2-oxo-3-butenyl)-1,2-dihydro-2,2,4-trimethyl-5H-chromeno[3,4-*f*]-quinoline (Compound 48);
(±)-7,9-difluoro-1,2-dihydro-α,α,2,2,4-pentamethyl-5H-chromeno[3,4-*f*]quinoline-5-ethanoate (Compound 49);
(±)-7,9-difluoro-5-ethynyl-1,2-dihydro-2,2,4-trimethyl-5H-chromeno[3,4-*f*]-quinoline (Compound 50);
(±)-7,9-difluoro-5-cyano-1,2-dihydro-2,2,4-trimethyl-5H-chromeno[3,4-*f*]-quinoline (Compound 51);
(±)-7,9-difluoro-5-butyl-1,2-dihydro-2,2,4-trimethyl-5H-chromeno[3,4-*f*]quinoline (Compound 52);
(±)-7,9-difluoro-5-(2-thienyl)-1,2-dihydro-2,2,4-trimethyl-5H-chromeno[3,4-*f*]-quinoline (Compound 53);

UNITED STATES PATENT AND TRADEMARK OFFICE
CERTIFICATE OF CORRECTION

PATENT NO.      : 7,163,946 B2
APPLICATION NO. : 10/684212
DATED           : January 16, 2007
INVENTOR(S)     : Lin Zhi et al.

It is certified that error appears in the above-identified patent and that said Letters Patent is hereby corrected as shown below:

(±)-7,9-difluoro-5-(2-furyl)-1,2-dihydro-2,2,4-trimethyl-5H-chromeno[3,4-*f*]-quinoline (Compound 54);

(±)-7,9-difluoro-5-allyl-1,2-dihydro-2,2,4-trimethyl-5H-chromeno[3,4-*f*] quinoline (Compound 55);

(±)-7,9-difluoro-5-[3-(trifluoromethyl)phenyl]-1,2-dihydro-2,2,4-trimethyl-5H-chromeno[3,4-*f*]quinoline (Compound 56);

Ethyl (±)-7,9-difluoro-1,2-dihydro-α-methylene-2,2,4-trimethyl-5H-chromeno[3,4-*f*]-quinoline-5-propanoate (Compound 57);

(±)-7,9-difluoro-1,2-dihydro-β-methylene-2,2,4-trimethyl-5H-chromeno[3,4-*f*]-quinoline-5-propanol (Compound 58);

(±)-7,9-difluoro-1,2-dihydro-β-methylene-2,2,4-trimethyl-5H-chromeno[3,4-*f*]-quinoline-5-propanol acetate (Compound 59);

(±)-7,9-difluoro-5-(1-methylethenyl)-1,2-dihydro-2,2,4-trimethyl-5H-chromeno[3,4-*f*]-quinoline (Compound 60);

(±)-7,9-difluoro-5-(N-methyl-2-pyrrolyl)-1,2-dihydro-2,2,4-trimethyl-5H-chromeno-[3,4-*f*]quinoline (Compound 61);

(±)-7,9-difluoro-5-phenylethynyl-1,2-dihydro-2,2,4-trimethyl-5H-chromeno[3,4-*f*]-quinoline (Compound 62);

(±)-7,9-difluoro-5-(benzo[b]thien-2-yl)-1,2-dihydro-2,2,4-trimethyl-5H-chromeno[3,4-*f*]-quinoline (Compound 63);

(-)-7,9-difluoro-5-(benzo[b]thien-2-yl)-1,2-dihydro-2,2,4-trimethyl-5H-chromeno[3,4-*f*]-quinoline (Compound 64);

(+)-7,9-difluoro-5-(benzo[b]thien-2-yl)-1,2-dihydro-2,2,4-trimethyl-5H-chromeno[3,4-*f*]-quinoline (Compound 65);

(±)-7,9-difluoro-5-(5-methyl-2-furyl)-1,2-dihydro-2,2,4-trimethyl-5H-chromeno-[3,4-*f*]-quinoline (Compound 66);

(±)-7,9-difluoro-5-(2-benzo[b]furyl)-1,2-dihydro-2,2,4-trimethyl-5H-chromeno-[3,4-*f*]-quinoline (Compound 67);

(±)-7,9-difluoro-5-[4-(dimethylamino)phenyl]-1,2-dihydro-2,2,4-trimethyl-5H-chromeno[3,4-*f*]quinoline (Compound 68);

(±)-7,9-difluoro-5-(5-methyl-2-thienyl)-1,2-dihydro-2,2,4-trimethyl-5H-chromeno-[3,4-*f*]-quinoline (Compound 69);

(±)-7,9-difluoro-5-(5-methoxy-2-furyl)-1,2-dihydro-2,2,4-trimethyl-5H-chromeno-[3,4-*f*]-quinoline (Compound 70);

(±)-7,9-difluoro-5-(2-propynyl)-1,2-dihydro-2,2,4-trimethyl-5H-chromeno[3,4-*f*]-quinoline (Compound 71);

(-)-7,9-difluoro-5-(2-propynyl)-1,2-dihydro-2,2,4-trimethyl-5H-chromeno[3,4-*f*]-quinoline (Compound 72);

(+)-7,9-difluoro-5-(2-propynyl)-1,2-dihydro-2,2,4-trimethyl-5H-chromeno[3,4-*f*]-quinoline (Compound 73);

UNITED STATES PATENT AND TRADEMARK OFFICE
CERTIFICATE OF CORRECTION

PATENT NO.      : 7,163,946 B2
APPLICATION NO. : 10/684212
DATED           : January 16, 2007
INVENTOR(S)     : Lin Zhi et al.

It is certified that error appears in the above-identified patent and that said Letters Patent is hereby corrected as shown below:

(±)-7,9-difluoro-5-(1-propynyl)-1,2-dihydro-2,2,4-trimethyl-5H-chromeno
        [3,4-*f*]-quinoline (Compound 74);
    (-)-7,9-difluoro-5-(1-propynyl)-1,2-dihydro-2,2,4-trimethyl-5H-chromeno
        [3,4-*f*]-quinoline (Compound 75);
    (+)-7,9-difluoro-5-(1-propynyl)-1,2-dihydro-2,2,4-trimethyl-5H-chromeno
        [3,4-*f*]-quinoline (Compound 76);
    (±)-7,9-difluoro-5-(4,5-dimethyl-2-furyl)-1,2-dihydro-2,2,4-trimethyl-5H-
        chromeno-[3,4-*f*]quinoline (Compound 77);
    (±)-7,9-difluoro-5-(2-methyl-1-propenyl)-1,2-dihydro-2,2,4-trimethyl-5H-
        chromeno-[3,4-*f*]quinoline (Compound 78);
    (±)-7,9-difluoro-5-(3,4-dimethyl-2-thienyl)-1,2-dihydro-2,2,4-trimethyl-5H-
        chromeno[3,4-*f*]quinoline (Compound 79);
    (±)-7,9-difluoro-5-(3-(3-bromophenyl)phenyl)-1,2-dihydro-2,2,4-trimethyl-5H-
        chromeno[3,4-*f*]quinoline (Compound 80); and
    7,9-difluoro-5-(2-methylbenzylidene)-1,2-dihydro-2,2,4-trimethyl-5H-
        chromeno-[3,4-*f*]-quinoline (Compound 81).

13. A compound according to claim 1, wherein said compound is selected from the group of:
    7,9-difluoro-5(Z)-benzylidene-1,2-dihydro-2,2,4-trimethyl-5H-chromeno[3,4-*f*]-
        quinoline (Compound 10);
    7,9-difluoro-5(Z)-(2-fluorobenzylidene)-1,2-dihydro-2,2,4-trimethyl-5H-
        chromeno-[3,4-*f*]quinoline (Compound 12);
    7,9-difluoro-5(Z)-(3-fluorobenzylidene)-1,2-dihydro-2,2,4-trimethyl-5H-
        chromeno-[3,4-*f*]quinoline (Compound 15);
    7,9-difluoro-5(Z)-(2,5-difluorobenzylidene)-1,2-dihydro-2,2,4-trimethyl-5H-
        chromeno[3,4-*f*]quinoline (Compound 17);
    7,9-difluoro-5(Z)-(2-methoxybenzylidene)-1,2-dihydro-2,2,4-trimethyl-5H-
        chromeno-[3,4-*f*]quinoline (Compound 18);
    7,9-difluoro-5(Z)-(2-methyl-5-fluorobenzylidene)-1,2-dihydro-2,2,4-trimethyl-
        5H-chromeno[3,4-*f*]quinoline (Compound 19);
    7,9-difluoro-5(Z)-(3-methyl-4-picolylidene)-1,2-dihydro-2,2,4-trimethyl-5H-
        chromeno-[3,4-*f*]quinoline (Compound 20);
    7,9-difluoro-5(Z)-(2-methoxy-5-fluorobenzylidene)-1,2-dihydro-2,2,4-
        trimethyl-5H-chromeno[3,4-*f*]quinoline (Compound 26);
    7,9-difluoro-5(Z)-(3-thienylmethylidene)-1,2-dihydro-2,2,4-trimethyl-5H-
        chromeno-[3,4-*f*]quinoline (Compound 30);
    7,9-difluoro-5(Z)-(2-thienylmethylidene)-1,2-dihydro-2,2,4-trimethyl-5H-
        chromeno-[3,4-*f*]quinoline (Compound 31);
    (±)-7,9-difluoro-5-(3-methylphenyl)-1,2-dihydro-2,2,4-trimethyl-5H-chromeno
        [3,4-*f*]-quinoline (Compound 34);

UNITED STATES PATENT AND TRADEMARK OFFICE
CERTIFICATE OF CORRECTION

PATENT NO. : 7,163,946 B2
APPLICATION NO. : 10/684212
DATED : January 16, 2007
INVENTOR(S) : Lin Zhi et al.

It is certified that error appears in the above-identified patent and that said Letters Patent is hereby corrected as shown below:

(-)-7,9-difluoro-5-(4-chloro-3-methylphenyl)-1,2-dihydro-2,2,4-trimethyl-5H-chromeno[3,4-*f*]qunioline (Compound 38);
(±)-7,9-difluoro-5-(3-chlorophenyl)-1,2-dihydro-2,2,4-trimethyl-5H-chromeno[3,4-*f*]-quinoline (Compound 41);
(±)-7,9-difluoro-1,2-dihydro-2,2,4,5-tetramethyl-5H-chromeno[3,4-*f*]quinoline (Compound 44);
(±)-7,9-difluoro-5-allyl-1,2-dihydro-2,2,4-trimethyl-5H-chromeno[3,4-*f*]quinoline (Compound 55);
(±)-7,9-difluoro-5-(3-trifluoromethylphenyl)-1,2-dihydro-2,2,4-trimethyl-5H-chromeno[3,4-*f*]quinoline (Compound 56);
(±)-7,9-difluoro-5-(benzo[b]thien-2-yl)-1,2-dihydro-2,2,4-trimethyl-5H-chromeno[3,4-*f*]quinoline (Compound 63);
(-)-7,9-difluoro-5-(benzo[b]thien-2-yl)-1,2-dihydro-2,2,4-trimethyl-5H-chromeno-[3,4-*f*]quinoline (Compound 64);
(+)-7,9-difluoro-5-(benzo[b]thien-2-yl)-1,2-dihydro-2,2,4-trimethyl-5H-chromeno-[3,4-*f*]quinoline (Compound 65);
(-)-7,9-difluoro-5-(2-propynyl)-1,2-dihydro-2,2,4-trimethyl-5H-chromeno[3,4-*f*]-quinoline (Compound 72);
(-)-7,9-difluoro-5-(1-propynyl)-1,2-dihydro-2,2,4-trimethyl-5H-chromeno[3,4-*f*]-quinoline (Compound 75); and
7,9-difluoro-5-(2-methylbenzylidene)-1,2-dihydro-2,2,4-trimethyl-5H-chromeno-[3,4-*f*]quinoline (Compound 81).

20. A pharmaceutical composition according to claim 15, wherein $R^9$ is selected from the group of hydrogen, F, Cl, Br, CN, $C_1$-$C_6$ alkyl, $C_1$-$C_6$ heteroalkyl, $C_1$-$C_6$ haloalkyl, $C_2$-$C_6$ alkenyl or cycloalkenyl, $C_2$-$C_6$ heteroalkenyl, $C_2$-$C_6$ haloalkenyl $C_2$-$C_6$ alkynyl, $C_2$-$C_6$ heteroalkynyl, $C_2$-$C_6$ haloalkynyl, aryl and heteroaryl, optionally substituted with one or more substituents independently selected from the group of hydrogen, $C_1$-$C_4$ alkyl, F, Cl, Br, I, CN, $NO_2$, $NH_2$, $NHCH_3$, $N(CH_3)_2$, SH, $SCH_3$, OH, $OCH_3$, $OCF_3$, $CF_3$, $C(O)CH_3$, $CO_2CH_3$, $C(O)NH_2$, $OR^{10}$, $SR^{10}$, and $NR^{10}R^{11}$.

23. A pharmaceutical composition according to claim 22, wherein $R^9$ is selected from the group of

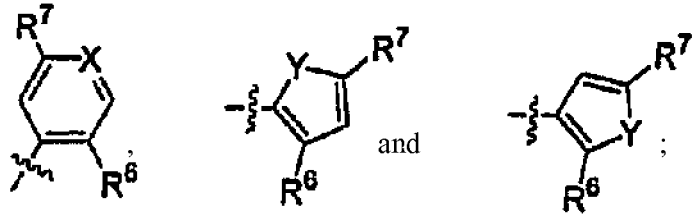

UNITED STATES PATENT AND TRADEMARK OFFICE
CERTIFICATE OF CORRECTION

PATENT NO. : 7,163,946 B2
APPLICATION NO. : 10/684212
DATED : January 16, 2007
INVENTOR(S) : Lin Zhi et al.

It is certified that error appears in the above-identified patent and that said Letters Patent is hereby corrected as shown below:

wherein:

$R^6$ is selected from the group of hydrogen, F, Cl, Br, $C_1$-$C_4$ alkyl, $OR^{10}$, $SR^{10}$, and $NR^{10}R^{11}$;
$R^7$ is hydrogen, F, or Cl;
$R^{10}$ and $R^{11}$ each independently is hydrogen, or $C_1$-$C_4$ alkyl;
X is CH or N; and
Y is selected from the group of O, S, and $NR^{10}$.--

Signed and Sealed this

Twentieth Day of March, 2007

JON W. DUDAS
*Director of the United States Patent and Trademark Office*